United States Patent
Durón et al.

(10) Patent No.: US 9,725,426 B2
(45) Date of Patent: Aug. 8, 2017

(54) CYSTATHIONINE-γ-LYASE (CSE) INHIBITORS

(71) Applicant: SOVA PHARMACEUTICALS, INC., La Jolla, CA (US)

(72) Inventors: Sergio G. Durón, San Diego, CA (US); Justin Chapman, San Diego, CA (US); Simon G. Sydserff, San Diego, CA (US); Srinivas G. Rao, Encinitas, CA (US); Gregory Stein, San Diego, CA (US); Warren Wade, San Diego, CA (US)

(73) Assignee: SOVA PHARMACEUTICALS, INC., La Jolla, CA (US)

( * ) Notice: Subject to any disclaimer, the term of this patent is extended or adjusted under 35 U.S.C. 154(b) by 0 days.

(21) Appl. No.: 14/416,596

(22) PCT Filed: Jul. 23, 2013

(86) PCT No.: PCT/US2013/051745
§ 371 (c)(1),
(2) Date: Jan. 22, 2015

(87) PCT Pub. No.: WO2014/018570
PCT Pub. Date: Jan. 30, 2014

(65) Prior Publication Data
US 2015/0266837 A1    Sep. 24, 2015

Related U.S. Application Data

(60) Provisional application No. 61/675,754, filed on Jul. 25, 2012.

(51) Int. Cl.
| | | |
|---|---|---|
| *C07D 255/02* | (2006.01) | |
| *C07D 257/06* | (2006.01) | |
| *C07D 271/07* | (2006.01) | |
| *A61K 31/41* | (2006.01) | |
| *A61K 31/4245* | (2006.01) | |
| *A61K 45/06* | (2006.01) | |
| *C07C 311/61* | (2006.01) | |
| *A61K 31/433* | (2006.01) | |
| *A61K 31/445* | (2006.01) | |
| *A61K 31/57* | (2006.01) | |
| *A61K 31/18* | (2006.01) | |
| *C07C 311/19* | (2006.01) | |

(52) U.S. Cl.
CPC ............ *C07D 271/07* (2013.01); *A61K 31/18* (2013.01); *A61K 31/41* (2013.01); *A61K 31/4245* (2013.01); *A61K 31/433* (2013.01); *A61K 31/445* (2013.01); *A61K 31/57* (2013.01); *A61K 45/06* (2013.01); *C07C 311/19* (2013.01); *C07C 311/61* (2013.01); *C07D 255/02* (2013.01); *C07D 257/06* (2013.01)

(58) Field of Classification Search
None
See application file for complete search history.

(56) References Cited

U.S. PATENT DOCUMENTS

| | | | |
|---|---|---|---|
| 3,352,909 A | 11/1967 | Sayigh et al. | |
| 4,610,717 A | * 9/1986 | Mansuri ............... | A01N 43/647 504/253 |

FOREIGN PATENT DOCUMENTS

| | | | |
|---|---|---|---|
| DE | 13769 A | 9/1957 | |
| DE | 207626 | * 3/1984 | ........... C07D 249/14 |
| EP | 1739081 A1 | 1/2007 | |
| WO | WO2014/018570 | 1/2014 | |

OTHER PUBLICATIONS

Das, U.N. (Journal of Inflammation Research, 2010:3, pp. 143-170).*
STN Registry Entry for CAS RN 21732-98-9; Entered STN Registry Nov. 16, 1984; Accessed Sep. 28, 2015.*
Emilsson et al., Acta Pharmaceutica Suecica, Svensk Farmaceutisk Tidskrift, vol. 20, No. 3, 1983.*
Lieber et al., Journal of the American Chemical Society (1951), 73, 1313-17.*
Scott et al., J. Org. Chem., vol. 19, pp. 742-748 (1954).*
PCT/US2013/051745 International Preliminary Report on Patentability dated Jan. 27, 2015.
PCT/US2013/051745 International Search Report and Written Opinion dated Nov. 28, 2013.
Satzinger. 5-Substituierte und 1,5-kondensierte tetrazole. Liebigs Ann Chem 638:159-173 (1960).
Tao et al. Nitrogen-rich 5-(1-methylhydrazinyl)tetrazole and its copper and silver complexes. Inorg. Chem. 51:5305-5312 (2012).
Heeb et al. New Energetic materials for Nitrocellulose based Propellants. International Annual Conference of ICT (2007), 38th, 101/1-101/13.
Auterhoff et al. Archiv der Pharmazie pp. 263-267 (1970).
Banert et al. Synthesis of N-[1-(2-Hydroxyethyl)-1H-tetrazol-5-yl]-N-methylhydrazine as Polymeric Precursor Eur. J. Org. Chem. 2009:275-281 (2009).
Bhatia et al. Pro-inflammatory effects of hydrogen sulphide on substance P in caerulein-induced acute pancreatitis. J Cell Mol Med 12:580-590 (2008).
Chemical Abstracts Service Database Accession No. 297763-47-4. Benzaldehyde, 2,4-dichloro-,2-(2H-tetrazol-5-yl)hydrazone. (1 pg.) (2000).
Chemical Abstracts Service Database Accession No. 325483-03-3. Cyclohexanone, 2-(2H-tetrazol-5-yl)hydrazone. (1 pg.) (2001).

(Continued)

*Primary Examiner* — Alicia L Otton
(74) *Attorney, Agent, or Firm* — Wilson Sonsini Goodrich & Rosati

(57) ABSTRACT

Described herein are compounds and pharmaceutical compositions containing such compounds which inhibit cystathionine-γ-lyase (CSE). Also described herein are methods for using such CSE inhibitors, alone or in combination with other compounds, for treating diseases or conditions that would benefit from CSE inhibition.

19 Claims, 10 Drawing Sheets

(56) References Cited

OTHER PUBLICATIONS

Dam et al. Inhibition of cystathionine gamma-lyase and the biosynthesis of endogenous hydrogen sulphide ameliorates gentamicin-induced nephrotoxicity. Eur J Pharmacol 685(1-3):165-173 (2012).
Mayants et al. Decomposition of azotetrazole salts in acidic medial. Database Accession No. 1992:234937 (1992).
Mitsos. Isosteres in medicinal chemistry definition of Isosterism. Chem Rev. pp. 3147-3176 Christos Mitsos Group Meeting 2006. Retrieved from http://scripps.edu/baran/images/grpmtgpdf/Mistos_Feb_06.pdf (7 pgs.).
Pan et al. S-Propargyl-cysteine (SPRC) attenuated lipopolysaccharide-induced inflammatory response in H9c2 cells involved in a hydrogen sulfide-dependent mechanism. Amino Acids 41:205-215 (2011).
PubChem compound. Hydrazinesulfonic acid (CID 10313107—create dateOct. 25, 2006). PubChem datasheet retrieved from the internet Jan. 2015 (10 pgs.).
Scott et al. Polynitrogen Systems from the Hydrazinocarbonic Acids. Part IX. The Synthesis and Bromination of Some 5-Tetrazolyl and Related -hydrazones. J Org Chem 22(6):692-694 (1957).
Shchipanov et al. Tetrazole Derivatives. XII Synthesis and Some Properties of 5-Tetrazolyhydrazones.Chemistry of Heterocyclic Compounds 11:746-750 (1975).
Sun et al. Structural basis for the inhibition mechanism of human cystathionine gamma-lyase, an enzyme responsible for the production of H(2)S. J. Biol. Chem. 284:3076-3085 (2009).
Takahashi et al. Upregulation of Ca(v)3.2 T-type calcium channels targeted by endogenous hydrogen sulfide contributes to maintenance of neuropathic pain. Pain 150:183-191 (2010).
Kawabata et al. Hydrogen sulfide as a novel nociceptive messenger. Pain 132(1-2):74-81 (2007).
STN Registry ACS RN14392-55-3 (Nov. 16, 1984).
Zhao-Xu et al. Theoretical Study on Tetrazole and its Derivatives(6). Acta Phys.—Chim. Sin. 14(8):757-764 (English Abstract).
STN Registry Database ASC RN45803-71-2 (1 pg.) (1984).
STN Registry Database ASC RN763039-91-4 (1 pg.) (2004).
Emilsson et al. Synthesis and antihypertensive activity of some 3-substituted 4H-1,2,4-triazoles. Acta Pharmaceutica Suecica 24(3):123-134 (1987).
Gehlen et al. 2-amino-1,3,4-oxadiazoles. Part XXXII. Ring cleavage of 2-imino-3-alkyl-5-aryl-1,3,4-oxadiazolines with ethyl carbazate and secondary reactions. Archiv der Pharmazie and Berichte der Deutschen Pharmazeutischen Geslleschaft 303(3):263-267 (1970).

\* cited by examiner

CSE Duration of Effect

CYSTATHIONINE-γ-LYASE (CSE) INHIBITORS

CROSS-REFERENCE

This application claims the benefit of U.S. Application No. 61/675,754, filed Jul. 25, 2012, which is incorporated by reference in its entirety.

BACKGROUND OF THE INVENTION

Hydrogen sulfide ($H_2S$) is a recognized endogenous gasotransmitter involved in multiple signaling pathways that impact various aspects of physiological and pathological processes. Such processes include, but are not limited to; pain, inflammation, neurodegenerative disorders, regulation of breathing, respiratory disorders, cutaneous injuries, regulation of blood pressure, metabolic disorders, and urinary disorders, among others. Cystathionine-γ-lyase (CSE) is a key enzyme involved in the generation of $H_2S$ and an important target for therapeutic intervention in $H_2S$-mediated pathologies and disorders. Compounds that can effectively modulate CSE activity will provide important therapeutic opportunities in disorders sensitive to $H_2S$ production.

SUMMARY OF THE INVENTION

Described herein are inhibitors of cystathionine-γ-lyase (CSE). Also disclosed herein are methods for synthesizing such CSE inhibitors and methods for using such CSE inhibitors in the treatment of diseases wherein CSE inhibition provides therapeutic benefit to the patient having the disease. Further described are pharmaceutical formulations that include a CSE inhibitor.

In one aspect are compounds having the structure of Formula (I):

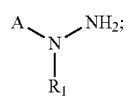

Formula (I)

wherein:
  A is a carboxylic acid isostere;
  $R_1$ is substituted or unsubstituted $C_3$-$C_6$alkyl, substituted or unsubstituted heteroalkyl, substituted or unsubstituted heterocycloalkyl, substituted or unsubstituted aryl, or substituted or unsubstituted heteroaryl; or a pharmaceutically acceptable salt, solvate, or prodrug thereof.

In another aspect are compounds having the structure of Formula (II):

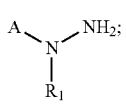

Formula (II)

wherein:
  $R_1$ is H, substituted or unsubstituted alkyl, substituted or unsubstituted heteroalkyl, substituted or unsubstituted heterocycloalkyl, substituted or unsubstituted aryl, or substituted or unsubstituted heteroaryl;

A is selected from

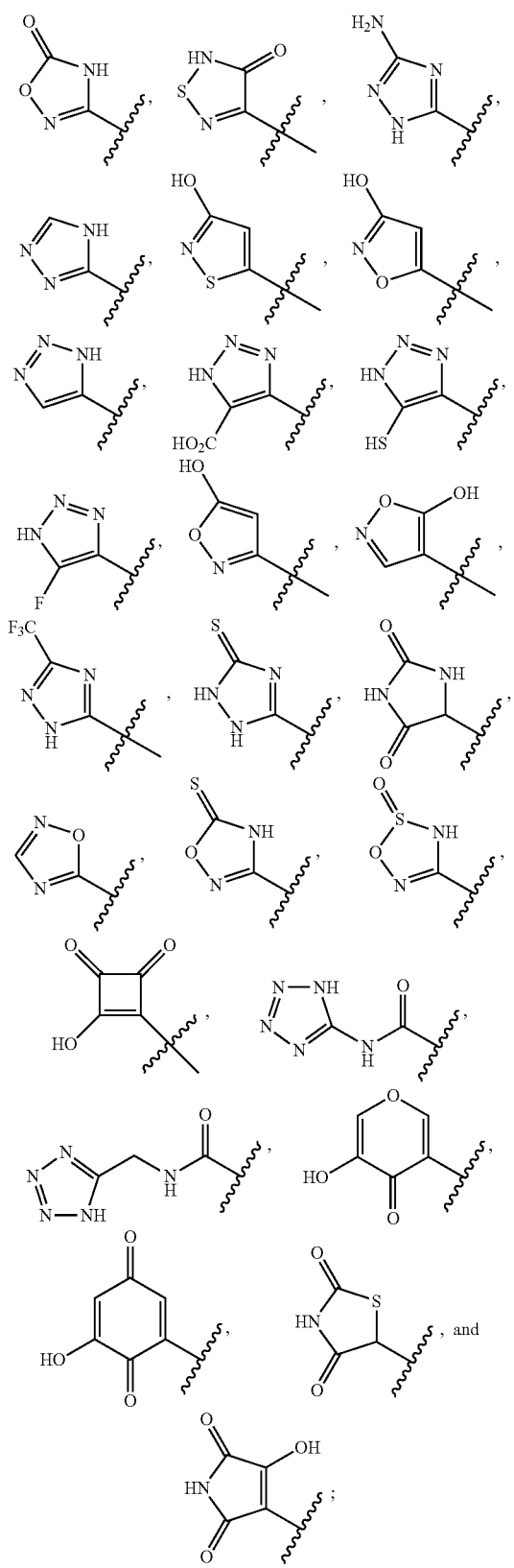

or a pharmaceutically acceptable salt, solvate, or prodrug thereof.

In another aspect are compounds having the structure of Formula (III):

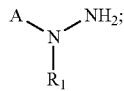

Formula (III)

wherein:

R₁ is H, substituted or unsubstituted alkyl, substituted or unsubstituted heteroalkyl, substituted or unsubstituted heterocycloalkyl, substituted or unsubstituted aryl, or substituted or unsubstituted heteroaryl;

A is a carboxylic acid isostere selected from —SO₃H, —SO₂NHR₄, —P(O)(OR₄)₂, —P(O)(R₄)(OR₄), —CON(R₄)₂, —CONHNHSO₂R₄, —CONHSO₂R₄, —C(R₄)₂B(OR₅)₂, and —CON(R₄)C(R₄)₂B(OR₅)₂; wherein each R₄ is independently H, OH, substituted or unsubstituted alkyl, or substituted or unsubstituted aryl; and R₅ is H or C₁-C₆alkyl; or a pharmaceutically acceptable salt, solvate, or prodrug thereof.

In another aspect are compounds having the structure of Formula (IV):

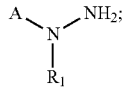

Formula (IV)

wherein:

A is

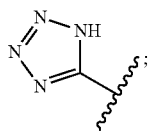 [SMILES: *c1nnn[nH]1]

R₁ is substituted or unsubstituted C₂-C₆alkyl, substituted or unsubstituted heteroalkyl, substituted or unsubstituted heterocycloalkyl, substituted or unsubstituted aryl, or substituted or unsubstituted heteroaryl; or a pharmaceutically acceptable salt, solvate, or prodrug thereof.

In another aspect are compounds having the structure of Formula (V):

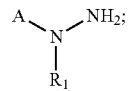

Formula (V)

wherein:

A is

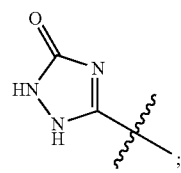

R₁ is H, substituted or unsubstituted C₃-C₆alkyl, substituted or unsubstituted heteroalkyl, substituted or unsubstituted heterocycloalkyl, substituted or unsubstituted aryl, or substituted or unsubstituted heteroaryl; or a pharmaceutically acceptable salt, solvate, or prodrug thereof.

Provided herein, in some embodiments, are methods of treating or preventing or reducing the incidence of acute kidney injury (AKI) secondary to a toxic agent (e.g., cisplatin, aminoglycosides, and radiologic contrast material), nociceptive pain, acute post-operative pain, neuropathic pain, trigeminal neuralgia, diabetic peripheral neuropathy, herpetic neuralgia, post-herpetic neuralgia, inflammatory pain, mixed neuropathic pain and inflammatory pain states, rheumatoid arthritis, inflammatory bowel disease, irritable bowel syndrome, osteoarthritis, acute pancreatitis, chronic pancreatitis, pain associated with acute pancreatitis, pain associated with chronic pancreatitis, migraine headache, gout, ankylosing spondylititis, systemic lupus erythematosus (SLE), system inflammatory response syndrome (SIRS), multi-organ dysfunction syndrome (MODS), asthma, chronic obstructive pulmonary disease (COPD), sensitive skin, acne, rosacea, contact dermatitis, or pain associated with cancer, in individuals in need thereof comprising administration of a therapeutically effective amount of a compound of Formula (I), (II), (III), (IV), (V), or (VI) to the individual in need thereof. In some embodiments the pain associated with cancer is associated with pancreatic cancer. In some embodiments the pain associated with cancer is associated with lung cancer. In some embodiments the pain associated with cancer is associated with prostate cancer. In some embodiments the pain associated with cancer is associated with breast cancer.

Also provided herein, in some embodiments, are methods of treating or preventing or reducing the incidence of acute post-operative pain, neuropathic pain, trigeminal neuralgia, diabetic peripheral neuropathy, herpetic neuralgia, post-herpetic neuralgia, inflammatory pain, rheumatoid arthritis, osteoarthritis, or migraine headache, in individuals in need thereof comprising administration of a therapeutically effective amount of a compound of Formula (I), (II), (III), (IV), (V), or (VI) to the individual in need thereof.

Also provided herein, in some embodiments, are methods of treating or preventing or reducing the incidence of acute kidney injury (AKI) secondary to a toxic agent (e.g., cisplatin, aminoglycosides, and radiologic contrast material), nociceptive pain, acute post-operative pain, neuropathic pain, trigeminal neuralgia, diabetic peripheral neuropathy, herpetic neuralgia, post-herpetic neuralgia, inflammatory pain, mixed neuropathic pain and inflammatory pain states, rheumatoid arthritis, inflammatory bowel disease, irritable bowel syndrome, osteoarthritis, acute pancreatitis, chronic pancreatitis, pain associated with acute pancreatitis, pain associated with chronic pancreatitis, migraine headache, gout, ankylosing spondylititis, systemic lupus erythematosus (SLE), system inflammatory response syndrome (SIRS), multi-organ dysfunction syndrome (MODS), asthma, chronic obstructive pulmonary disease (COPD), sensitive skin, acne, rosacea, contact dermatitis, or pain associated with cancer, in individuals in need thereof comprising administration of a therapeutically effective amount of 2-hydrazinylacetic acid hydrochloride, 2-(2-(propan-2-ylidene)hydrazinyl)acetic acid, 4-((2-(1H-tetrazol-5-yl)hydrazinyl)methyl)-N,N-dimethylaniline, (E)-4-((2-(1H-tetrazol-5-yl)hydrazono)methyl)-N,N-diethylaniline, (E)-1-((2-(1H-tetrazol-5-yl)hydrazono)methyl)naphthalen-2-ol, (E)-5-(2-(benzo[d][1,3]dioxol-5-ylmethylene)hydrazinyl)-1H-tetrazole, (E)-4-((2-(1H-tetrazol-5-yl)hydrazono)methyl)

phenol, (E)-5-(2-(4-nitrobenzylidene)hydrazinyl)-1H-tetrazole, (E)-5-(2-(furan-2-ylmethylene)hydrazinyl)-1H-tetrazole, 5-hydrazinyl-1H-tetrazole, 5-(1-methylhydrazinyl)-1H-tetrazole, 5-(1-methylhydrazinyl)-1H-1,2,4-triazol-3(2H)-one, 5-(1-ethylhydrazinyl)-1H-1,2,4-triazol-3(2H)-one, or 5-(hydrazinylmethyl)-1H-tetrazole to the individual in need thereof.

Also provided herein, in some embodiments, are methods of treating or preventing or reducing the incidence of acute post-operative pain, neuropathic pain, trigeminal neuralgia, diabetic peripheral neuropathy, herpetic neuralgia, post-herpetic neuralgia, inflammatory pain, rheumatoid arthritis, osteoarthritis, or migraine headache, in individuals in need thereof comprising administration of a therapeutically effective amount of 2-hydrazinylacetic acid hydrochloride, 2-(2-(propan-2-ylidene)hydrazinyl)acetic acid, 4-((2-(1H-tetrazol-5-yl)hydrazinyl)methyl)-N,N-dimethylaniline, (E)-4-((2-(1H-tetrazol-5-yl)hydrazono)methyl)-N,N-diethylaniline, (E)-1-((2-(1H-tetrazol-5-yl)hydrazono)methyl)naphthalen-2-ol, (E)-5-(2-(benzo[d][1,3]dioxol-5-ylmethylene)hydrazinyl)-1H-tetrazole, (E)-4-((2-(1H-tetrazol-5-yl)hydrazono)methyl)phenol, (E)-5-(2-(4-nitrobenzylidene)hydrazinyl)-1H-tetrazole, (E)-5-(2-(furan-2-ylmethylene)hydrazinyl)-1H-tetrazole, 5-hydrazinyl-1H-tetrazole, 5-(1-methylhydrazinyl)-1H-tetrazole, 5-(1-methylhydrazinyl)-1H-1,2,4-triazol-3(2H)-one, 5-(1-ethylhydrazinyl)-1H-1,2,4-triazol-3(2H)-one, or 5-(hydrazinylmethyl)-1H-tetrazole to the individual in need thereof.

In some embodiments, the method further comprises administrating a second agent selected from carbonic anhydrase inhibitors, cholinesterase inhibitors, adenosine inhibitors, progestational agents, opiod antagonists, central nervous system stimulants, selective serotonin reuptake inhibitors (SSRIs), dual 5-HT-NE reuptake inhibitors (SN-RI's), antidepressants, antihypertensives, calcium channel antagonists, ACE inhibitors, respiratory stimulants, alpha-2 adrenergic agonists, gamma aminobutyric acid agonists, antiepileptic drugs, NSAIDs, steroids, and glutamate antagonists. In some embodiments, the method further comprises administering a second agent selected from acetazolamide, theophylline, progesterone, donepezil, naloxone, nicotine, paroxetine, protriptyline, metoprolol, cilazapril, propranolol, atenolol, hydrochlorothiazide, isradipine, spirapril, doxapram, clonidine, baclofen, sabeluzole, gabapentin, pregablin, and duloxetine.

In some of the aforementioned embodiments, a compound of Formula (I), (II), (III), (IV), (V), or (VI) inhibits or partially inhibits the activity of cystathionine-gamma-lyase (CSE). In some specific embodiments, the compound of Formula (I), (II), (III), (IV), (V), or (VI) that inhibits or partially inhibits the activity of CSE, directly or indirectly reduces the sensitization or direct activation of cation conductance channels (e.g., TRP, CaV, NaV, Katp ion channels) in an individual in need thereof. In some specific embodiments, the compound of Formula (I), (II), (III), (IV), (V), or (VI) that inhibits or partially inhibits the activity of CSE reduces the sensitization or direct activation of cation conducatance channels (e.g., TRP, CaV, NaV, Katp ion channels) improving hyperalgesia in an individual in need thereof. In some embodiments, the compound of Formula (I), (II), (III), (IV), (V), or (VI) that inhibits or partially inhibits the activity of cystathionine-γ-lyase (CSE) is administered orally, subcutaneously, topically, intramuscularly, or intravenously.

In some of the aforementioned embodiments, 2-hydrazinylacetic acid hydrochloride, 2-(2-(propan-2-ylidene)hydrazinyl)acetic acid, 4-((2-(1H-tetrazol-5-yl)hydrazinyl)methyl)-N,N-dimethylaniline, (E)-4-((2-(1H-tetrazol-5-yl)hydrazono)methyl)-N,N-diethylaniline, (E)-1-((2-(1H-tetrazol-5-yl)hydrazono)methyl)naphthalen-2-ol, (E)-5-(2-(benzo[d][1,3]dioxol-5-ylmethylene)hydrazinyl)-1H-tetrazole, (E)-4-((2-(1H-tetrazol-5-yl)hydrazono)methyl)phenol, (E)-5-(2-(4-nitrobenzylidene)hydrazinyl)-1H-tetrazole, (E)-5-(2-(furan-2-ylmethylene)hydrazinyl)-1H-tetrazole, 5-hydrazinyl-1H-tetrazole, 5-(1-methylhydrazinyl)-1H-tetrazole, 5-(1-methylhydrazinyl)-1H-1,2,4-triazol-3(2H)-one, 5-(1-ethylhydrazinyl)-1H-1,2,4-triazol-3(2H)-one, or 5-(hydrazinylmethyl)-1H-tetrazole inhibits or partially inhibits the activity of cystathionine-gamma-lyase (CSE). In some specific embodiments, 2-hydrazinylacetic acid hydrochloride, 2-(2-(propan-2-ylidene)hydrazinyl)acetic acid, 4-((2-(1H-tetrazol-5-yl)hydrazinyl)methyl)-N,N-dimethylaniline, (E)-4-((2-(1H-tetrazol-5-yl)hydrazono)methyl)-N,N-diethylaniline, (E)-1-((2-(1H-tetrazol-5-yl)hydrazono)methyl)naphthalen-2-ol, (E)-5-(2-(benzo[d][1,3]dioxol-5-ylmethylene)hydrazinyl)-1H-tetrazole, (E)-4-((2-(1H-tetrazol-5-yl)hydrazono)methyl)phenol, (E)-5-(2-(4-nitrobenzylidene)hydrazinyl)-1H-tetrazole, (E)-5-(2-(furan-2-ylmethylene)hydrazinyl)-1H-tetrazole, 5-hydrazinyl-1H-tetrazole, 5-(1-methylhydrazinyl)-1H-tetrazole, 5-(1-methylhydrazinyl)-1H-1,2,4-triazol-3(2H)-one, 5-(1-ethylhydrazinyl)-1H-1,2,4-triazol-3(2H)-one, or 5-(hydrazinylmethyl)-1H-tetrazole, directly or indirectly reduces the sensitization or direct activation of cation conductance channels (e.g., TRP, CaV, NaV, Katp ion channels) in an individual in need thereof.

In some specific embodiments, 2-hydrazinylacetic acid hydrochloride, 2-(2-(propan-2-ylidene)hydrazinyl)acetic acid, 4-((2-(1H-tetrazol-5-yl)hydrazinyl)methyl)-N,N-dimethylaniline, (E)-4-((2-(1H-tetrazol-5-yl)hydrazono)methyl)-N,N-diethylaniline, (E)-1-((2-(1H-tetrazol-5-yl)hydrazono)methyl)naphthalen-2-ol, (E)-5-(2-(benzo[d][1,3]dioxol-5-ylmethylene)hydrazinyl)-1H-tetrazole, (E)-4-((2-(1H-tetrazol-5-yl)hydrazono)methyl)phenol, (E)-5-(2-(4-nitrobenzylidene)hydrazinyl)-1H-tetrazole, (E)-5-(2-(furan-2-ylmethylene)hydrazinyl)-1H-tetrazole, 5-hydrazinyl-1H-tetrazole, 5-(1-methylhydrazinyl)-1H-tetrazole, 5-(1-methylhydrazinyl)-1H-1,2,4-triazol-3(2H)-one, 5-(1-ethylhydrazinyl)-1H-1,2,4-triazol-3(2H)-one, or 5-(hydrazinylmethyl)-1H-tetrazole reduces the sensitization or direct activation of cation conducatance channels (e.g., TRP, CaV, NaV, Katp ion channels) improving hyperalgesia in an individual in need thereof. In some embodiments, 2-hydrazinylacetic acid hydrochloride, 2-(2-(propan-2-ylidene)hydrazinyl)acetic acid, 4-((2-(1H-tetrazol-5-yl)hydrazinyl)methyl)-N,N-dimethylaniline, (E)-4-((2-(1H-tetrazol-5-yl)hydrazono)methyl)-N,N-diethylaniline, (E)-1-((2-(1H-tetrazol-5-yl)hydrazono)methyl)naphthalen-2-ol, (E)-5-(2-(benzo[d][1,3]dioxol-5-ylmethylene)hydrazinyl)-1H-tetrazole, (E)-4-((2-(1H-tetrazol-5-yl)hydrazono)methyl)phenol, (E)-5-(2-(4-nitrobenzylidene)hydrazinyl)-1H-tetrazole, (E)-5-(2-(furan-2-ylmethylene)hydrazinyl)-1H-tetrazole, 5-hydrazinyl-1H-tetrazole, 5-(1-methylhydrazinyl)-1H-tetrazole, 5-(1-methylhydrazinyl)-1H-1,2,4-triazol-3(2H)-one, 5-(1-ethylhydrazinyl)-1H-1,2,4-triazol-3(2H)-one, or 5-(hydrazinylmethyl)-1H-tetrazole is administered orally, subcutaneously, topically, intramuscularly, or intravenously.

DETAILED DESCRIPTION OF THE INVENTION

Figure 1:
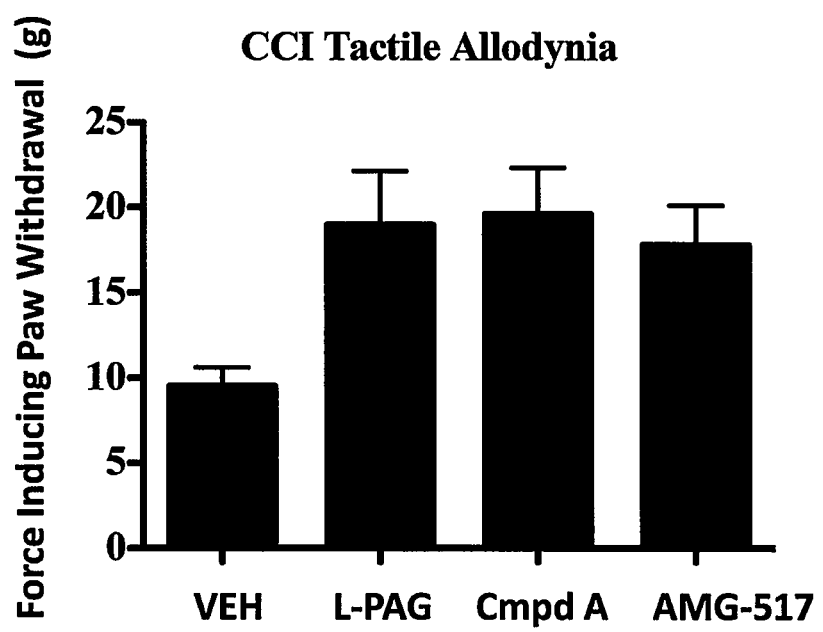
FIG. 1 shows a graph of L-propargyl glycine (L-PAG), 100 mpk IP; Compound A (Cmpd A), 30 mpk oral; and AMG-517; 3 mpk oral in the CCI Tactile Allodynia model (Example 3a).

A devastating health problem in the United States and abroad is the inadequate treatment of pain. Pain can be acute or chronic and can be categorized as nociceptive, pathologic/neuropathic, and inflammatory pain. While acute pain is usually self-limited, chronic pain persists for three months or longer. One third of all Americans suffer from some form of chronic pain, and a third of these have pain, which is resistant to current medical therapy. The economic impact of pain is equally large at approximately $100 billion annually. Severe pain syndromes reduce quality of life in patients, partly because reduced analgesic effectiveness with chronic opiate therapy (i.e., hyperalgesia and tolerance) leads to escalating doses and distressing side effects.

Neuropathic pain is a particular type of chronic, pathologic pain that has a complex and variable etiology. It is frequently a chronic condition attributable to complete or partial transection of a nerve, trauma or injury to a nerve, nerve plexus or soft tissue, or other conditions, including cancer and idiopathic causes. Neuropathic pain is characterized by hyperalgesia (lowered pain threshold and enhanced pain perception) and by allodynia (pain from innocuous mechanical or thermal stimuli). The condition is progressive in nature. Because the hyperesthetic component of neuropathic pain does not respond to the same pharmaceutical interventions as does more generalized and acute forms of pain, development of effective long-term treatment modalities has been problematic.

The treatment of pain is of great importance in medicine. However, little progress has been made in preventing the development of neuropathic pain, inflammatory pain and hyperalgesia. Thus, there is a serious need for new agents and methods of treating pain conditions.

Endogenous hydrogen sulfide is synthesized through degradation of L-cysteine by cystathionine-gamma-lyase (CSE) or cystathionine-beta synthase (CBS). The enzyme cystathionine-γ-lyase (CSE) converts cystathionine to L-cysteine, yielding pyruvate, ammonia and hydrogen sulfide. Hydrogen sulfide ($H_2S$) is a gasotransmitter physiologically regulating neuronal transmission and vascular tone. CBS is the predominant $H_2S$ synthesizing enzyme in the brain, while CSE preponderates in the peripheral tissues.

Hydrogen sulfide in some embodiments is known to play a role in nociception by sensitizing or directly activating various ion channels (e.g., TRPV channels, TRPA1, NaV and CaV cation channels) potentially contributing to hyperalgesia as well as many other physiological processes including vasodilation (e.g., smooth muscle relaxation and/or opening of vascular smooth muscle K channels), and neuromodulation (e.g., induction of hippocampal long-term potentiation). Studies have shown that hydrogen sulfide is also associated with inflammation (e.g., hindpaw edema), acute pancreatitis, endotoxemia and sepsis.

Neuropathic Pain

Disclosed herein, in certain embodiments, are methods of treating neuropathic pain in an individual in need thereof. Neuropathic pain is a complex, chronic, pathologic pain state that may or may not be accompanied by an active tissue injury process. With neuropathic pain, the nerve fibers themselves may be damaged, dysfunctional or injured. These damaged nerve fibers send incorrect signals to other pain centers, potentially resulting in altered functioning at the level of the central nervous system. The impact of nerve fiber injury includes a change in nerve function both at the site of injury and areas around the injury.

One example of neuropathic pain is called phantom limb syndrome. This occurs when an arm or a leg has been removed because of illness or injury, but the brain still gets pain messages from the nerves that originally carried impulses from the missing limb. These nerves now misfire and cause pain.

Other examples of neuropathic pain include, but are not limited to, trigeminal neuralgia, painful diabetic peripheral neuropathy, sciatica, and post-herpetic neuralgia. Trigeminal neuralgia is a chronic pain condition that affects the trigeminal nerve, which carries sensation from the face to the brain. In trigeminal neuralgia, even mild stimulation of the face, such as from brushing teeth or putting on makeup, may trigger a jolt of excruciating pain.

Trigeminal neuralgia can occur as short, mild attacks, however, trigeminal neuralgia can also progress, causing longer, more frequent bouts of searing pain. Trigeminal neuralgia affects women more often than men, and it's more likely to occur in people who are older than 50.

Medications to lessen or block the pain signals sent to the brain are the most common initial treatment for trigeminal neuralgia. Anticonvulsants such as carbazepine can be prescribed to treat trigeminal neuralgia. Carbamazepine (Tegretol, Carbatrol) is the drug most commonly prescribed, and with the most demonstrated effectiveness, for trigeminal neuralgia. Other anticonvulsant drugs used to treat trigeminal neuralgia include oxcarbazepine (Trileptal), lamotrigine (Lamictal), phenytoin (Dilantin, Phenytek) and gabapentin (Neurontin).

Antispasmodic agents can also be used to treat trigeminal neuralgia. Muscle-relaxing agents such as baclofen may be used alone or in combination with carbamazepine or phenytoin. Side effects may include confusion, nausea and drowsiness.

Alcohol injections provide temporary pain relief by numbing the affected areas of the face. Typically, alcohol is injected into the part of the face corresponding to the trigeminal nerve branch causing pain. The pain relief isn't permanent, so repeated injections or a different procedure in the future may be needed. Side effects may include infections at the injection site, bleeding and damage to nearby nerves.

Surgery is another option for the treatment of trigeminal neuralgia. The goal of surgery for trigeminal neuralgia is either to stop the blood vessel from compressing the trigeminal nerve or to damage the trigeminal nerve to keep it from malfunctioning. Damaging the nerve often causes temporary or permanent facial numbness, and with any of the surgical procedures, the pain can return months or years later.

Surgical options for trigeminal neuralgia include gamma-knife radiosurgery (GKR); and microvascular decompression (MVD). GKR involves delivering a focused, high dose of radiation to the root of the trigeminal nerve. Because of GKR's effectiveness and safety compared with other surgical options for trigeminal neuralgia, the procedure is becoming widely used and may be offered earlier than other surgical procedures.

Gamma-knife radiosurgery uses radiation to damage the trigeminal nerve and reduce or eliminate pain. Relief occurs gradually and can take several weeks to begin. GKR is successful in eliminating pain for the majority of people. If pain recurs, the procedure can be repeated. Fewer than 5 percent of people who undergo this procedure experience side effects, which may include lasting loss of facial sensation. The procedure is painless and typically is done without anesthesia.

Microvascular decompression (MVD) involves relocating or removing blood vessels that are in contact with the trigeminal root. During MVD, the doctor makes an incision behind the ear on the side of the pain. Then, through a small hole in the skull, part of the brain is lifted to expose the trigeminal nerve. Any artery in contact with the nerve root is directed away from the nerve, and the surgeon places a pad between the nerve and the artery. If a vein is compressing the nerve, the surgeon typically will remove it.

MVD can successfully eliminate or reduce pain most of the time, but pain can recur in some people. While MVD has a high success rate, it also carries risks. There are small chances of decreased hearing, facial weakness, facial numbness, double vision, and even a stroke or death. Most people who have this procedure have no facial numbness afterward.

Note that if no artery or vein appears to be compressing the nerve, part of the nerve may be severed instead. This procedure is called a rhizotomy.

During glycerol injection, a needle is inserted through the face and into an opening in the base of the skull. The needle is guided into the trigeminal cistern, a small sac of spinal fluid that surrounds the trigeminal nerve ganglion, where the trigeminal nerve divides into three branches, and part of its root. Images are made to confirm that the needle is in the proper location, and then a small amount of sterile glycerol is injected. After three or four hours, the glycerol damages the trigeminal nerve and blocks pain signals. Initially, this procedure relieves pain in most people. However, some people have a later recurrence of pain, and many experience facial numbness or tingling.

In balloon compression of the trigeminal nerve, a hollow needle is inserted through the face and into an opening in the base of the skull. Then, a thin, flexible tube (catheter) with a balloon on the end is threaded through the needle. The balloon is inflated with enough pressure to damage the nerve and block pain signals. Balloon compression successfully controls pain in most people, at least for a while. Most people undergoing this procedure experience some facial numbness, and some experience temporary or permanent weakness of the muscles used to chew.

Electric current (radiofrequency thermal rhizotomy) selectively destroys nerve fibers associated with pain. A hollow needle is placed through the face and into an opening in the skull. Once the needle is positioned, an electrode is threaded through it to the nerve root. Then the electrode is heated until it damages the nerve fibers, creating an area of injury (lesion). If the pain isn't eliminated, additional lesions may be created. Almost everyone who undergoes radiofrequency thermal rhizotomy has some facial numbness after the procedure.

A procedure called partial trigeminal rhizotomy involves cutting part of the trigeminal nerve at the base of the brain. Through an incision behind an ear, a quarter-sized hole is made in the skull to access the nerve. Because partial trigeminal rhizotomy cuts the nerve at its source, facial numbness is a permanent side effect.

Diabetic neuropathies are neuropathic disorders that are associated with diabetes mellitus. These conditions are thought to result from diabetic microvascular injury involving small blood vessels that supply nerves (vasa nervorum) in addition to macrovascular conditions that can culminate in diabetic neuropathy. Relatively common conditions which may be associated with diabetic neuropathy include third nerve palsy; mononeuropathy; mononeuropathy multiplex; diabetic amyotrophy; a painful polyneuropathy; autonomic neuropathy; and thoracoabdominal neuropathy.

Despite advances in the understanding of the metabolic causes of neuropathy, treatments aimed at interrupting these pathological processes have been limited. Thus, with the exception of tight glucose control, treatments are for reducing pain and other symptoms.

Options for pain control include tricyclic antidepressants (TCAs), serotonin reuptake inhibitors (SSRIs), serotonin-norepinephrine reuptake inhibitors (SNRIs), and antiepileptic drugs (AEDs). A systematic review concluded that "tricyclic antidepressants and traditional anticonvulsants are better for short term pain relief than newer generation anticonvulsants." A combination of these medications (gabapentin+nortriptyline) may also be superior to a single agent.

The two drugs approved by the FDA for diabetic peripheral neuropathy are the antidepressant duloxetine and the anticonvulsant pregabalin. Before trying a systemic medication, some doctors recommend treating localized diabetic periperal neuropathy with lidocaine patches.

Postherpetic neuralgia (PHN) is a nerve pain due to damage caused by the varicella zoster virus. Typically, the neuralgia is confined to a dermatomic area of the skin and follows an outbreak of herpes zoster (HZ, commonly known as shingles) in that same dermatomic area. The neuralgia typically begins when the HZ vesicles have crusted over and begun to heal, but it can begin in the absence of HZ, in which case zoster sine herpete is presumed (see Herpes zoster).

Treatment options for PHN include antidepressants, anticonvulsants (such as gabapentin or pregabalin) and topical agents such as lidocaine patches or capsaicin lotion. Opioid analgesics may also be appropriate in many situations. There are some sporadically successful experimental treatments, such as rhizotomy (severing or damaging the affected nerve to relieve pain) and TENS (a type of electrical pulse therapy).

Neuropathic pain often seems to have no obvious cause; but, some common causes of neuropathic pain include alcoholism; amputation; back, leg, and hip problems; chemotherapy; diabetes; facial nerve problems; HIV infection or AIDS; multiple sclerosis; shingles; and spine surgery.

Symptoms may include shooting and burning pain; and tingling and numbness.

Some neuropathic pain studies suggest the use of non-steroidal anti-inflammatory drugs, such as Aleve or Motrin, may ease pain. Some people may require a stronger pain-killer, such as those containing morphine. Anticonvulsant and antidepressant drugs seem to work in some cases.

If another condition, such as diabetes, is involved, better management of that disorder may alleviate the pain.

In cases that are difficult to treat, a pain specialist may use invasive or implantable device therapies to effectively manage the pain. Electrical stimulation of the nerves involved in neuropathic pain generation may significantly control the pain symptoms.

Unfortunately, neuropathic pain often responds poorly to standard pain treatments and occasionally may get worse instead of better over time. For some people, it can lead to serious disability.

Disclosed herein, in certain embodiments, are methods of treating neuropathic pain in an individual in need thereof. In some embodiments, the neuropathic pain is trigeminal neuralgia. In some embodiments, the neuropathic pain is diabetic peripheral neuropathy. In some embodiments, the neuropathic pain is herpetic neuralgia. In some embodiments, the methods comprise administering a CSE inhibitor. In some embodiments, the methods comprise administering a CSE inhibitor in combination with a second treatment regimen. In some embodiments, the methods comprise administering a CSE inhibitor before, simultaneously with, or after a second treatment regimen.

Pain Associated with a Disease or Condition

Disclosed herein, in certain embodiments, are methods of treating pain associated with a disease or condition in an individual in need thereof. In some embodiments, the disease or condition is an autoimmune disease. In some instances, the autoimmune disease is rheumatoid arthritis. In some embodiments, the autoimmune disease is lupus. In some embodiments, the autoimmune disease is systemic lupus erythematosus. In some embodiments, the disease or condition is an inflammatory disease. In some instances, the inflammatory disease is pancreatitis, acute pancreatitis, or chronic pancreatitis. In some embodiments, the inflammatory disease is asthma. In some instances, the inflammatory disease is arthritis. In some instances, the inflammatory disease is osteoarthritis. In some instances, the inflammatory disease is gout. In some instances, the inflammatory disease is rheumatoid arthritis. In some instances, the inflammatory disease is ankylosing spondylitis. In some instances, the inflammatory disease is inflammatory bowel disease or irritable bowel syndrome. In some embodiments, the disease or condition is a cancer. In some embodiments, the cancer is a carcinoma, sarcoma, melanoma, lymphoma, or leukemia. In some embodiments, the cancer is a pancreatic cancer, lung cancer, prostate cancer, brain cancer, intestinal cancer, throat cancer, colon cancer, and breast cancer. In some instances, the disease or condition is a lung disease. In some instances, the lung disease is chronic obstructive pulmonary disease. In some instances, the lung disease is chronic bronchitis. In some embodiments, the lung disease is emphysema. In some embodiments, the methods comprise administering a CSE inhibitor. In some embodiments, the methods comprise administering a CSE inhibitor in combination with a second treatment regimen. In some embodiments, the methods comprise administering a CSE inhibitor before, simultaneously with, or after a second treatment regimen.

Acute Post-Operative Pain

Disclosed herein, in certain embodiments, are methods of preventing or reducing acute post-operative pain in an individual in need thereof. Post-operative pain (as a result of surgery) is usually considered normal. However, when poorly controlled, the pain can cause increased heart and respiratory rate, anxiety, nausea and vomiting, urinary retention, and elevated adrenalin and cortisol levels, or reduced immune response and increased risk of infection.

Uncontrolled pain is similar to uncontrolled fear in that it promotes a "fight or flight" reaction. This reaction tends to delay wound healing and increases the complication rate including infection.

Education as to the nature of the surgery or procedure is very important in order to minimize fear and anxiety pre-operatively.

The following have all been shown to reduce post-operative pain and surgical infection, and hasten wound healing use of non-steriod anti-inflammatories, such as ibuprofen preoperatively; injection of local anesthetic into the wound prior to suturing; more liberal prescription of post-operative analgesics; and use of intra- and post-operative epidural infusions for complex surgeries. Numerous studies also demonstrate the effectiveness of relaxation techniques, such as hypnosis and massage therapy in reducing post-operative pain.

Disclosed herein, in certain embodiments, are methods of preventing or reducing acute post-operative pain in an individual in need thereof. In some embodiments, the methods comprise administering a CSE inhibitor. In some embodiments, the methods comprise administering a CSE inhibitor in combination with a second treatment regimen. In some embodiments, the methods comprise administering a CSE inhibitor before, simultaneously with, or after a second treatment regimen. In some embodiments, the methods comprise administering a CSE inhibitor in combination with non-steriod anti-inflammatories. In some embodiments, the methods comprise administering a CSE inhibitor in combination with ibuprofen. In some embodiments, the methods comprise administering a CSE inhibitor in combination with a local anesthetic. In some embodiments, the methods comprise administering a CSE inhibitor in combination with an epidural infusion.

Organ Maintenance

Disclosed herein, in certain embodiments, are methods of preventing or reducing the incidence of acute kidney injury (AM) secondary to a toxic agent (e.g., cisplatin, aminoglycosides, and radiologic contrast material) in an individual in need thereof. In some embodiments, the methods comprise administering a CSE inhibitor. In some embodiments, the methods comprise administering a CSE inhibitor in combination with a second treatment regimen. In some embodiments, the methods comprise administering a CSE inhibitor before, simultaneously with, or after a second treatment regimen.

Disclosed herein, in certain embodiments, are methods of preventing multi-organ dysfunction syndrome (MODS). In some embodiments, the methods comprise administering a CSE inhibitor. In some embodiments, the methods comprise administering a CSE inhibitor in combination with a second treatment regimen. In some embodiments, the methods comprise administering a CSE inhibitor before, simultaneously with, or after a second treatment regimen.

Autoimmune Disease

Disclosed herein, in certain embodiments, are methods of treating an autoimmune disease in an individual in need thereof. Autoimmune diseases often arise from an inappropriate immune response of the body against substances and tissues normally present in the body. In other words, the immune system mistakes some part of the body as a pathogen and attacks its own cells. This may be restricted to certain organs (e.g. in autoimmune thyroiditis) or involve a particular tissue in different places (e.g. Goodpasture's disease which may affect the basement membrane in both the lung and the kidney). The treatment of autoimmune diseases is typically with immunosuppression—medication which decreases the immune response.

Examples of autoimmune diseases include, but are not limited to, acute disseminated encephalomyelitis (ADEM), Addison's disease, agammaglobulinemia, alopecia areata, amyotrophic lateral sclerosis, ankylosing spondylitis, antiphospholipid syndrome, antisynthetase syndrome, atopic allergy, atopic dermatitis, autoimmune aplastic anemia, autoimmune cardiomyopathy, autoimmune enteropathy, autoimmune hemolytic anemia, autoimmune hepatitis, autoimmune inner ear disease, autoimmune lymphoproliferative syndrome, autoimmune peripheral neuropathy, autoimmune pancreatitis, autoimmune polyendocrine syndrome, autoimmune progesterone dermatitis, autoimmune thrombocytopenic purpura, autoimmune urticaria, autoimmune uveitis, Balo disease/Balo concentric sclerosis, Behçet's disease, Berger's disease, Bickerstaffs encephalitis, Blau syndrome, Bullous pemphigoid, Castleman's disease, celiac disease, Chagas disease, chronic inflammatory demyelinating polyneuropathy, chronic recurrent multifocal osteomyelitis. chronic obstructive pulmonary disease, Churg-Strauss syndrome, cicatricial pemphigoid, Cogan syndrome, cold agglutinin disease, complement component 2 deficiency, contact dermatitis, cranial arteritis, CREST syndrome, Crohn's disease (one of two types of idiopathic inflammatory bowel disease "IBD"), Cushing's Syndrome, cutaneous leukocytoclastic angiitis, Dego's disease, Dercum's disease, dermatitis herpetiformis, dermatomyositis, diabetes mellitus type 1, diffuse cutaneous systemic sclerosis, Dressler's syndrome, drug-induced lupus, discoid lupus erythematosus, eczema, endometriosis, enthesitis-related arthritis, eosinophilic fasciitis, eosinophilic gastroenteritis, epidermolysis bullosa acquisita, erythema nodosum, erythroblastosis fetalis, essential mixed cryoglobulinemia, Evan's syndrome, fibrodysplasia ossificans progressive, fibrosing alveolitis (or idiopathic pulmonary fibrosis), gastritis, gastrointestinal pemphigoid, giant cell arteritis, glomerulonephritis, Goodpasture's syndrome, Graves' disease, Guillain-Barré syndrome (GBS), Hashimoto's encephalopathy, Hashimoto's thyroiditis. Henoch-Schonlein purpura, herpes gestationis (aka gestational pemphigoid), hidradenitis suppurativa, Hughes-Stovin syndrome, hypogammaglobulinemia, idiopathic inflammatory demyelinating diseases, idiopathic pulmonary fibrosis, idiopathic thrombocytopenic purpura, IgA nephropathy, inclusion body myositis, chronic inflammatory demyelinating polyneuropathy, interstitial cystitis, juvenile idiopathic arthritis aka juvenile rheumatoid arthritis, Kawasaki's disease, Lambert-Eaton myasthenic syndrome, leukocytoclastic vasculitis, lichen planus, lichen sclerosus, linear IgA disease (LAD), Lou Gehrig's disease (aka amyotrophic lateral sclerosis), lupoid hepatitis (aka Autoimmune hepatitis), lupus erythematosus, Majeed syndrome, Meniere's disease, microscopic polyangiitis, Miller-Fisher syndrome see Guillain-Barre Syndrome, mixed connective tissue disease, morphea, Mucha-Habermann disease (aka Pityriasis lichenoides et varioliformis acuta), multiple sclerosis, myasthenia gravis, myositis, narcolepsy, neuromyelitis optica (also devic's disease), neuromyotonia, occular cicatricial pemphigoid, opsoclonus myoclonus syndrome, Ord's thyroiditis, palindromic rheumatism, PANDAS (pediatric autoimmune neuropsychiatric disorders associated with streptococcus). paraneoplastic cerebellar degeneration, paroxysmal nocturnal hemoglobinuria (PNH), Parry Romberg syndrome, Parsonage-Turner syndrome, Pars planitis, pemphigus vulgaris, pernicious anaemia, perivenous encephalomyelitis, POEMS syndrome, polyarteritis nodosa, polymyalgia rheumatic, polymyositis, primary biliary cirrhosis, primary sclerosing cholangitis, progressive inflammatory neuropathy, psoriasis, psoriatic arthritis, pyoderma gangrenosum, pure red cell aplasia, Rasmussen's encephalitis, Raynaud phenomenon, relapsing polychondritis, Reiter's syndrome, restless leg syndrome, retroperitoneal fibrosis, rheumatoid arthritis, rheumatic fever, sarcoidosis, schizophrenia, Schmidt syndrome, Schnitzler syndrome, scleritis, scleroderma, serum sickness, Sjögren's syndrome, spondyloarthropathy, Still's disease, stiff person syndrome, subacute bacterial endocarditis (SBE), Susac's syndrome, Sweet's syndrome, Sydenham chorea, sympathetic ophthalmia, systemic lupus erythematosis, Takayasu's arteritis, temporal arteritis (also known as "giant cell arteritis"), thrombocytopenia, Tolosa-Hunt syndrome, transverse myelitis, ulcerative colitis (one of two types of idiopathic inflammatory bowel disease "ibd"), undifferentiated connective tissue disease different from mixed connective tissue disease, undifferentiated spondyloarthropathy, urticarial vasculitis, vasculitis, vitiligo, and Wegener's granulomatosis.

Disclosed herein, in certain embodiments, are methods of treating an autoimmune disease in an individual in need thereof. In some instances, the autoimmune disease is rheumatoid arthritis. In some embodiments, the autoimmune disease is lupus. In some embodiments, the autoimmune disease is systemic lupus erythematosus. In some embodiments, the methods comprise administering a CSE inhibitor. In some embodiments, the methods comprise administering a CSE inhibitor in combination with a second treatment regimen. In some embodiments, the methods comprise administering a CSE inhibitor before, simultaneously with, or after a second treatment regimen.

Inflammatory Disease

Disclosed herein, in certain embodiments, are methods of treating an inflammatory disease in an individual in need thereof. Inflammation is part of the complex biological response of vascular tissues to harmful stimuli, such as pathogens, damaged cells, or irritants. Inflammation is a protective attempt by the organism to remove the injurious stimuli and to initiate the healing process. Inflammation is not a synonym for infection, even in cases where inflammation is caused by infection. Although infection is caused by a microorganism, inflammation is one of the responses of the organism to the pathogen. However, inflammation is a stereotyped response, and therefore it is considered as a mechanism of innate immunity, as compared to adaptive immunity, which is specific for each pathogen.

Without inflammation, wounds and infections would never heal. Similarly, progressive destruction of the tissue would compromise the survival of the organism. However, chronic inflammation can also lead to a host of diseases, such as hay fever, periodontitis, atherosclerosis, rheumatoid arthritis, and even cancer (e.g., gallbladder carcinoma). It is for that reason that inflammation is normally closely regulated by the body.

Inflammation can be classified as either acute or chronic. Acute inflammation is the initial response of the body to harmful stimuli and is achieved by the increased movement of plasma and leukocytes (especially granulocytes) from the blood into the injured tissues. A cascade of biochemical events propagates and matures the inflammatory response, involving the local vascular system, the immune system, and various cells within the injured tissue. Prolonged inflammation, known as chronic inflammation, leads to a progressive shift in the type of cells present at the site of inflammation and is characterized by simultaneous destruction and healing of the tissue from the inflammatory process.

Inflammatory abnormalities are a large group of disorders which underlie a vast variety of human diseases. The immune system is often involved with inflammatory disorders, demonstrated in both allergic reactions and some myopathies, with many immune system disorders resulting in abnormal inflammation. Non-immune diseases with etiological origins in inflammatory processes include cancer, atherosclerosis, and ischaemic heart disease. A large variety of proteins are involved in inflammation, and any one of them is open to a genetic mutation which impairs or otherwise dysregulates the normal function and expression of that protein.

Examples of disorders associated with inflammation include, but are not limited to, acne vulgaris, asthma, autoimmune diseases, celiac disease, chronic prostatitis, glomerulonephritis, hypersensitivities, inflammatory bowel diseases, pelvic inflammatory disease, primary or secondary pulmonary fibrosis, chronic obstructive pulmonary disease, reperfusion injury, rheumatoid arthritis, sarcoidosis, transplant rejection, vasculitis and interstitial cystitis. Types of inflammation include, but are not limited to, appendicitis, bursitis, colitis, cystitis, dermatitis, meningitis, phlebitis, rhinitis, tendonitis, and tonsillitis Disclosed herein, in certain embodiments, are methods of treating an inflammatory disease in an individual in need thereof. In some embodiments, the disease or condition is an inflammatory disease. In some instances, the inflammatory disease is pancreatitis, acute pancreatitis, or chronic pancreatitis. In some embodiments, the inflammatory disease is asthma. In some instances, the inflammatory disease is arthritis. In some instances, the inflammatory disease is osteoarthritis. In some instances, the inflammatory disease is gout. In some instances, the inflammatory disease is rheumatoid arthritis. In some instances, the inflammatory disease is ankylosing spondylitis. In some instances, the inflammatory disease is inflammatory bowel disease or irritable bowel syndrome. In some embodiments, the inflammatory disease is system inflammatory response syndrome (SIRS). In some embodiments, the methods comprise administering a CSE inhibitor. In some embodiments, the methods comprise administering a CSE inhibitor in combination with a second treatment regimen. In some embodiments, the methods comprise administering a CSE inhibitor before, simultaneously with, or after a second treatment regimen.

Headache

Disclosed herein, in certain embodiments, are methods of treating a headache in an individual in need thereof. Disclosed herein, in certain embodiments, are methods of treating a migraine headache in an individual in need thereof. Disclosed herein, in certain embodiments, are methods of treating a simple migraine headache in an individual in need thereof. Disclosed herein, in certain embodiments, are methods of treating a complicated migraine headache in an individual in need thereof. Disclosed herein, in certain embodiments, are methods of treating a tension headache in an individual in need thereof. Disclosed herein, in certain embodiments, are methods of treating a cluster headache in an individual in need thereof. In some embodiments, the methods comprise administering a CSE inhibitor. In some embodiments, the methods comprise administering a CSE inhibitor in combination with a second treatment regimen. In some embodiments, the methods comprise administering a CSE inhibitor before, simultaneously with, or after a second treatment regimen.

Stroke

A stroke is the rapid loss of brain function(s) due to disturbance in the blood supply to the brain. In an ischemic stroke, blood supply to part of the brain is decreased, leading to dysfunction of the brain tissue in that area. Current evidence suggests that $H_2S$ promotes ischemic damage by a direct degenerative effect on cerebral neurons, although effect on cerebral blood flow may not be excluded.

Disclosed herein, in certain embodiments, are methods of treating stroke in an individual in need thereof. In some embodiments, the methods comprise administering a CSE inhibitor. In some embodiments, the methods comprise administering a CSE inhibitor in combination with a second treatment regimen. In some embodiments, the methods comprise administering a CSE inhibitor before, simultaneously with, or after a second treatment regimen.

DEFINITIONS

As used herein, the terms "treat," "treating" or "treatment," include alleviating, abating or ameliorating at least one symptom of a disease or condition, preventing additional symptoms, preventing progression of the condition, inhibiting the disease or condition, e.g., arresting the development of the disease or condition, relieving the disease or condition, causing regression of the disease or condition, relieving a condition caused by the disease or condition, or stopping the symptoms of the disease or condition. In one embodiment, treatment is prophylactic treatment. In another embodiment, treatment refers to therapeutic treatment.

As used herein, "administer" means to provide a treatment, for example to prescribe a treatment, apply a treatment, or distribute a treatment. In some instances, to administer means a medical professional prescribes a treatment which a patient applies (e.g., the patient applies a CPAP device, consumes a medication, or injects a medication). Administration of a medical treatment does not require the immediate or constant supervision of a medical professional.

"Co-administration" or the like, as used herein, are meant to encompass administration of the selected therapeutic agents to a single patient, and are intended to include treatment regimens in which the agents are administered by the same or different route of administration or at the same or different time.

The terms "effective amount" or "therapeutically effective amount," as used herein, refer to a sufficient amount of an agent or a compound being administered which will relieve to some extent one or more of the symptoms of the disease or condition being treated. The result can be reduction and/or alleviation of the signs, symptoms, or causes of a disease, or any other desired alteration of a biological system. For example, an "effective amount" for therapeutic uses is the amount of the composition comprising a compound as disclosed herein required to provide a clinically significant decrease in disease symptoms. An appropriate "effective" amount in any individual case may be determined using techniques, such as a dose escalation study.

The term "subject" or "patient" encompasses mammals and non-mammals. Examples of mammals include, but are not limited to, any member of the Mammalian class: humans, non-human primates such as chimpanzees, and other apes and monkey species; farm animals such as cattle, horses, sheep, goats, swine; domestic animals such as rabbits, dogs, and cats; laboratory animals including rodents, such as rats, mice and guinea pigs, and the like. In one embodiment, the mammal is a human.

A "tissue" comprises two or more cells. The two or more cells may have a similar function and/or function. The tissue may be a connective tissue, epithelial tissue, muscular tissue, or nervous tissue. Alternatively, the tissue is a bone, tendon (both referred to as musculoskeletal grafts), cornea, skin, heart valve, or vein.

An "organ" comprises two or more tissues. The two or more tissues may perform a specific function or group of functions. In some instances, the organ is a lung, mouth, nose, parathyroid gland, pineal gland, pituitary gland, carotid body, salivary gland, skin, gall bladder, pancreas, small intestine, stomach, spleen, spinal cord, thymus, thyroid gland, trachea, uterus, or vermiform appendix. Alternatively, the organ is an adrenal gland, appendix, brain, bladder, kidney, intestine, large intestine, small intestine, liver, heart, or muscle.

The term "CSE inhibitor" encompasses a full or partial inhibitor of CSE enzymatic activity in the synthesis of hydrogen sulfide.

"Activity of the carotid body" refers to the response of the carotid body to various signals. In some embodiments, such signals include $pCO_2$ or $pO_2$ in arterial blood. In some embodiments, such signals include presence or absence of certain gasotransmitters such as CO or $H_2S$ in the carotid body or in the vicinity of the carotid body. In some embodiments, such signals include presence or absence of certain ions such as $Ca^{2+}$ or $K^+$ ions in the carotid body or in the vicinity of the carotid body. In some embodiments, such signals include action potentials of the nerves that innervate the carotid body.

"Chemosensitivity" of the carotid body refers to the magnitude of the response of the carotid body to a known level of stimulation by chemical messengers including and not limited to $O_2$, $CO_2$, CO, and $H_2S$. Increased chemosensitivity is defined as an increased and disproportionate response to one that is observed under normal physiologic conditions to a similar stimulus.

The term "optionally substituted" or "substituted" means that the referenced group substituted with one or more additional group(s). In certain embodiments, the one or more additional group(s) are individually and independently selected from amide, ester, alkyl, cycloalkyl, heteroalkyl, aryl, heteroaryl, heteroalicyclic, hydroxy, alkoxy, aryloxy, alkylthio, arylthio, alkylsulfoxide, arylsulfoxide, ester, alkylsulfone, arylsulfone, cyano, halogen, alkoyl, alkoyloxo, isocyanato, thiocyanato, isothiocyanato, nitro, haloalkyl, haloalkoxy, fluoroalkyl, amino, alkyl-amino, dialkyl-amino, amido. In one embodiment, the referenced group is substituted with one or more halogen. In another embodiment, the referenced group is substituted with one or more alkyl.

An "alkyl" group refers to an aliphatic hydrocarbon group. Reference to an alkyl group includes "saturated alkyl" and/or "unsaturated alkyl". The alkyl group, whether saturated or unsaturated, includes branched, straight chain, or cyclic groups. By way of example only, alkyl includes methyl, ethyl, propyl, iso-propyl, n-butyl, iso-butyl, sec-butyl, t-butyl, pentyl, iso-pentyl, neo-pentyl, and hexyl. In some embodiments, alkyl groups include, but are in no way limited to, methyl, ethyl, propyl, isopropyl, butyl, isobutyl, tertiary butyl, pentyl, hexyl, ethenyl, propenyl, butenyl, cyclopropyl, cyclobutyl, cyclopentyl, cyclohexyl, and the like. A "lower alkyl" is a $C_1$-$C_6$ alkyl. A "heteroalkyl" group substitutes any one of the carbons of the alkyl group with a heteroatom having the appropriate number of hydrogen atoms attached (e.g., a $CH_2$ group to an NH group or an O group).

An "alkoxy" group refers to a (alkyl)O— group, where alkyl is as defined herein.

The term "alkylamine" refers to the —N(alkyl)$_x$H$_y$ group, wherein alkyl is as defined herein and x and y are selected from the group x=1, y=1 and x=2, y=0. When x=2, the alkyl groups, taken together with the nitrogen to which they are attached, optionally form a cyclic ring system.

An "amide" is a chemical moiety with formula C(O)NHR or NHC(O)R, where R is selected from alkyl, cycloalkyl, aryl, heteroaryl (bonded through a ring carbon) and heteroalicyclic (bonded through a ring carbon).

The term "ester" refers to a chemical moiety with formula —C(=O)OR, where R is selected from the group consisting of alkyl, cycloalkyl, aryl, heteroaryl and heteroalicyclic.

As used herein, the term "aryl" refers to an aromatic ring wherein each of the atoms forming the ring is a carbon atom. Aryl rings described herein include rings having five, six, seven, eight, nine, or more than nine carbon atoms. Aryl groups are optionally substituted. Examples of aryl groups include, but are not limited to phenyl, and naphthalenyl.

The term "cycloalkyl" refers to a monocyclic or polycyclic non-aromatic radical, wherein each of the atoms forming the ring (i.e. skeletal atoms) is a carbon atom. In various embodiments, cycloalkyls are saturated, or partially unsaturated. In some embodiments, cycloalkyls are fused with an aromatic ring. Cycloalkyl groups include groups having from 3 to 10 ring atoms. Illustrative examples of cycloalkyl groups include, but are not limited to, the following moieties:

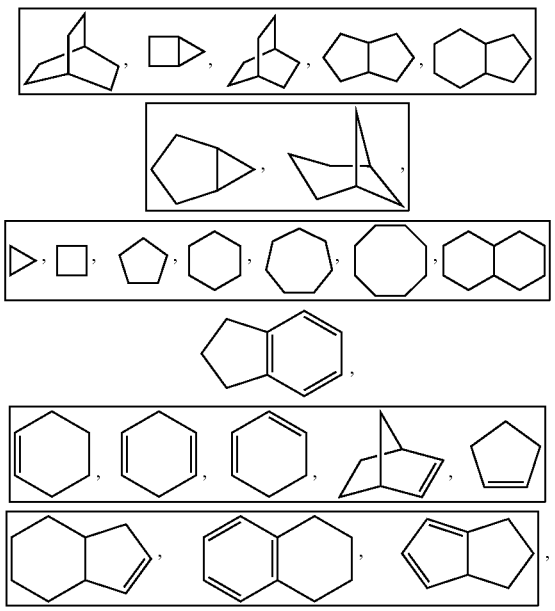

and the like. Monocyclic cycloalkyls include, but are not limited to, cyclopropyl, cyclobutyl, cyclopentyl, cyclohexyl, cycloheptyl, and cyclooctyl. Dicylclic cycloalkyls include, but are not limited to tetrahydronaphthyl, indanyl, tetrahydropentalene or the like. Polycyclic cycloalkyls include adamantane, norbornane or the like. The term cycloalkyl includes "unsaturated nonaromatic carbocyclyl" or "nonaromatic unsaturated carbocyclyl" groups both of which refer to a nonaromatic carbocycle, as defined herein, that contains at least one carbon carbon double bond or one carbon carbon triple bond.

The term "heterocyclo" refers to heteroaromatic and heteroalicyclic groups containing one to four ring heteroatoms each selected from O, S and N. In certain instances, each heterocyclic group has from 4 to 10 atoms in its ring system, and with the proviso that the ring of said group does not contain two adjacent O or S atoms. Non-aromatic heterocyclic groups include groups having 3 atoms in their ring system, but aromatic heterocyclic groups must have at least 5 atoms in their ring system. The heterocyclic groups include benzo-fused ring systems. An example of a 3-membered heterocyclic group is aziridinyl (derived from aziridine). An example of a 4-membered heterocyclic group is azetidinyl (derived from azetidine). An example of a 5-membered heterocyclic group is thiazolyl. An example of a 6-membered heterocyclic group is pyridyl, and an example of a 10-membered heterocyclic group is quinolinyl. Examples of non-aromatic heterocyclic groups are pyrrolidinyl, tetrahydrofuranyl, dihydrofuranyl, tetrahydrothienyl, tetrahydropyranyl, dihydropyranyl, tetrahydrothiopyranyl, piperidino, morpholino, thiomorpholino, thioxanyl, piperazinyl, aziridinyl, azetidinyl, oxetanyl, thietanyl, homopiperidinyl, oxepanyl, thiepanyl, oxazepinyl, diazepinyl, thiazepinyl, 1,2,3,6-tetrahydropyridinyl, 2-pyrrolinyl, 3-pyrrolinyl, indolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, pyrazolidinyl, imidazolinyl, imidazolidinyl, 3-azabicyclo[3.1.0]hexanyl, 3-azabicyclo[4.1.0]heptanyl, 3H-indolyl and quinolizinyl. Examples of aromatic heterocyclic groups are pyridinyl, imidazolyl, pyrimidinyl, pyrazolyl, triazolyl, pyrazinyl, tetrazolyl, furyl, thienyl, isoxazolyl, thiazolyl, oxazolyl, isothiazolyl, pyrrolyl, quinolinyl, isoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, oxadiazolyl, thiadiazolyl, furazanyl, benzofurazanyl, benzothiophenyl, benzothiazolyl, benzoxazolyl, quinazolinyl, quinoxalinyl, naphthyridinyl, and furopyridinyl.

The terms "heteroaryl" or, alternatively, "heteroaromatic" refers to an aryl group that includes one or more ring heteroatoms selected from nitrogen, oxygen and sulfur. An N-containing "heteroaromatic" or "heteroaryl" moiety refers to an aromatic group in which at least one of the skeletal atoms of the ring is a nitrogen atom. In certain embodiments, heteroaryl groups are monocyclic or polycyclic. Examples of monocyclic heteroaryl groups include and are not limited to:

pyrrole
(pyrrolyl)

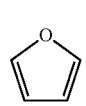
furan
(furanyl)

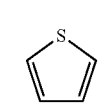
thiophene
(thiophenyl)

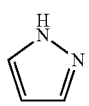
pyrazole
(pyrazolyl

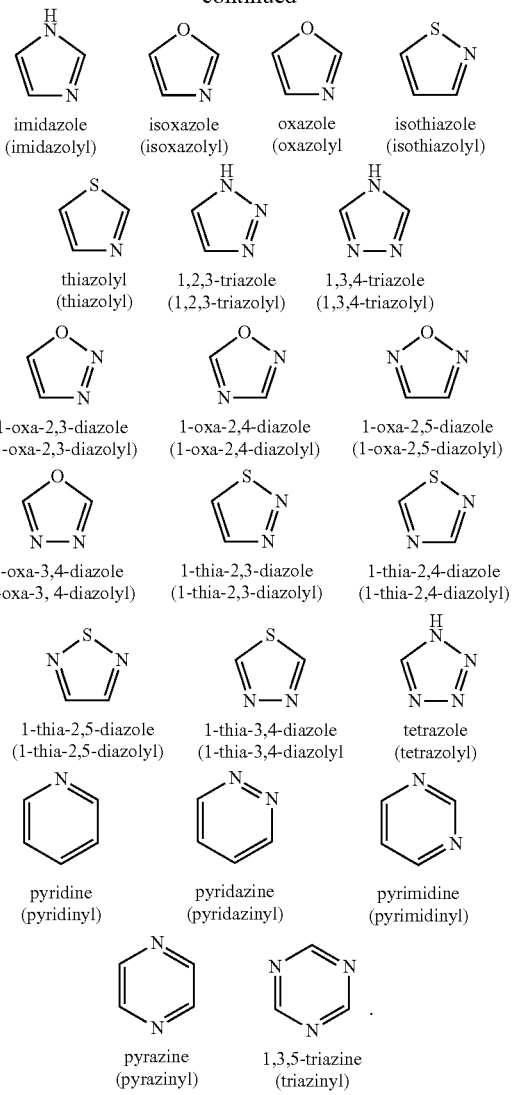

Examples of bicyclic heteroaryl groups include and are not limited to:

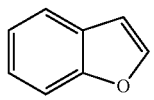
benzofuran
(benzofuranyl)

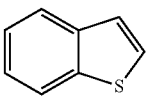
benzothiophene
(benzothiaphenyl)

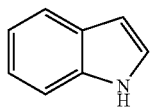
indole
(indolyl)

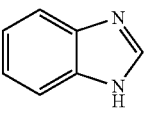
benzimidazole
(benzimidazolyl)

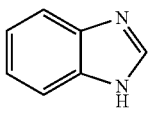
indazole
(indazolyl)

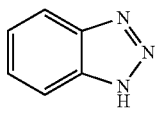
benzotriazole
(benzotriazolyl)

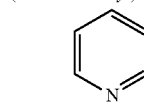
pyrrolo[2,3-b]pyridine
(pyrrolo[2,3-b]pyridinyl)

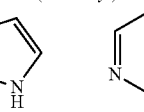
pyrrolo[2,3-c]pyridine
(pyrrolo[2,3-c]pyridinyl)

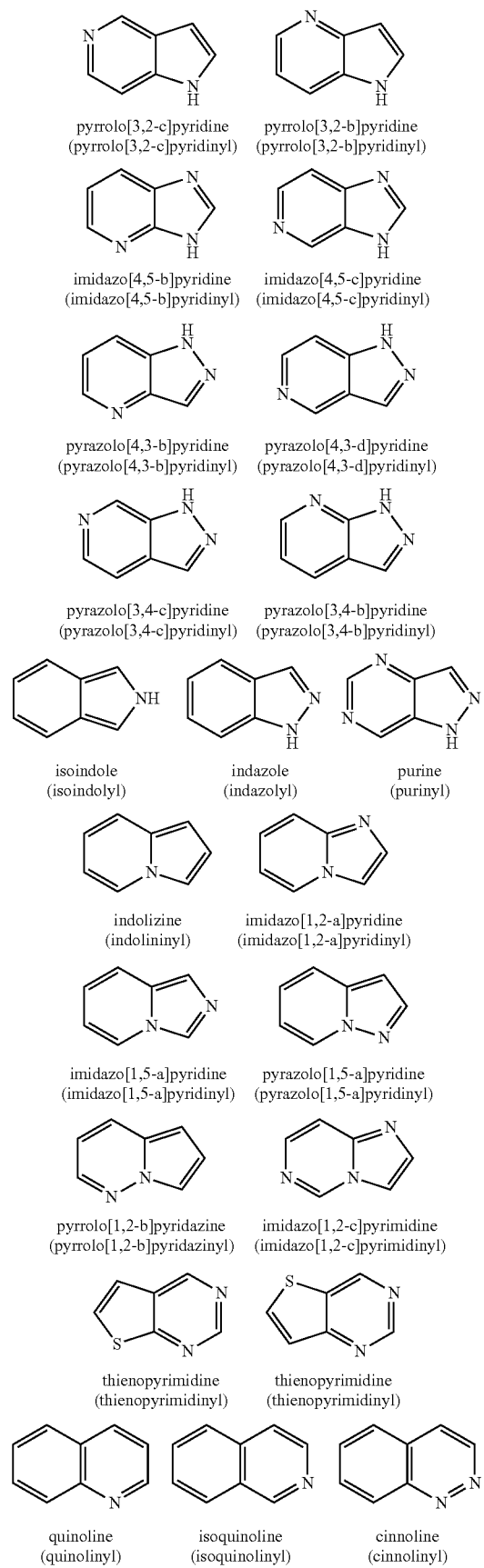
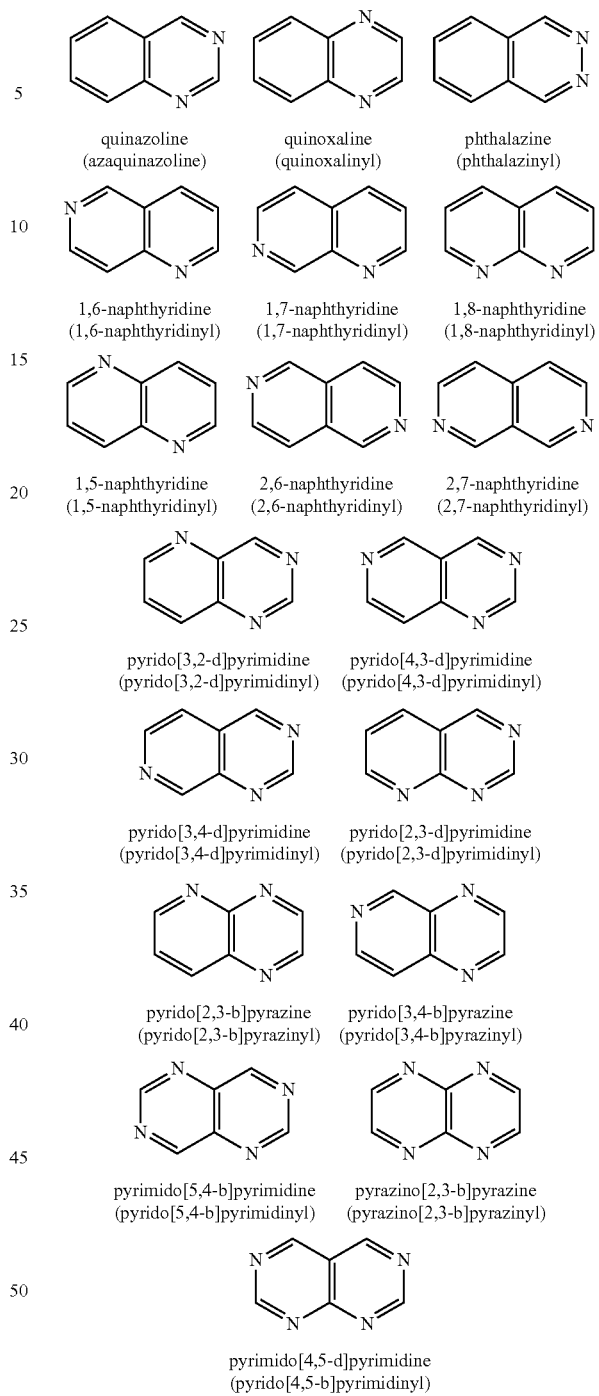

or the like.

A "heteroalicyclic" group or "heterocyclo" group or "heterocycloalkyl" group or "heterocyclyl" group refers to a cycloalkyl group, wherein at least one skeletal ring atom is a heteroatom selected from nitrogen, oxygen and sulfur. In various embodiments, heterocycloalkyls are saturated, or partially unsaturated. In some embodiments, the radicals are fused with an aryl or heteroaryl. Example of saturated heterocyloalkyl groups include

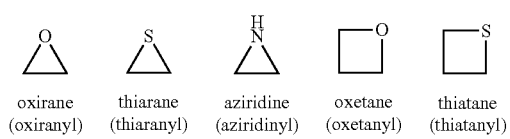
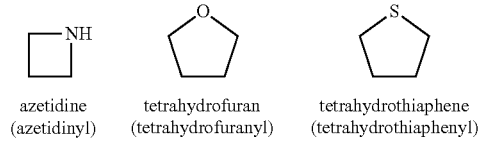
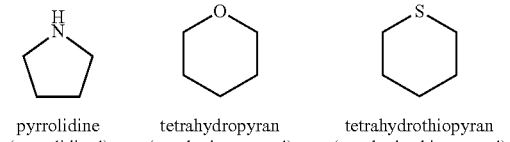
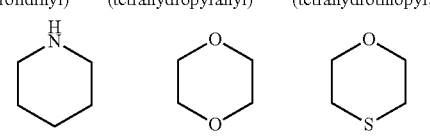
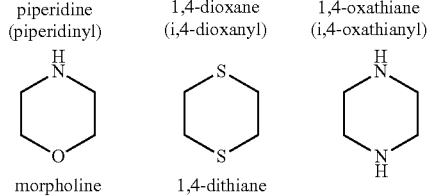
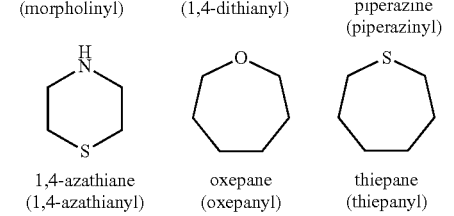
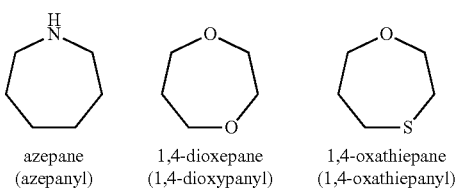
-continued
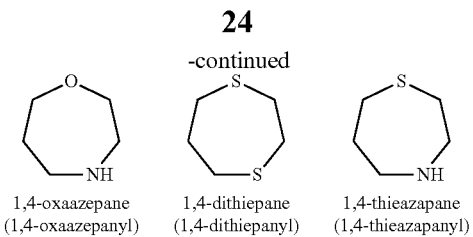
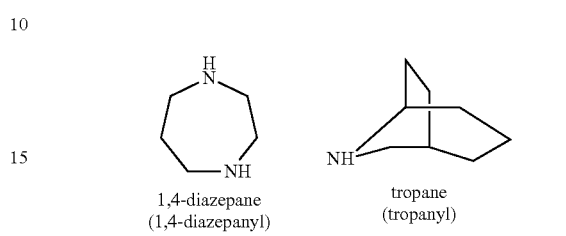
Examples of partially unsaturated heterocyclyl or heterocycloalkyl groups include
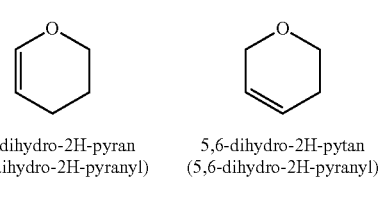
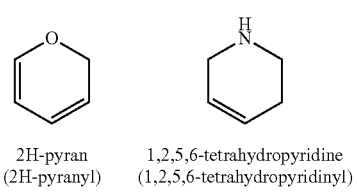
Other illustrative examples of heterocyclo or heterocycloalkyl groups, also referred to as non-aromatic heterocycles, include:
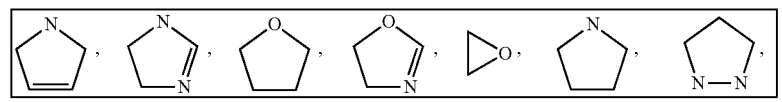
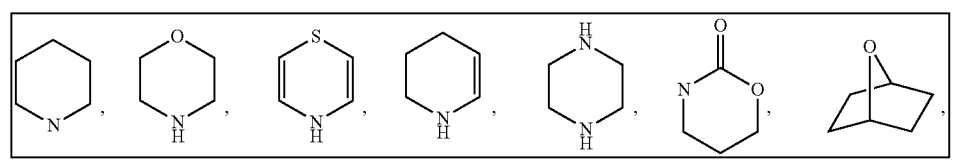
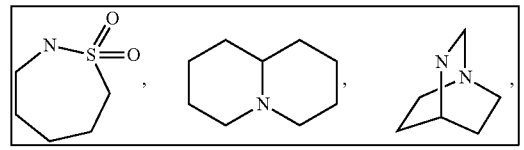

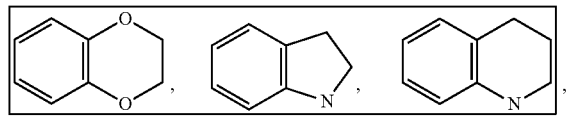, 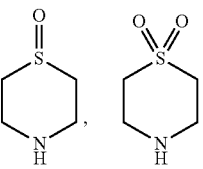

or the like.

The term heteroalicyclic also includes all ring forms of the carbohydrates, including but not limited to the monosaccharides, the disaccharides and the oligosaccharides.

The term "halo" or, alternatively, "halogen" means fluoro, chloro, bromo and iodo.

The terms "haloalkyl," and "haloalkoxy" include alkyl and alkoxy structures that are substituted with one or more halogens. In embodiments, where more than one halogen is included in the group, the halogens are the same or they are different. The terms "fluoroalkyl" and "fluoroalkoxy" include haloalkyl and haloalkoxy groups, respectively, in which the halo is fluorine.

The term "heteroalkyl" include optionally substituted alkyl, alkenyl and alkynyl radicals which have one or more skeletal chain atoms selected from an atom other than carbon, e.g., oxygen, nitrogen, sulfur, phosphorus, silicon, or combinations thereof. In certain embodiments, the heteroatom(s) is placed at any interior position of the heteroalkyl group. Examples include, but are not limited to, —CH$_2$—O—CH$_3$, —CH$_2$—CH$_2$—O—CH$_3$, —CH$_2$—NH—CH$_3$, —CH$_2$—CH$_2$—NH—CH$_3$, —CH$_2$—N(CH$_3$)—CH$_3$, —CH$_2$—CH$_2$—NH—CH$_3$, —CH$_2$—CH$_2$—N(CH$_3$)—CH$_3$, —CH$_2$—S—CH$_2$—CH$_3$, —CH$_2$—CH$_2$, —S(O)—CH$_3$, —CH$_2$—CH$_2$—S(O)$_2$—CH$_3$, —CH=CH—O—CH$_3$, —Si(CH$_3$)$_3$, —CH$_2$—CH=N—OCH$_3$, and —CH=CH—N(CH$_3$)—CH$_3$. In some embodiments, up to two heteroatoms are consecutive, such as, by way of example, —CH$_2$—NH—OCH$_3$ and —CH$_2$—O—Si(CH$_3$)$_3$.

A "cyano" group refers to a CN group.
An "isocyanato" group refers to a NCO group.
A "thiocyanato" group refers to a CNS group.
An "isothiocyanato" group refers to a NCS group.
"Alkoyloxy" refers to a RC(=O)O— group.
"Alkoyl" refers to a RC(=O)— group.

"Isosteres" of a chemical group are chemical groups that have different molecular formulae but exhibit the same or similar properties. For example, tetrazole is an isostere of carboxylic acid because it mimics the properties of carboxylic acid even though they both have very different molecular formulae. Tetrazole is one of many possible isosteric replacements for carboxylic acid. Other carboxylic acid isosteres contemplated include SO$_3$H, —SO$_2$NHR$_4$, —P(O)(OR$_4$)$_2$, —P(O)(R$_4$)(OR$_4$), —C(O)NR$_4$, —CON(R$_4$)$_2$, —CONHNHSO$_2$R$_4$, —CONHSO$_2$R$_4$, —C(R$_4$)$_2$B(OR$_5$)$_2$, and —CON(R$_4$)C(R$_4$)$_2$B(OR$_5$)$_2$; wherein each R$_4$ is independently H, OH, substituted or unsubstituted alkyl, substituted or unsubstituted heteroaryl, or substituted or unsubstituted aryl; and R$_5$ is H or C$_1$-C$_6$alkyl. In addition, carboxylic acid isosteres can include 5-7 membered carbocycles or heterocycles containing any combination of CH$_2$, O, S, or N in any chemically stable oxidation state, where any of the atoms of said ring structure are optionally substituted in one or more positions. The following structures are non-limiting examples of preferred carbocyclic and heterocyclic isosteres contemplated.

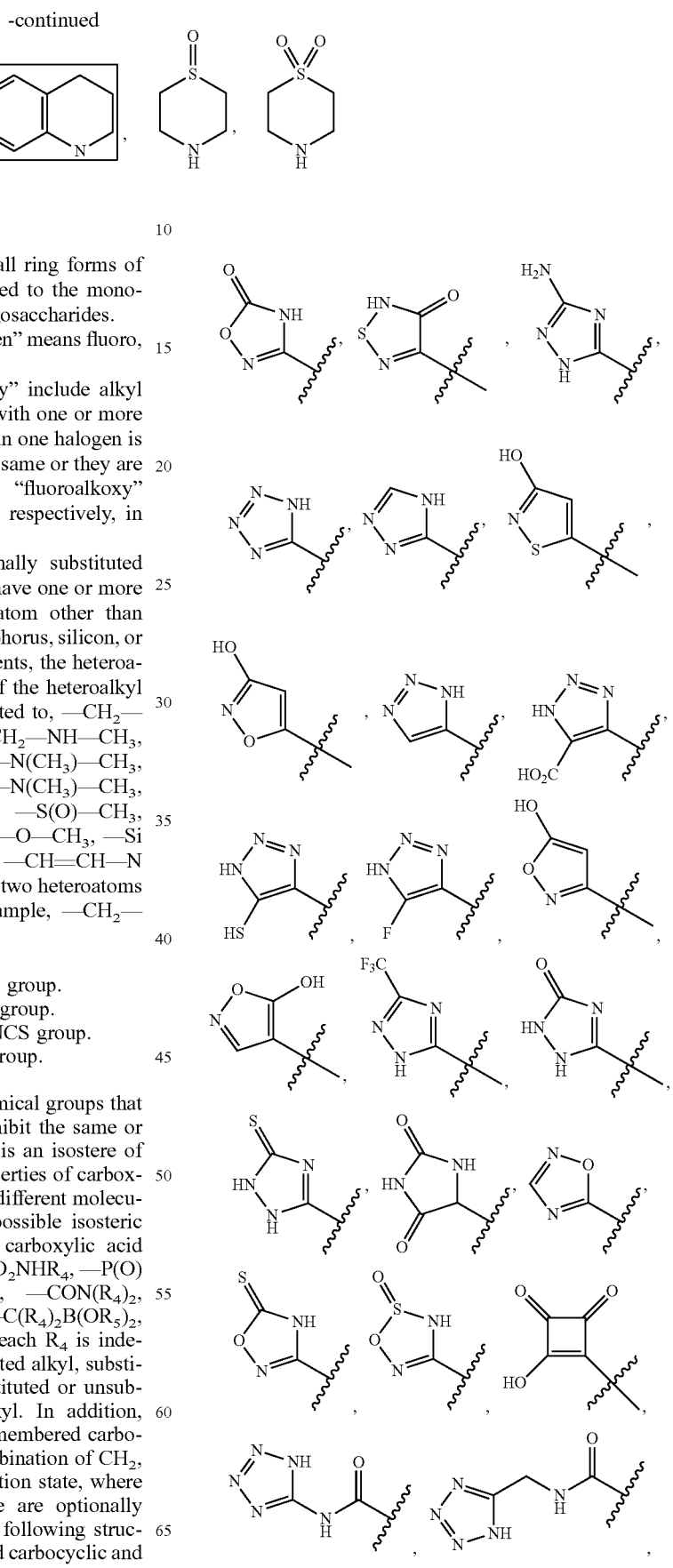

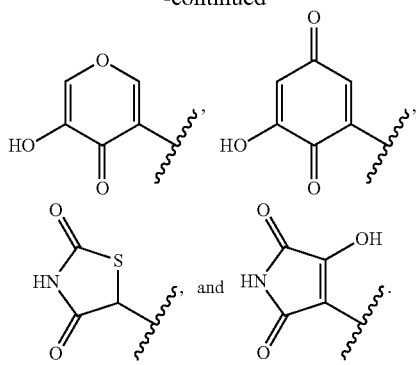

It is also contemplated that when chemical substituents are added to a carboxylic acid isostere then the inventive compound retains the properties of a carboxylic acid isostere. The present invention contemplates that when a carboxylic acid isostere is optionally substituted, then the substitution cannot eliminate the carboxylic acid isosteric properties of the inventive compound. It is contemplated that the placement of one or more substituents upon a carbocyclic or heterocyclic carboxylic acid isostere is not a substitution at one or more atom(s) which maintain(s) or is/are integral to the carboxylic acid isosteric properties of the compound, if such substituent(s) would destroy the carboxylic acid isosteric properties of the compound.

Other carboxylic acid isosteres not specifically exemplified or described in this specification are also contemplated by the present invention.

CSE Inhibitors

In the following description of CSE inhibitory compounds suitable for use in the methods described herein, definitions of referred-to standard chemistry terms may be found in reference works (if not otherwise defined herein), including Carey and Sundberg "Advanced Organic Chemistry 4th Ed." Vols. A (2000) and B (2001), Plenum Press, New York. Unless otherwise indicated, conventional methods of mass spectroscopy, NMR, HPLC, protein chemistry, biochemistry, recombinant DNA techniques and pharmacology, within the ordinary skill of the art are employed. Unless specific definitions are provided, the nomenclature employed in connection with, and the laboratory procedures and techniques of, analytical chemistry, synthetic organic chemistry, and medicinal and pharmaceutical chemistry described herein are those known in the art. Standard techniques can be used for chemical syntheses, chemical analyses, pharmaceutical preparation, formulation, and delivery, and treatment of patients.

Described herein are compounds of any of Formula (I), (II), (III), (IV), (V), or (VI). Also described herein are pharmaceutically acceptable salts, pharmaceutically acceptable solvates, and pharmaceutically acceptable prodrugs of such compounds. Pharmaceutical compositions that include at least one such compound or a pharmaceutically acceptable salt, pharmaceutically acceptable solvate, or pharmaceutically acceptable prodrug of such compound, are provided. In certain embodiments, isomers and chemically protected forms of compounds having a structure represented by any of Formula (I), (II), (III), (IV), (V), or (VI) are also provided.

In one aspect are compounds having the structure of Formula (I):

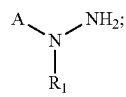

Formula (I)

wherein:

A is a carboxylic acid isostere;

$R_1$ is substituted or unsubstituted $C_3$-$C_6$alkyl, substituted or unsubstituted heteroalkyl, substituted or unsubstituted heterocycloalkyl, substituted or unsubstituted aryl, or substituted or unsubstituted heteroaryl; or a pharmaceutically acceptable salt, solvate, or prodrug thereof.

In some embodiments is a compound of Formula (I) wherein A is a carboxylic acid isostere selected from:

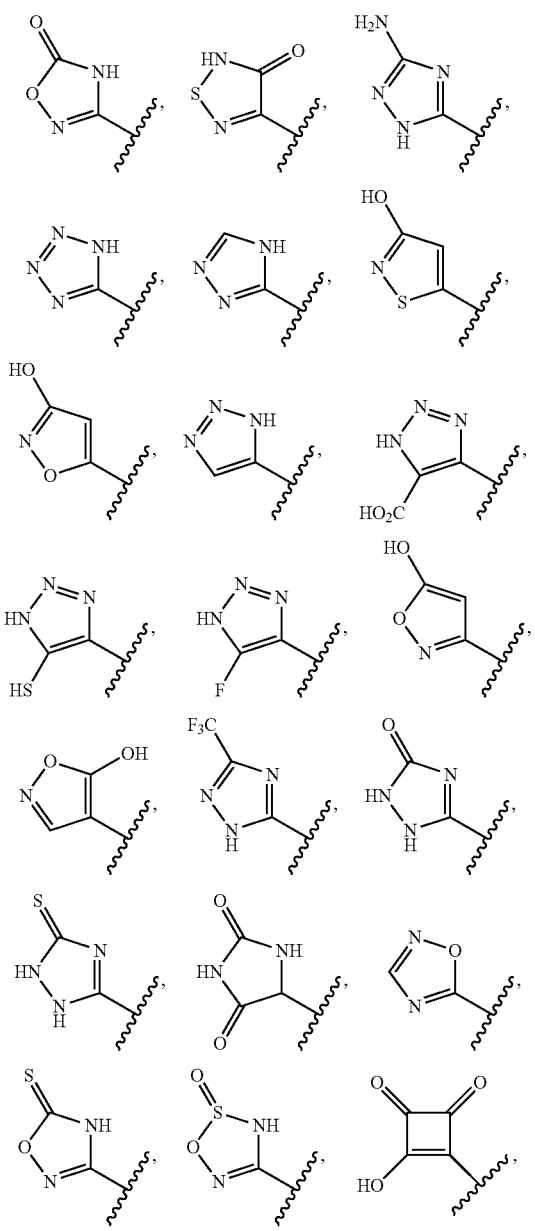

-continued

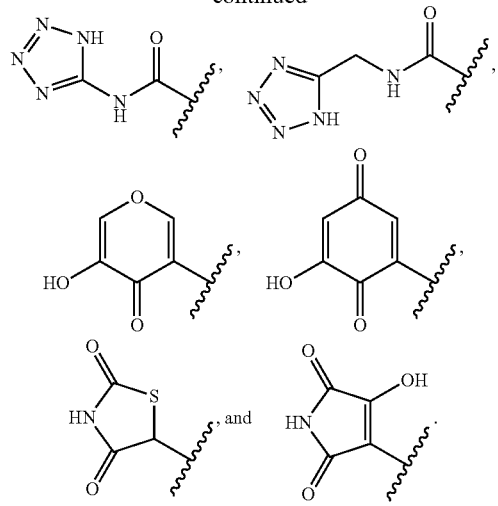

In some embodiments is a compound of Formula (I) wherein A is a carboxylic acid isostere selected from —SO₃H, —SO₂NHR₄, —P(O)(OR₄)₂, —P(O)(R₄)(OR₄), —CON(R₄)₂, —CONHNHSO₂R₄, —CONHSO₂R₄, —C(R₄)₂B(OR₅)₂, and —CON(R₄)C(R₄)₂B(OR₅)₂; wherein each $R_4$ is independently H, OH, substituted or unsubstituted alkyl, or substituted or unsubstituted aryl; and $R_5$ is H or $C_1$-$C_6$alkyl.

In some embodiments is a compound of Formula (I) wherein A is a carboxylic acid isostere selected from —SO₃H, —SO₂NHR₄, —P(O)(OR₄)₂, —P(O)(R₄)(OR₄), —C(O)R₄, —CON(R₄)₂, —CONHNHSO₂R₄, —CONHSO₂R₄, —C(R₄)₂B(OR₅)₂, and —CON(R₄)C(R₄)₂B(OR₅)₂; wherein each $R_4$ is independently H, OH, substituted or unsubstituted alkyl, substituted or unsubstituted heteroaryl, or substituted or unsubstituted aryl; and $R_5$ is H or $C_1$-$C_6$alkyl.

In another embodiment is a compound of Formula (I) wherein $R_1$ is H, substituted or unsubstituted $C_3$-$C_6$alkyl, substituted or unsubstituted heteroalkyl, substituted or unsubstituted heterocycloalkyl, substituted or unsubstituted aryl, or substituted or unsubstituted heteroaryl. In some embodiments is a compound of Formula (I) wherein $R_1$ is substituted or unsubstituted $C_3$-$C_6$alkyl. In further embodiments is a compound of Formula (I) wherein $R_1$ is propyl. In further embodiments is a compound of Formula (I) wherein $R_1$ is butyl. In some embodiments is a compound of Formula (I) wherein $R_1$ is substituted or unsubstituted heteroalkyl. In some embodiments is a compound of Formula (I) wherein $R_1$ is substituted or unsubstituted heterocycloalkyl. In some embodiments is a compound of Formula (I) wherein $R_1$ is substituted or unsubstituted aryl. In some embodiments is a compound of Formula (I) wherein $R_1$ is substituted or unsubstituted heteroaryl.

In another aspect are compounds having the structure of Formula (II):

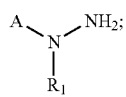

Formula (II)

wherein:

$R_1$ is H, substituted or unsubstituted alkyl, substituted or unsubstituted heteroalkyl, substituted or unsubstituted heterocycloalkyl, substituted or unsubstituted aryl, or substituted or unsubstituted heteroaryl;

A is selected from

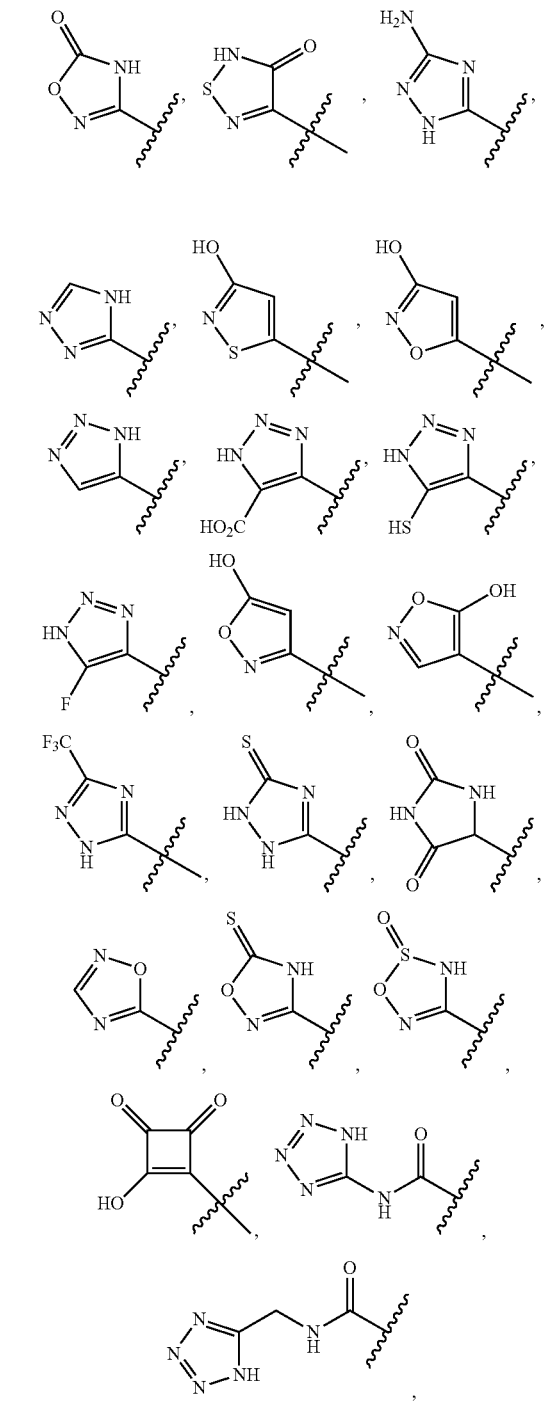

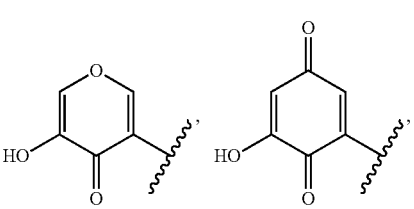

-continued

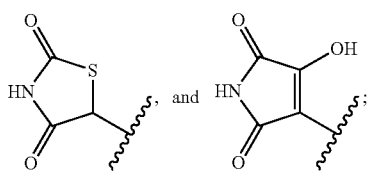

or a pharmaceutically acceptable salt, solvate, or prodrug thereof.

In some embodiments is a compound of Formula (II) wherein A is selected from

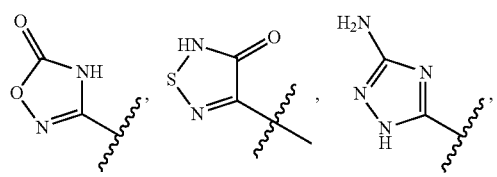

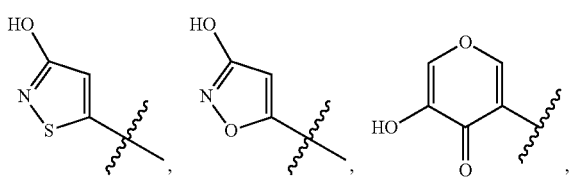

In some embodiments is a compound of Formula (II) wherein A is

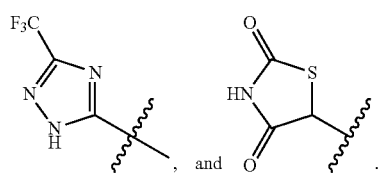

In some embodiments is a compound of Formula (II) wherein A is

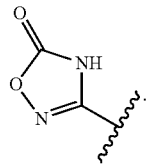

In some embodiments is a compound of Formula (II) wherein A is

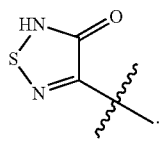 [SMILES: *c1ns[nH]c1=O]

In some embodiments is a compound of Formula (II) wherein A is

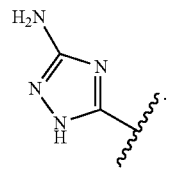

In some embodiments is a compound of Formula (II) wherein A is

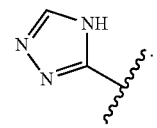

In some embodiments is a compound of Formula (II) where A is

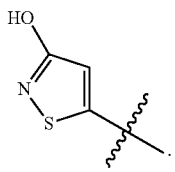

In some embodiments is a compound of Formula (II) wherein A is

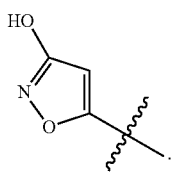

In some embodiments is a compound of Formula (II) wherein A is

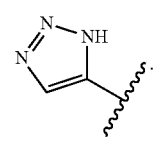

In some embodiments is a compound of Formula (II) wherein A is

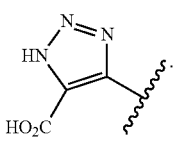

In some embodiments is a compound of Formula (II) wherein A is

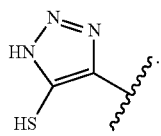

In some embodiments is a compound of Formula (II) wherein A is

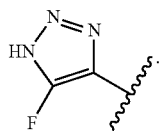

In some embodiments is a compound of Formula (II) wherein A is

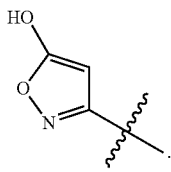

In some embodiments is a compound of Formula (II) wherein A is

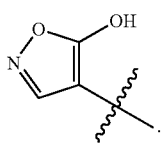

In some embodiments is a compound of Formula (II) wherein A is

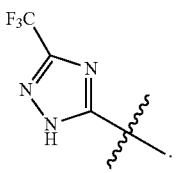

In some embodiments is a compound of Formula (II) wherein A is

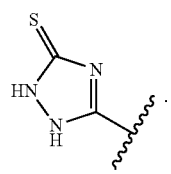 [SMILES: *c1nc(=S)[nH][nH]1]

In some embodiments is a compound of Formula (II) wherein A is

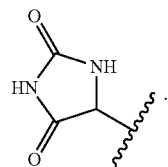

In some embodiments is a compound of Formula (II) wherein A is

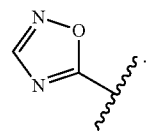

In some embodiments is a compound of Formula (II) wherein A is

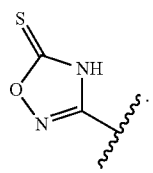 [SMILES: *c1noc(=S)[nH]1]

In some embodiments is a compound of Formula (II) wherein A is

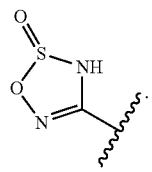

In some embodiments is a compound of Formula (II) wherein A is

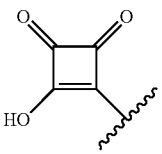

In some embodiments is a compound of Formula (II) wherein A is

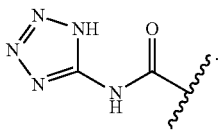 [SMILES: *C(=O)Nc1nnn[nH]1]

In some embodiments is a compound of Formula (II) wherein A is

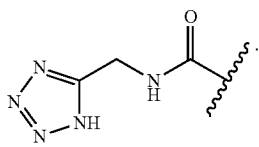 [SMILES: *C(=O)NCc1nnn[nH]1]

In some embodiments is a compound of Formula (II) wherein A is

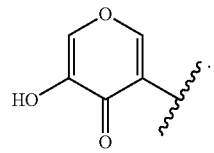

In some embodiments is a compound of Formula (II) wherein A is

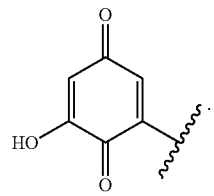 [SMILES: *C1=CC(=O)C=C(O)C1=O]

In some embodiments is a compound of Formula (II) wherein A is

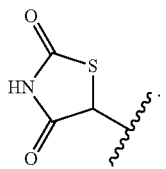

In some embodiments is a compound of Formula (II) wherein A is

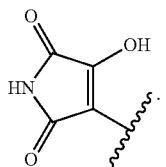

In another embodiment is a compound of Formula (II) wherein $R_1$ is H, substituted or unsubstituted alkyl, substituted or unsubstituted heteroalkyl, substituted or unsubstituted heterocycloalkyl, substituted or unsubstituted aryl, or substituted or unsubstituted heteroaryl. In some embodiments is a compound of Formula (II) wherein $R_1$ is H. In some embodiments is a compound of Formula (II) wherein $R_1$ is substituted or unsubstituted alkyl. In further embodiments is a compound of Formula (II) wherein $R_1$ is methyl. In further embodiments is a compound of Formula (II) wherein $R_1$ is ethyl. In further embodiments is a compound of Formula (II) wherein $R_1$ is propyl. In further embodiments is a compound of Formula (II) wherein $R_1$ is butyl. In some embodiments is a compound of Formula (II) wherein $R_1$ is substituted or unsubstituted heteroalkyl. In some embodiments is a compound of Formula (II) wherein $R_1$ is substituted or unsubstituted heterocycloalkyl. In some embodiments is a compound of Formula (II) wherein $R_1$ is substituted or unsubstituted aryl. In some embodiments is a compound of Formula (II) wherein $R_1$ is substituted or unsubstituted heteroaryl.

In another aspect are compounds having the structure of Formula (III):

Formula (III)

wherein:

$R_1$ is H, substituted or unsubstituted alkyl, substituted or unsubstituted heteroalkyl, substituted or unsubstituted heterocycloalkyl, substituted or unsubstituted aryl, or substituted or unsubstituted heteroaryl;

A is a carboxylic acid isostere selected from —$SO_3H$, —$SO_2NHR_4$, —$P(O)(OR_4)_2$, —$P(O)(R_4)(OR_4)$, —$CON(R_4)_2$, —$CONHNHSO_2R_4$, —$CONHSO_2R_4$, —$C(R_4)_2B(OR_5)_2$, and —$CON(R_4)C(R_4)_2B(OR_5)_2$; wherein each $R_4$ is independently H, OH, substituted or unsubstituted alkyl, or substituted or unsubstituted aryl; and $R_5$ is H or $C_1$-$C_6$alkyl; or a pharmaceutically acceptable salt, solvate, or prodrug thereof.

In another embodiment is a compound of Formula (III) wherein $R_1$ is H, substituted or unsubstituted alkyl, substituted or unsubstituted heteroalkyl, substituted or unsubstituted heterocycloalkyl, substituted or unsubstituted aryl, or substituted or unsubstituted heteroaryl. In some embodiments is a compound of Formula (III) wherein $R_1$ is H. In some embodiments is a compound of Formula (III) wherein $R_1$ is substituted or unsubstituted alkyl. In further embodiments is a compound of Formula (III) wherein $R_1$ is methyl. In further embodiments is a compound of Formula (III) wherein $R_1$ is ethyl. In further embodiments is a compound of Formula (III) wherein $R_1$ is propyl. In further embodiments is a compound of Formula (III) wherein $R_1$ is butyl. In some embodiments is a compound of Formula (III) wherein $R_1$ is substituted or unsubstituted heteroalkyl. In some embodiments is a compound of Formula (III) wherein $R_1$ is substituted or unsubstituted heterocycloalkyl. In some embodiments is a compound of Formula (III) wherein $R_1$ is substituted or unsubstituted aryl. In some embodiments is a compound of Formula (III) wherein $R_1$ is substituted or unsubstituted heteroaryl.

In another embodiment is a compound of Formula (III) wherein $R_1$ is H, and A is a carboxylic acid isostere selected from —$SO_3H$, —$SO_2NHR_4$, —$P(O)(OR_4)_2$, —$P(O)(R_4)(OR_4)$, —$CON(R_4)_2$, —$CONHNHSO_2R_4$, —$CONHSO_2R_4$, —$C(R_4)_2B(OR_5)_2$, and —$CON(R_4)C(R_4)_2B(OR_5)_2$. In another embodiment is a compound of Formula (III) wherein $R_1$ is substituted or unsubstituted alkyl, and A is a carboxylic acid isostere selected from —$SO_3H$, —$SO_2NHR_4$, —$P(O)(OR_4)_2$, —$P(O)(R_4)(OR_4)$, —$CON(R_4)_2$, —$CONHNHSO_2R_4$, —$CONHSO_2R_4$, —$C(R_4)_2B(OR_5)_2$, and —$CON(R_4)C(R_4)_2B(OR_5)_2$. In further embodiments is a compound of Formula (III) wherein $R_1$ is methyl and A is a carboxylic acid isostere selected from —$SO_3H$, —$SO_2NHR_4$, —$P(O)(OR_4)_2$, —$P(O)(R_4)(OR_4)$, —$CON $(R_4)_2$, —CONHNHSO$_2$R$_4$, —CONHSO$_2$R$_4$, —C(R$_4$)$_2$B(OR$_5$)$_2$, and —CON(R$_4$)C(R$_4$)$_2$B(OR$_5$)$_2$. In further embodiments is a compound of Formula (III) wherein R$_1$ is ethyl and A is a carboxylic acid isostere selected from —SO$_3$H, —SO$_2$NHR$_4$, —P(O)(OR$_4$)$_2$, —P(O)(R$_4$)(OR$_4$), —CON(R$_4$)$_2$, —CONHNHSO$_2$R$_4$, —CONHSO$_2$R$_4$, —C(R$_4$)$_2$B(OR$_5$)$_2$, and —CON(R$_4$)C(R$_4$)$_2$B(OR$_5$)$_2$. In some embodiments is a compound of Formula (III) wherein R$_1$ is substituted or unsubstituted heteroalkyl and A is a carboxylic acid isostere selected from —SO$_3$H, —SO$_2$NHR$_4$, —P(O)(OR$_4$)$_2$, —P(O)(R$_4$)(OR$_4$), —CON(R$_4$)$_2$, —CONHNHSO$_2$R$_4$, —CONHSO$_2$R$_4$, —C(R$_4$)$_2$B(OR$_5$)$_2$, and —CON(R$_4$)C(R$_4$)$_2$B(OR$_5$)$_2$. In some embodiments is a compound of Formula (III) wherein R$_1$ is substituted or unsubstituted heterocycloalkyl and A is a carboxylic acid isostere selected from —SO$_3$H, —SO$_2$NHR$_4$, —P(O)(OR$_4$)$_2$, —P(O)(R$_4$)(OR$_4$), —CON(R$_4$)$_2$, —CONHNHSO$_2$R$_4$, —CONHSO$_2$R$_4$, —C(R$_4$)$_2$B(OR$_5$)$_2$, and —CON(R$_4$)C(R$_4$)$_2$B(OR$_5$)$_2$. In some embodiments is a compound of Formula (III) wherein R$_1$ is substituted or unsubstituted aryl and A is a carboxylic acid isostere selected from —SO$_3$H, —SO$_2$NHR$_4$, —P(O)(OR$_4$)$_2$, —P(O)(R$_4$)(OR$_4$), —CON(R$_4$)$_2$, —CONHNHSO$_2$R$_4$, —CONHSO$_2$R$_4$, —C(R$_4$)$_2$B(OR$_5$)$_2$, and —CON(R$_4$)C(R$_4$)$_2$B(OR$_5$)$_2$. In some embodiments is a compound of Formula (III) wherein R$_1$ is substituted or unsubstituted heteroaryl and A is a carboxylic acid isostere selected from —SO$_3$H, —SO$_2$NHR$_4$, —P(O)(OR$_4$)$_2$, —P(O)(R$_4$)(OR$_4$), —CON(R$_4$)$_2$, —CONHNHSO$_2$R$_4$, —CONHSO$_2$R$_4$, —C(R$_4$)$_2$B(OR$_5$)$_2$, and —CON(R$_4$)C(R$_4$)$_2$B(OR$_5$)$_2$. In any of the aforementioned embodiments of Formula (III) is a compound of Formula (III) wherein A is —SO$_3$H. In any of the aforementioned embodiments of Formula (III) is a compound of Formula (III) wherein A is —SO$_2$NHR$_4$. In any of the aforementioned embodiments of Formula (III) is a compound of Formula (III) wherein A is —P(O)(OR$_4$)$_2$. In any of the aforementioned embodiments of Formula (III) is a compound of Formula (III) wherein A is —P(O)(R$_4$)(OR$_4$). In any of the aforementioned embodiments of Formula (III) is a compound of Formula (III) wherein A is —CON(R$_4$)$_2$. In any of the aforementioned embodiments of Formula (III) is a compound of Formula (III) wherein A is —CONHNHSO$_2$R$_4$. In any of the aforementioned embodiments of Formula (III) is a compound of Formula (III) wherein A is —CONHSO$_2$R$_4$. In any of the aforementioned embodiments of Formula (III) is a compound of Formula (III) wherein A is —C(R$_4$)$_2$B(OR$_5$)$_2$. In any of the aforementioned embodiments of Formula (III) is a compound of Formula (III) wherein A is —CON(R$_4$)C(R$_4$)$_2$B(OR$_5$)$_2$.

In another aspect are compounds having the structure of Formula (IV):

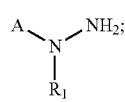

Formula (IV)

wherein:
A is

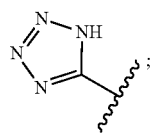

;

R$_1$ is substituted or unsubstituted C$_2$-C$_6$alkyl, substituted or unsubstituted heteroalkyl, substituted or unsubstituted heterocycloalkyl, substituted or unsubstituted aryl, or substituted or unsubstituted heteroaryl; or a pharmaceutically acceptable salt, solvate, or prodrug thereof.

In another embodiment is a compound of Formula (IV) wherein R$_1$ is substituted or unsubstituted C$_2$-C$_6$alkyl, substituted or unsubstituted heteroalkyl, substituted or unsubstituted heterocycloalkyl, substituted or unsubstituted aryl, or substituted or unsubstituted heteroaryl. In some embodiments is a compound of Formula (IV) wherein R$_1$ is substituted or unsubstituted C$_2$-C$_6$alkyl. In further embodiments is a compound of Formula (IV) wherein R$_1$ is ethyl. In further embodiments is a compound of Formula (IV) wherein R$_1$ is propyl. In further embodiments is a compound of Formula (IV) wherein R$_1$ is butyl. In some embodiments is a compound of Formula (IV) wherein R$_1$ is substituted or unsubstituted heteroalkyl. In some embodiments is a compound of Formula (IV) wherein R$_1$ is substituted or unsubstituted heterocycloalkyl. In some embodiments is a compound of Formula (IV) wherein R$_1$ is substituted or unsubstituted aryl. In some embodiments is a compound of Formula (IV) wherein R$_1$ is substituted or unsubstituted heteroaryl.

In another aspect are compounds having the structure of Formula (V):

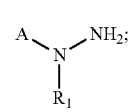

Formula (V)

wherein:
A is

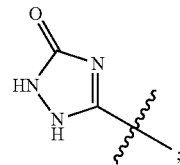 [SMILES: *c1nc(=O)[nH][nH]1]

;

R$_1$ is H, substituted or unsubstituted C$_3$-C$_6$alkyl, substituted or unsubstituted heteroalkyl, substituted or unsubstituted heterocycloalkyl, substituted or unsubstituted aryl, or substituted or unsubstituted heteroaryl; or a pharmaceutically acceptable salt, solvate, or prodrug thereof.

In another embodiment is a compound of Formula (V) wherein R$_1$ is substituted or unsubstituted C$_3$-C$_6$alkyl, substituted or unsubstituted heteroalkyl, substituted or unsubstituted heterocycloalkyl, substituted or unsubstituted aryl, or substituted or unsubstituted heteroaryl. In some embodiments is a compound of Formula (V) wherein R$_1$ is H. In some embodiments is a compound of Formula (V) wherein R$_1$ is substituted or unsubstituted C$_3$-C$_6$alkyl. In further embodiments is a compound of Formula (V) wherein R$_1$ is propyl. In further embodiments is a compound of Formula (V) wherein R$_1$ is isopropyl. In further embodiments is a compound of Formula (V) wherein R$_1$ is butyl. In some embodiments is a compound of Formula (V) wherein R$_1$ is substituted or unsubstituted heteroalkyl. In some embodiments is a compound of Formula (V) wherein R$_1$ is substituted or unsubstituted heterocycloalkyl. In some embodiments is a compound of Formula (V) wherein $R_1$ is substituted or unsubstituted aryl. In some embodiments is a compound of Formula (V) wherein $R_1$ is substituted or unsubstituted heteroaryl.

In another aspect are compounds having the structure of Formula (VI):

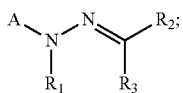
Formula (VI)

wherein:

A is a carboxylic acid isostere;

$R_1$ is H, substituted or unsubstituted alkyl, substituted or unsubstituted heteroalkyl, substituted or unsubstituted heterocycloalkyl, substituted or unsubstituted aryl, or substituted or unsubstituted heteroaryl;

$R_2$ is substituted or unsubstituted alkyl, substituted or unsubstituted heteroalkyl, substituted or unsubstituted heterocycloalkyl, substituted or unsubstituted aryl, substituted or unsubstituted heteroaryl, or —$CH_2C(O)$(substituted or unsubstituted aryl);

$R_3$ is H, or substituted or unsubstituted alkyl; or $R_2$ and $R_3$ together with the carbon atom to which they are attached form a cycloalkyl or heterocycloalkyl ring; or a pharmaceutically acceptable salt, solvate, or prodrug thereof.

In some embodiments is a compound of Formula (VI) wherein A is a carboxylic acid isostere selected from:

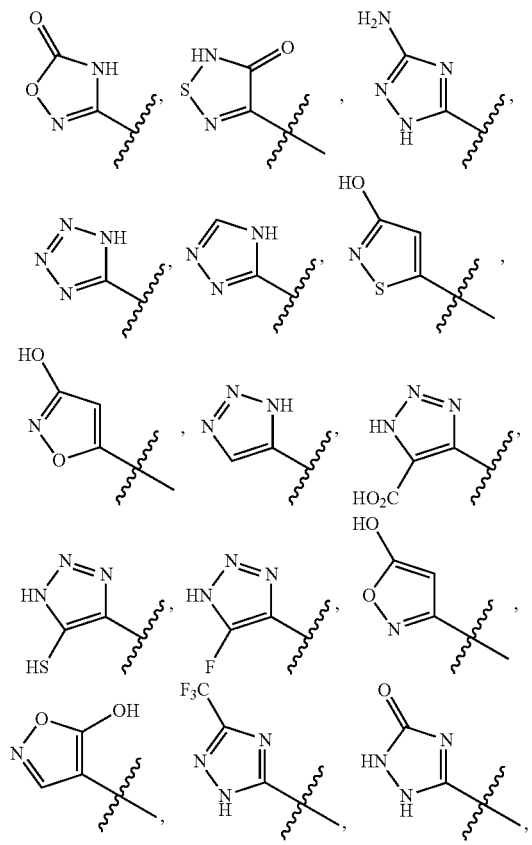

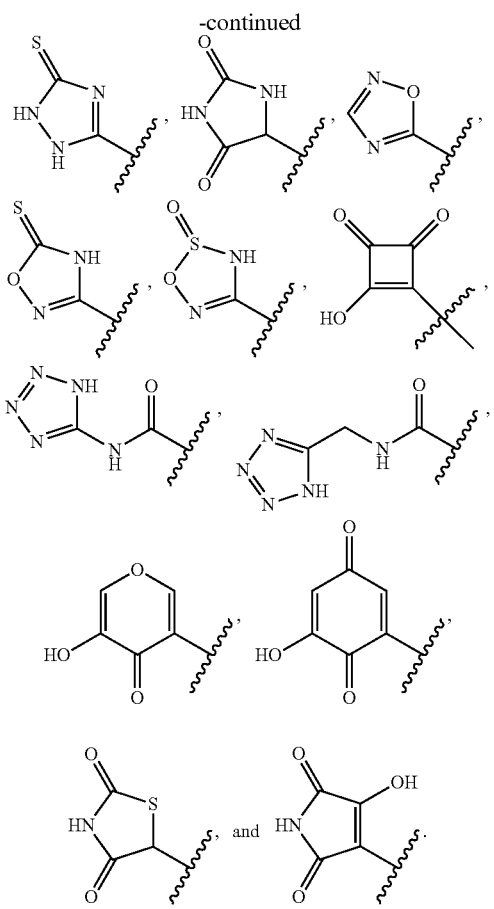

In some embodiments is a compound of Formula (VI) wherein A is a carboxylic acid isostere selected from —$SO_3H$, —$SO_2NHR_4$, —$P(O)(OR_4)_2$, —$P(O)(R_4)(OR_4)$, —$CON(R_4)_2$, —$CONHNHSO_2R_4$, —$CONHSO_2R_4$, —$C(R_4)_2B(OR_5)_2$, and —$CON(R_4)C(R_4)_2B(OR_5)_2$; wherein each $R_4$ is independently H, OH, substituted or unsubstituted alkyl, or substituted or unsubstituted aryl; and $R_5$ is H or $C_1$-$C_6$alkyl.

In some embodiments is a compound of Formula (VI) wherein A is a carboxylic acid isostere selected from —$SO_3H$, —$SO_2NHR_4$, —$P(O)(OR_4)_2$, —$P(O)(R_4)(OR_4)$, —$C(O)R_4$, —$CON(R_4)_2$, —$CONHNHSO_2R_4$, —$CONHSO_2R_4$, —$C(R_4)_2B(OR_5)_2$, and —$CON(R_4)C(R_4)_2B(OR_5)_2$; wherein each $R_4$ is independently H, OH, substituted or unsubstituted alkyl, substituted or unsubstituted heteroaryl, or substituted or unsubstituted aryl; and $R_5$ is H or $C_1$-$C_6$alkyl.

In another embodiment is a compound of Formula (VI) wherein $R_1$ is substituted or unsubstituted alkyl, substituted or unsubstituted heteroalkyl, substituted or unsubstituted heterocycloalkyl, substituted or unsubstituted aryl, or substituted or unsubstituted heteroaryl. In some embodiments is a compound of Formula (VI) wherein $R_1$ is H. In some embodiments is a compound of Formula (VI) wherein $R_1$ is substituted or unsubstituted alkyl. In further embodiments is a compound of Formula (VI) wherein $R_1$ is methyl. In further embodiments is a compound of Formula (VI) wherein $R_1$ is ethyl. In further embodiments is a compound of Formula (VI) wherein $R_1$ is propyl. In further embodiments is a compound of Formula (VI) wherein $R_1$ is butyl.

In some embodiments is a compound of Formula (VI) wherein R₁ is substituted or unsubstituted heteroalkyl. In some embodiments is a compound of Formula (VI) wherein R₁ is substituted or unsubstituted heterocycloalkyl. In some embodiments is a compound of Formula (VI) wherein R₁ is substituted or unsubstituted aryl. In some embodiments is a compound of Formula (VI) wherein R₁ is substituted or unsubstituted heteroaryl.

In some embodiments is a compound of Formula (VI) wherein R₂ is substituted or unsubstituted alkyl, substituted or unsubstituted heteroalkyl, substituted or unsubstituted heterocycloalkyl, substituted or unsubstituted aryl, substituted or unsubstituted heteroaryl, or —CH₂C(O)(substituted or unsubstituted aryl) and R₃ is H. In some embodiments is a compound of Formula (VI) wherein R₂ is substituted or unsubstituted alkyl, substituted or unsubstituted heteroalkyl, substituted or unsubstituted heterocycloalkyl, substituted or unsubstituted aryl, substituted or unsubstituted heteroaryl, or —CH₂C(O)(substituted or unsubstituted aryl) and R₃ is substituted or unsubstituted alkyl. In some embodiments is a compound of Formula (VI) wherein R₂ and R₃ together with the carbon atom to which they are attached form a cycloalkyl ring. In some embodiments is a compound of Formula (VI) wherein R₂ and R₃ together with the carbon atom to which they are attached form a heterocycloalkyl ring.

In some embodiments is a compound selected from:

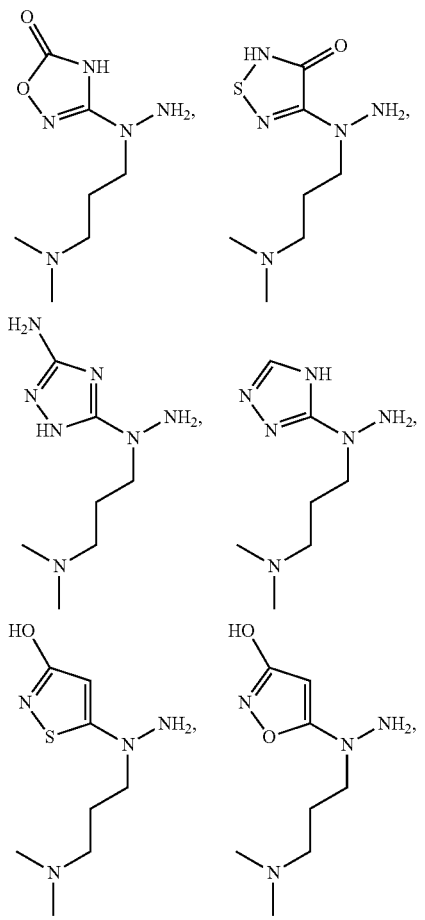

-continued

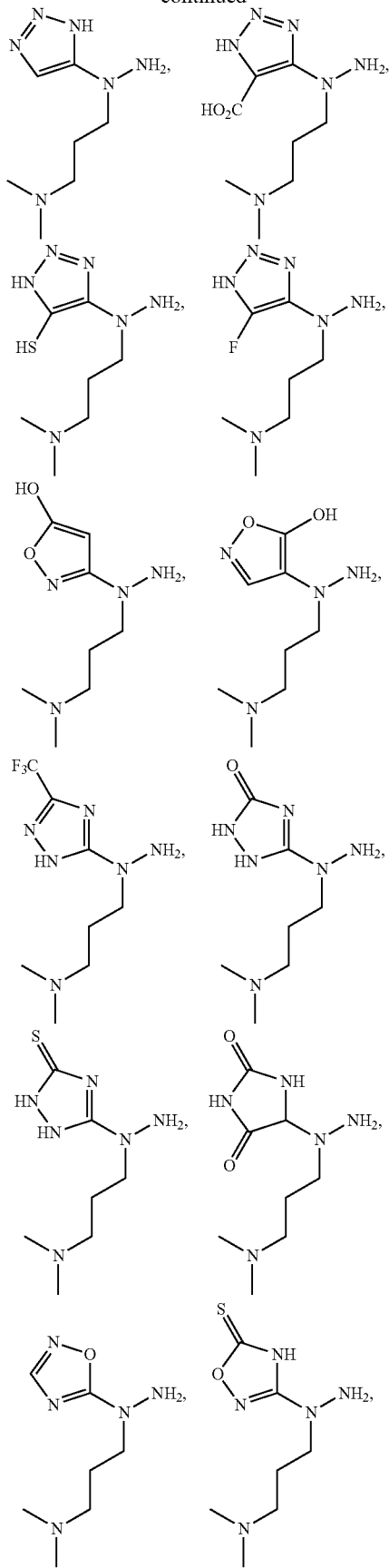

-continued
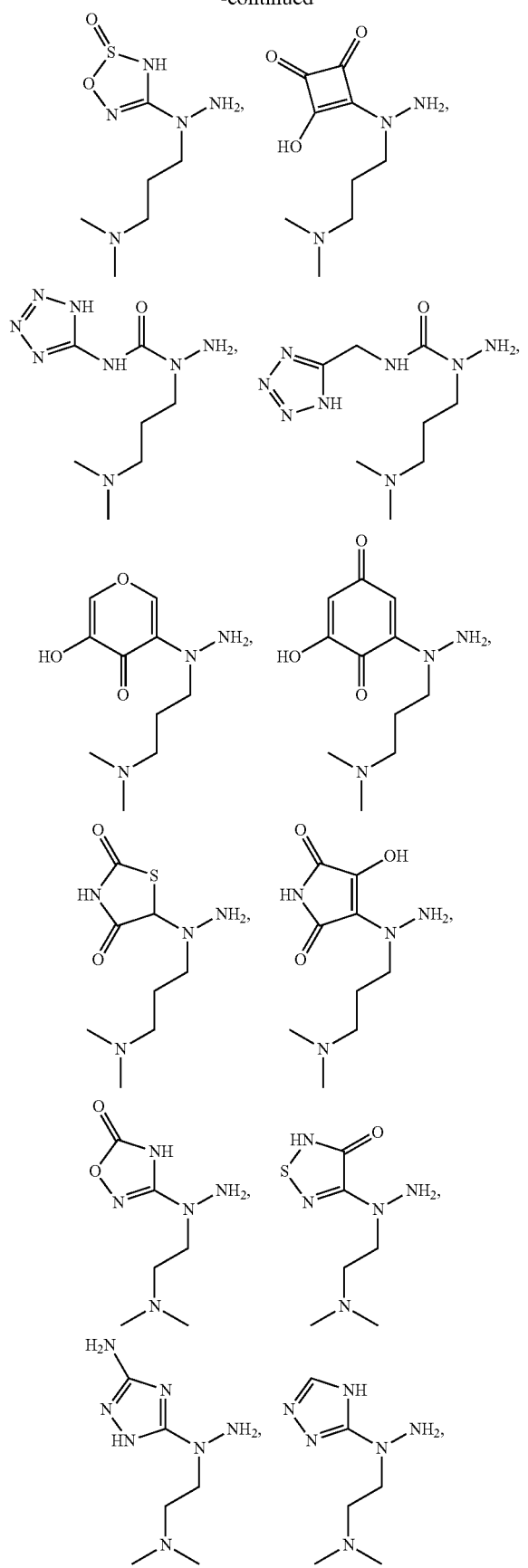
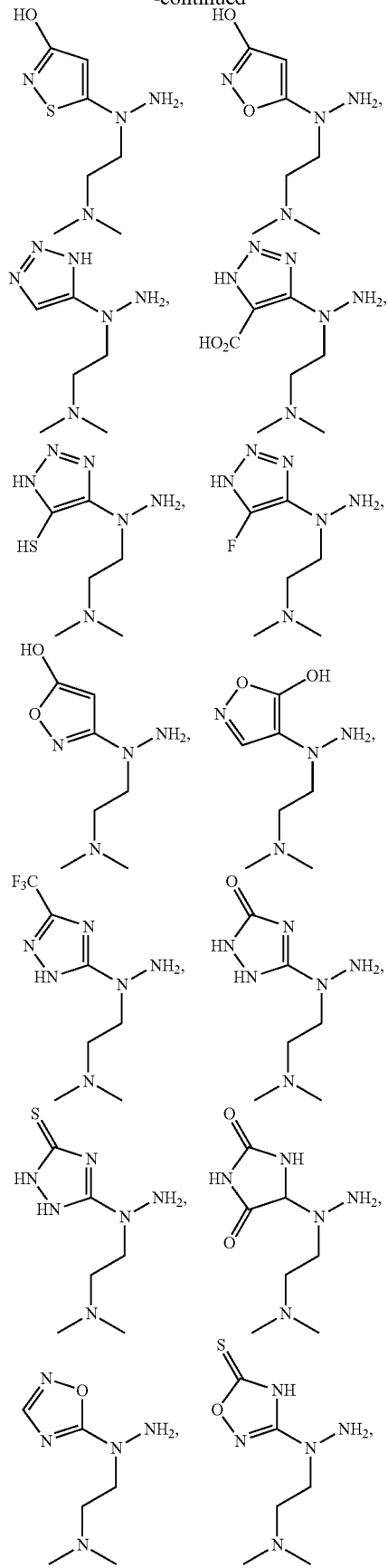

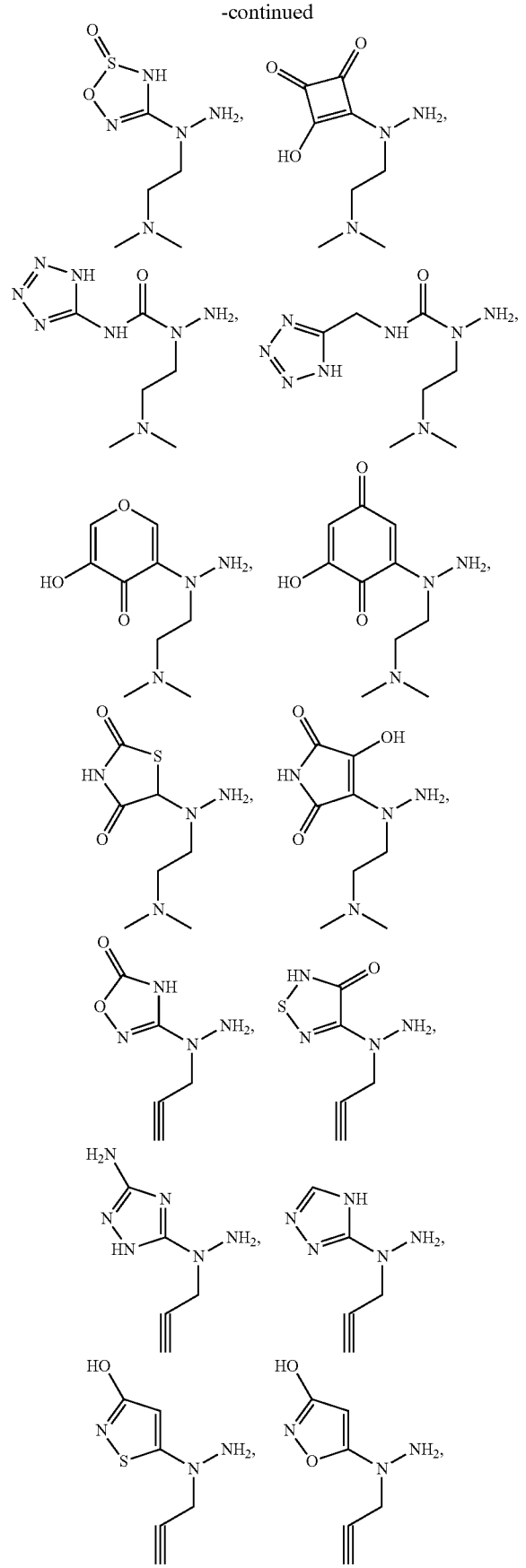
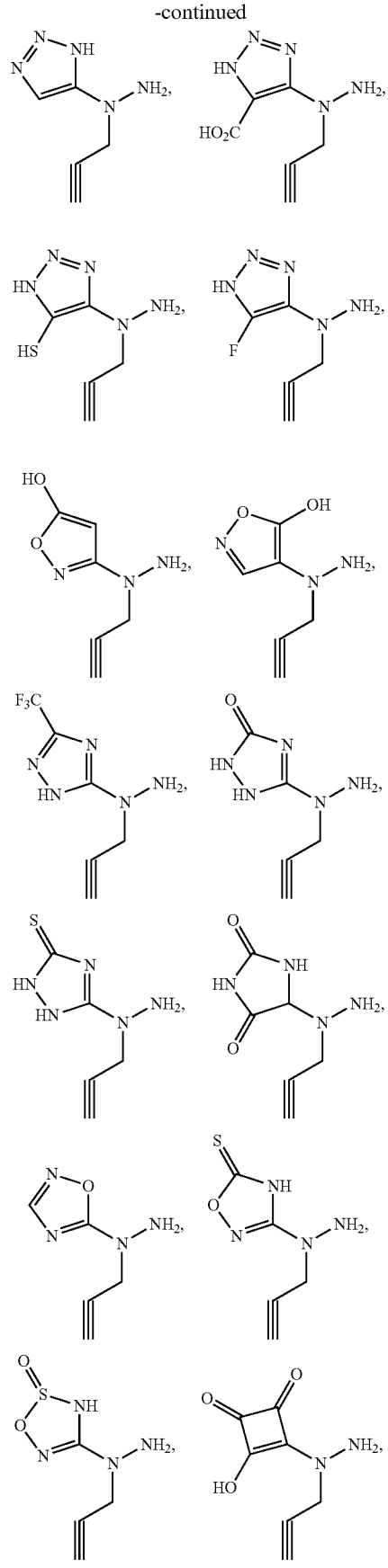

-continued
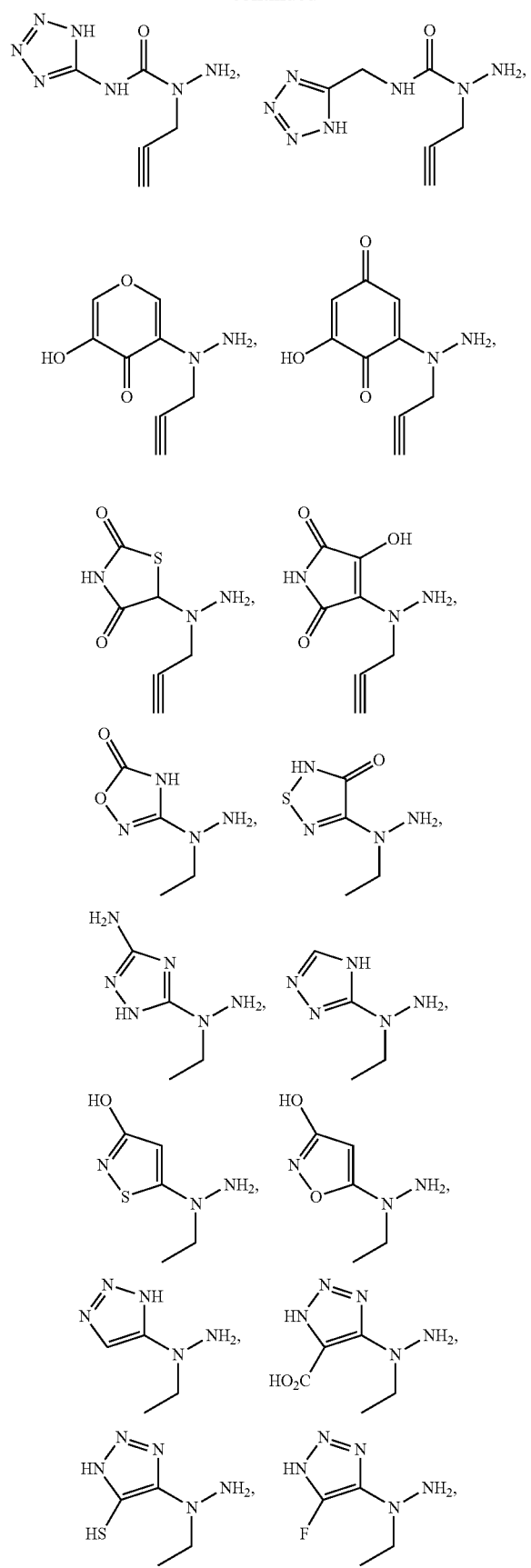
-continued
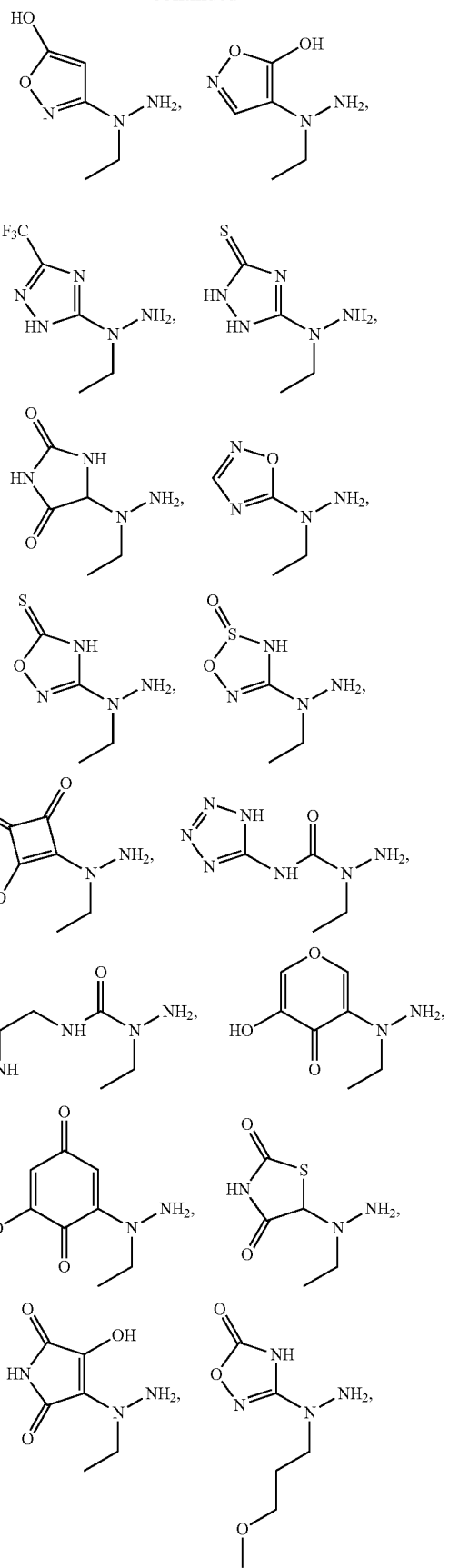

-continued

51
-continued
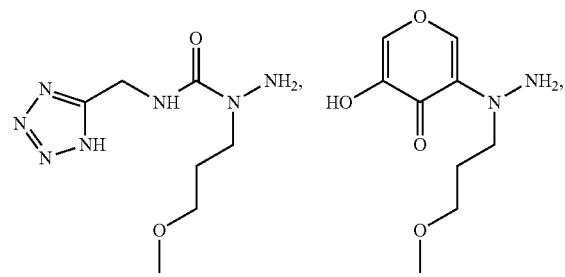
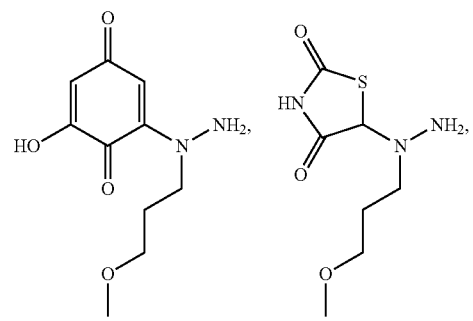
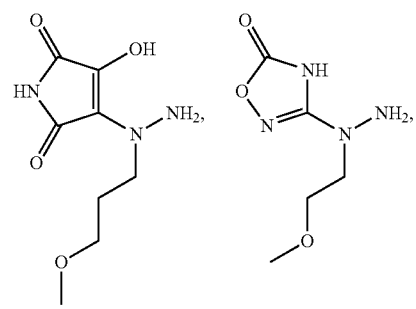
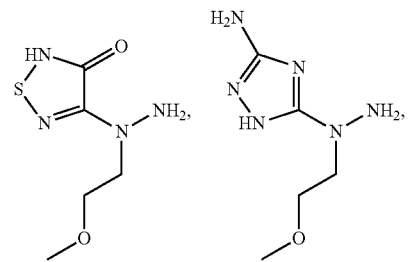
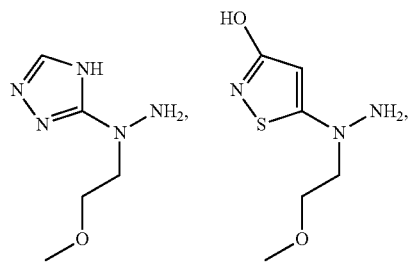
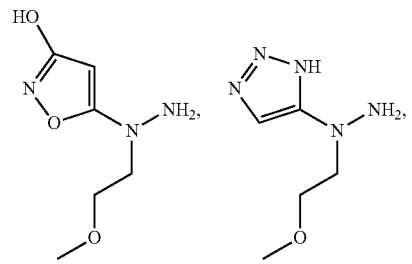
52
-continued
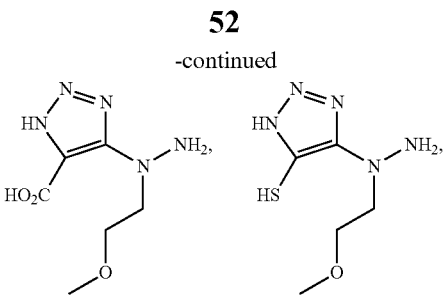
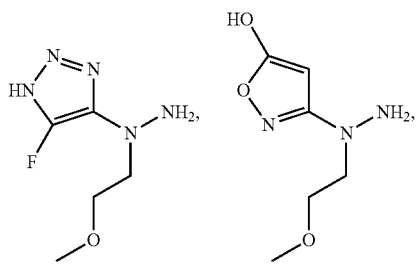
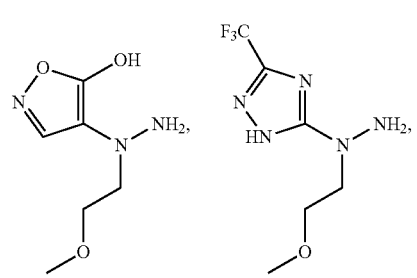
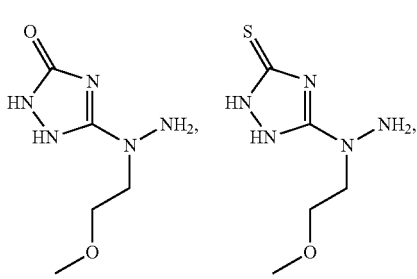
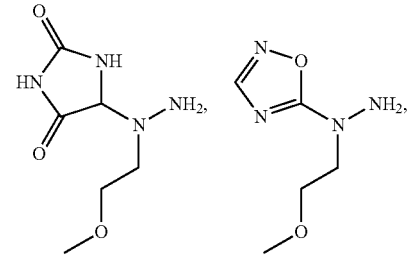
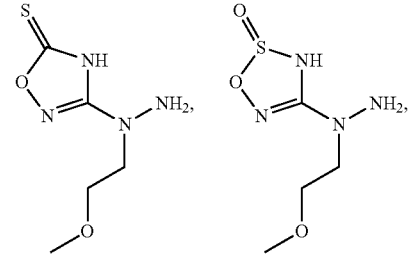

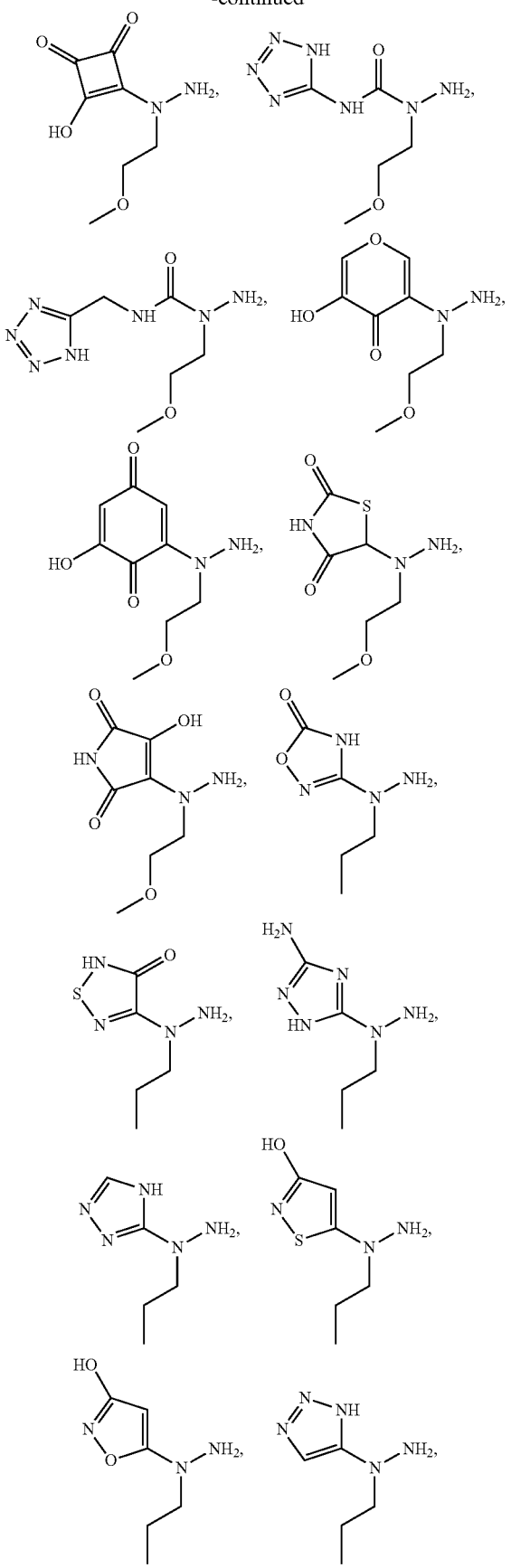
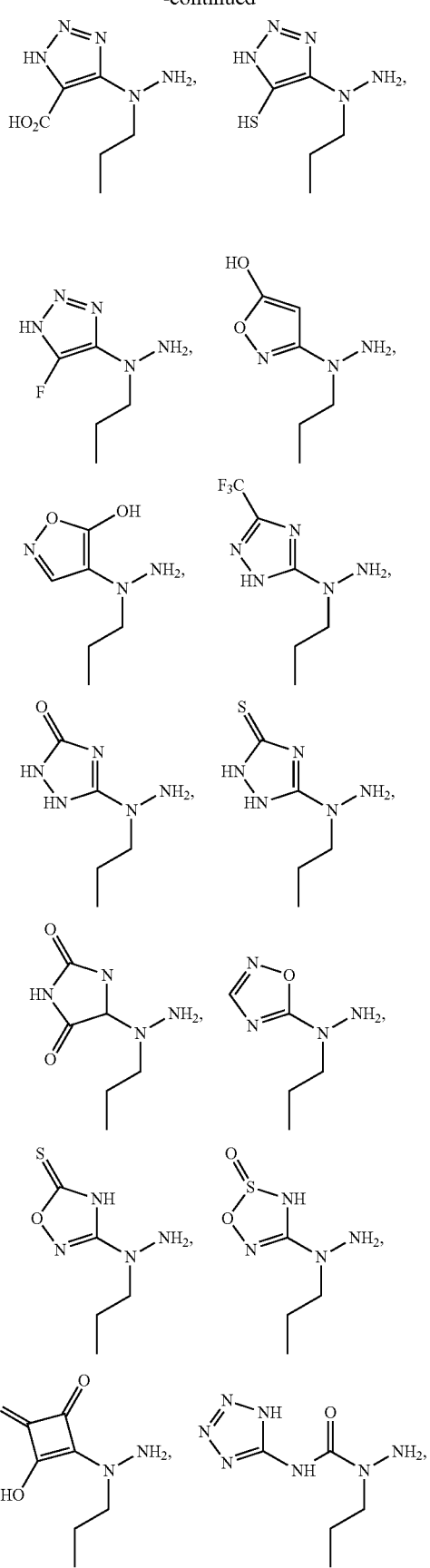

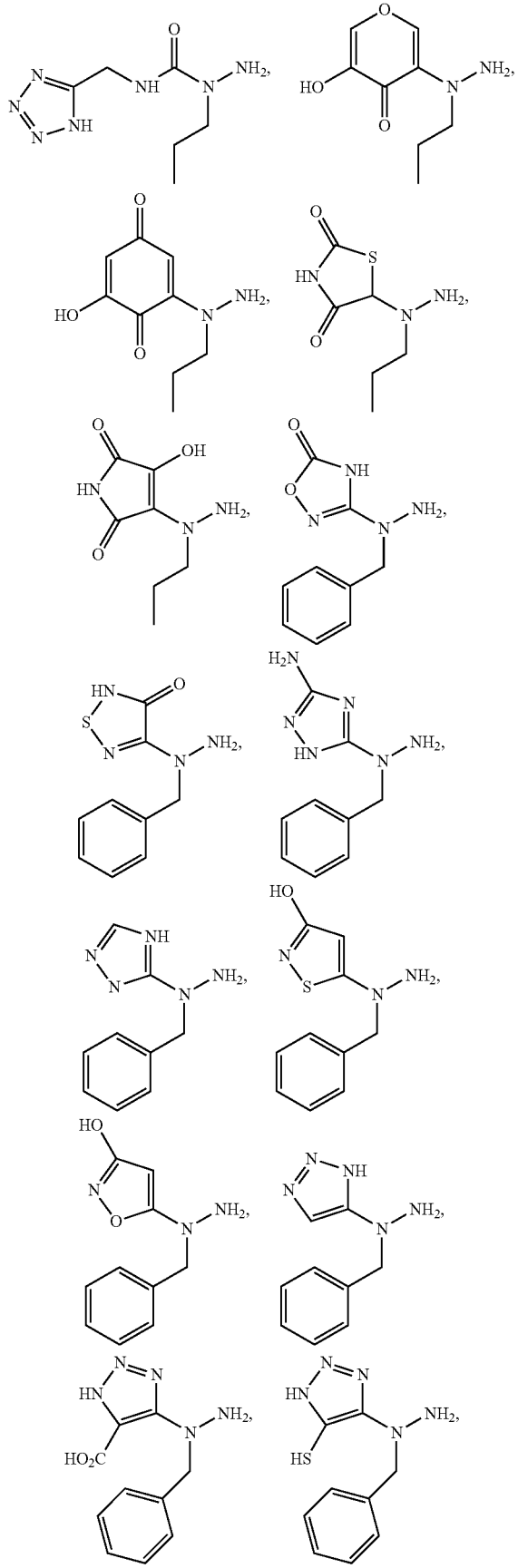
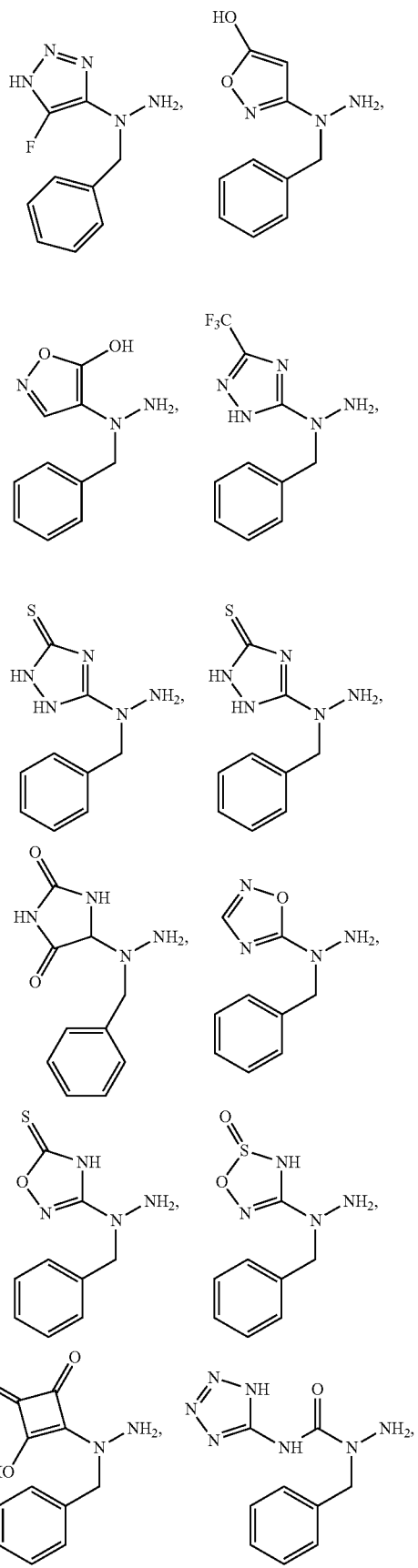

57
-continued
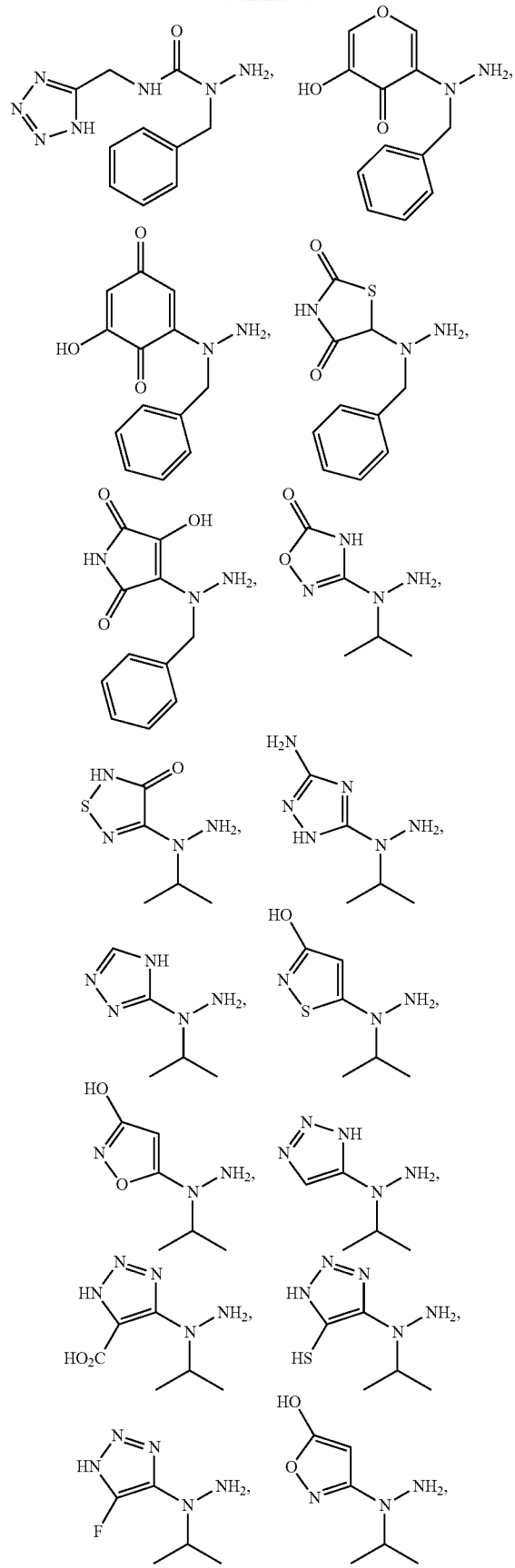
58
-continued
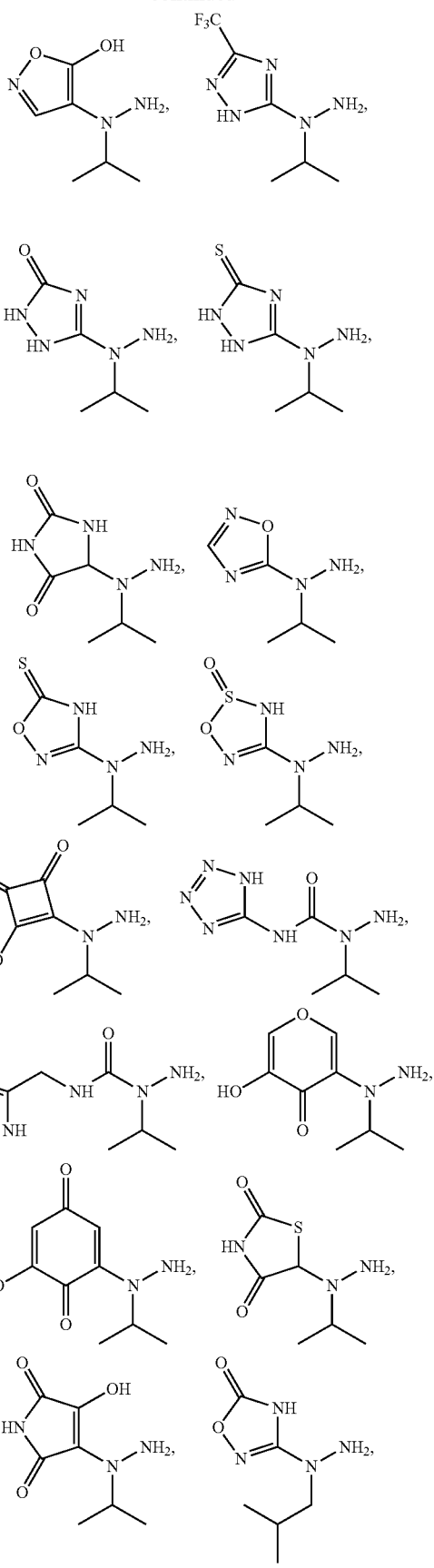

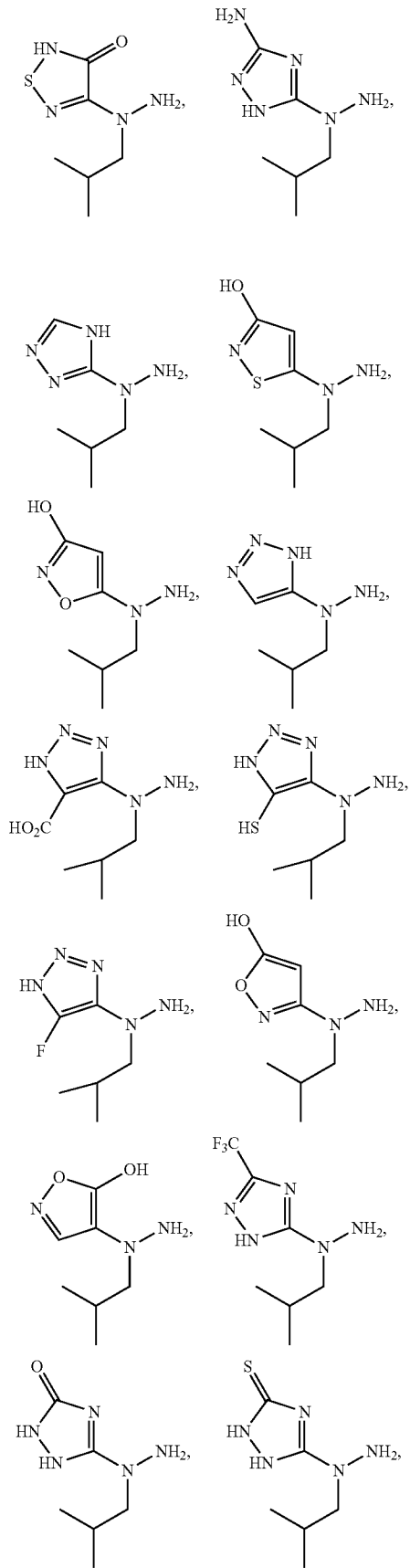
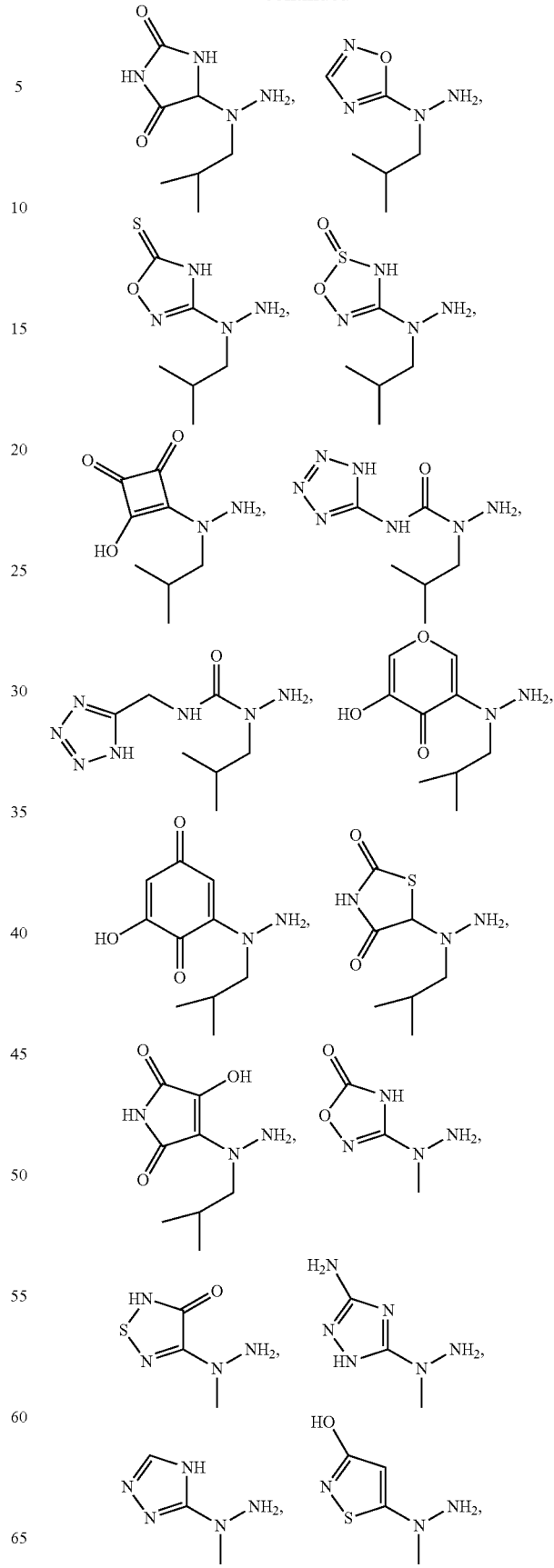

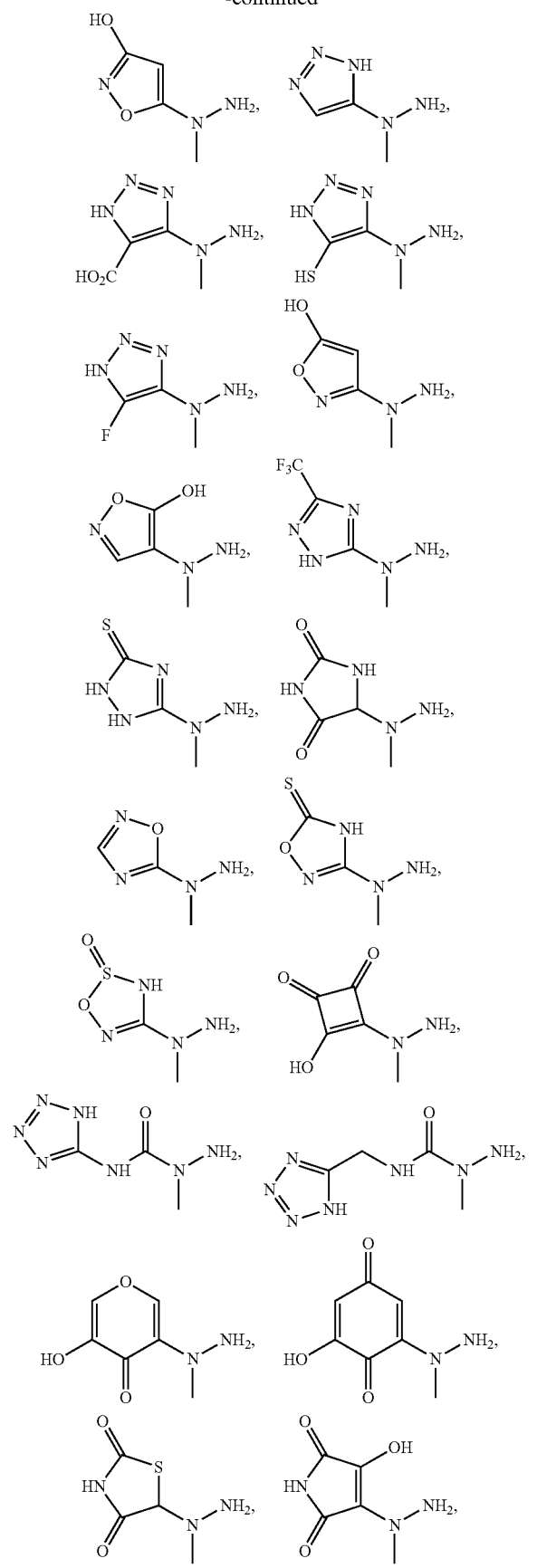
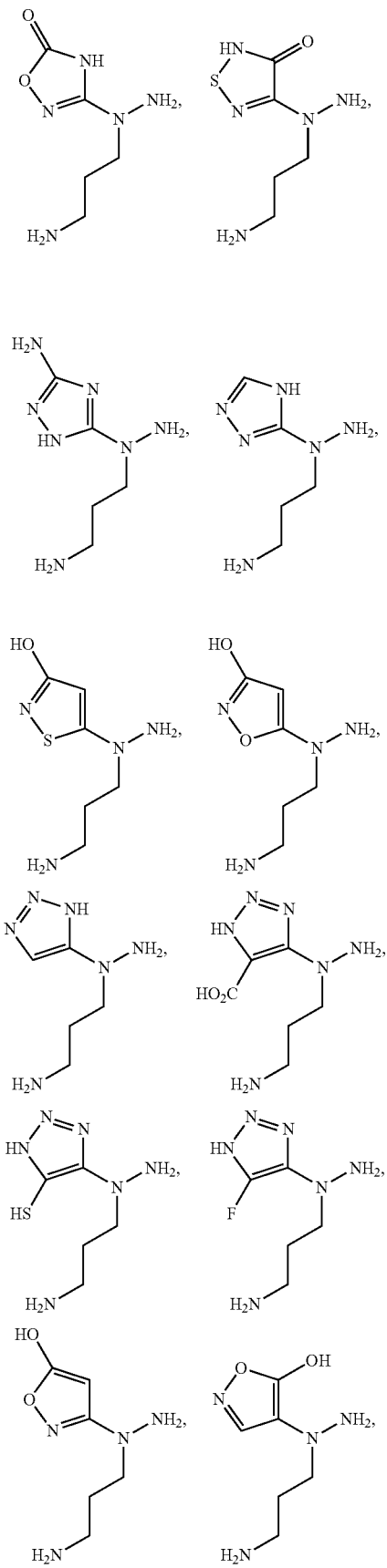

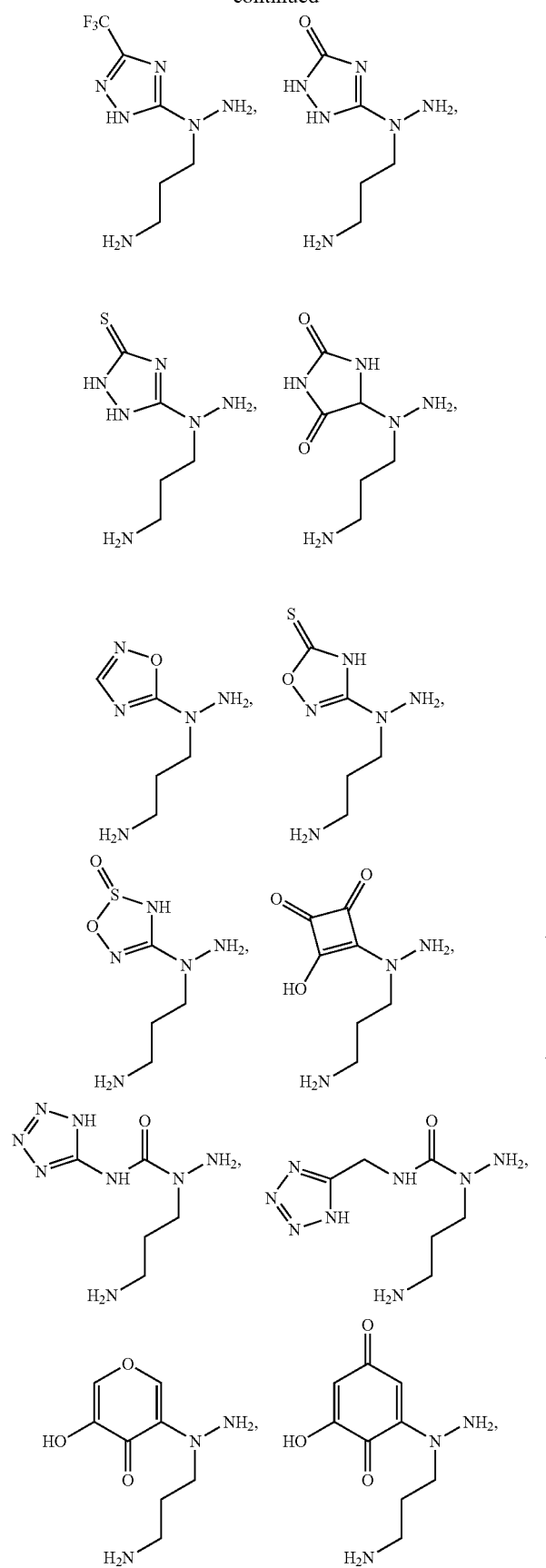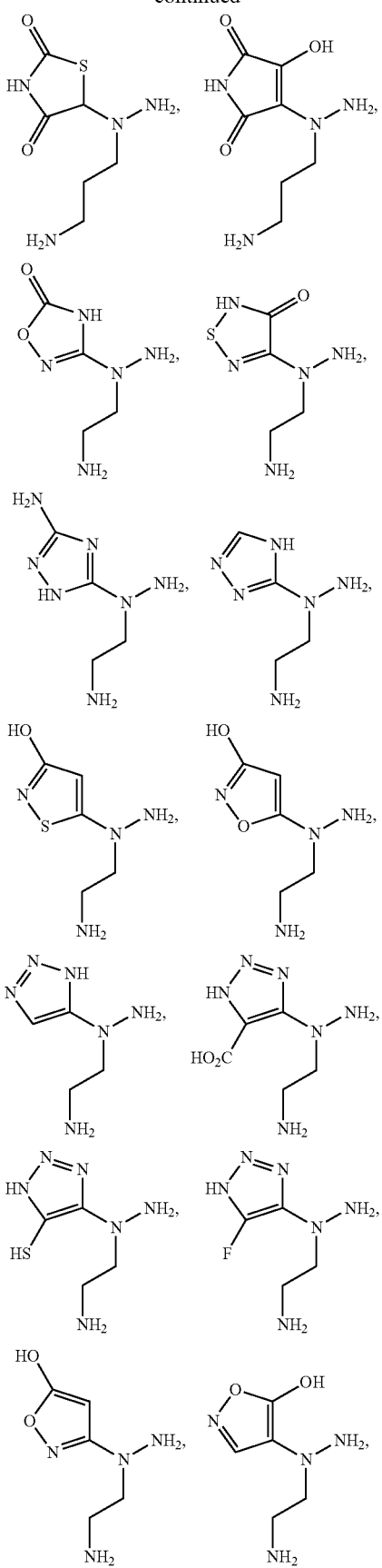

65
-continued
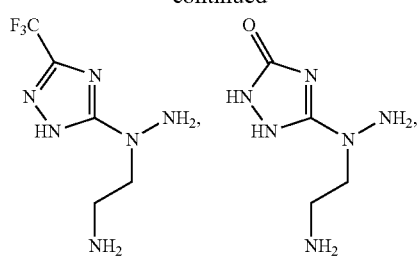
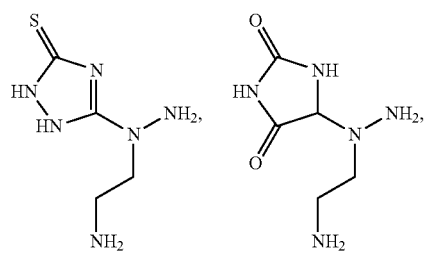
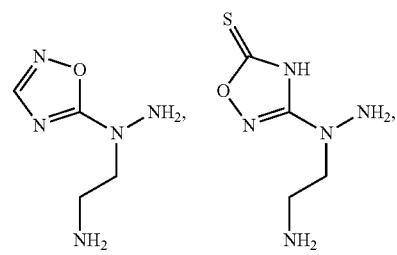
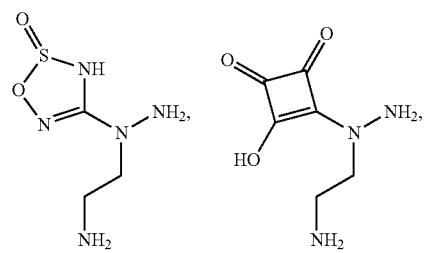
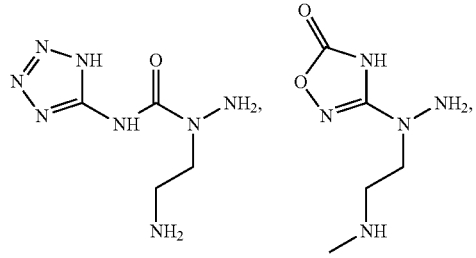
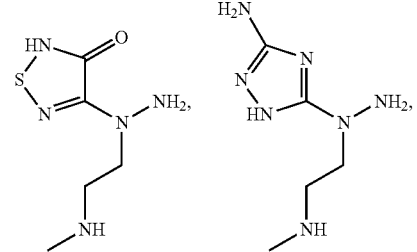
66
-continued
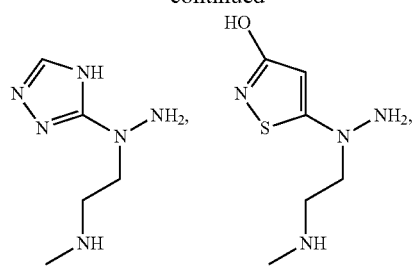
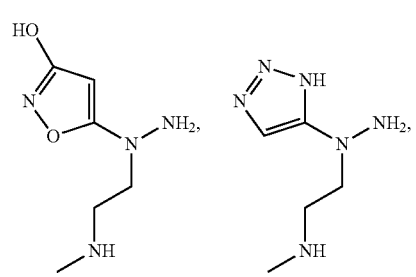
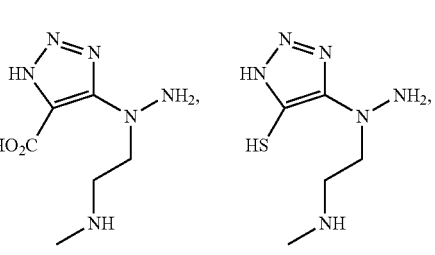
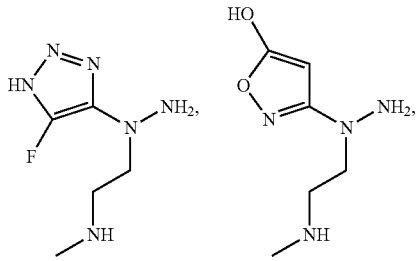
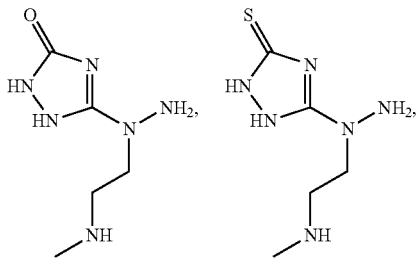

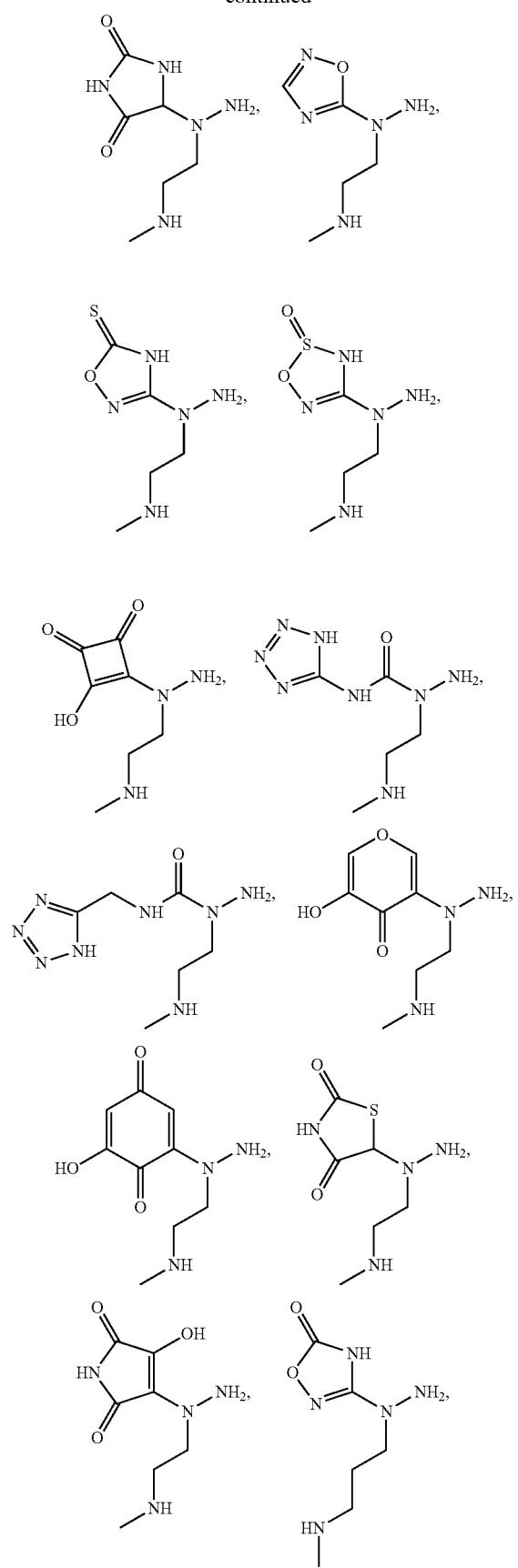
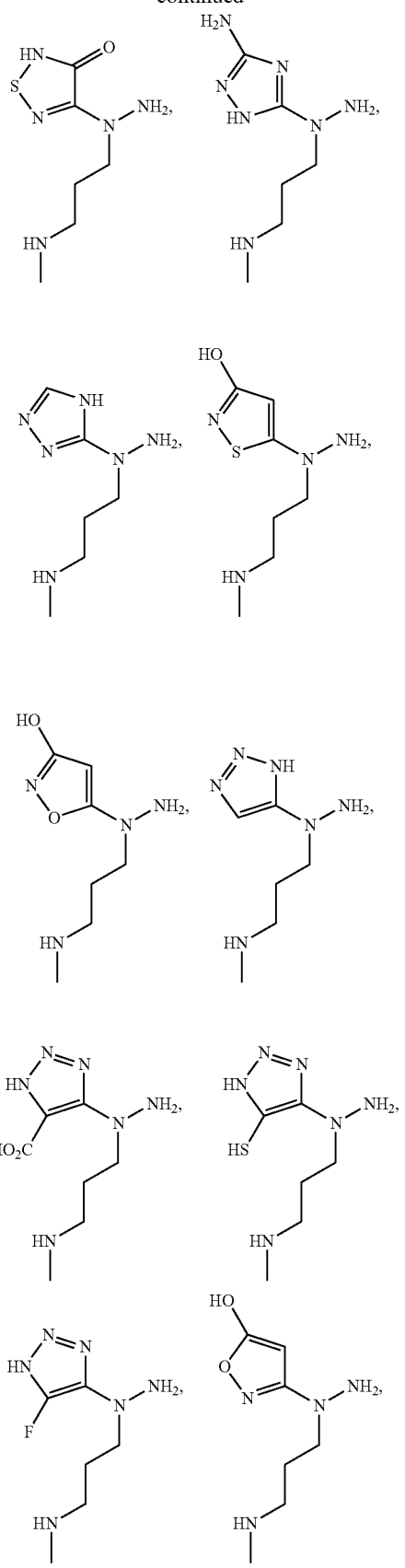

-continued
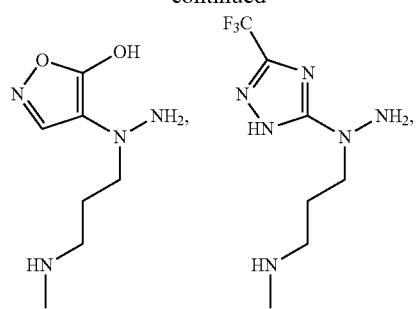
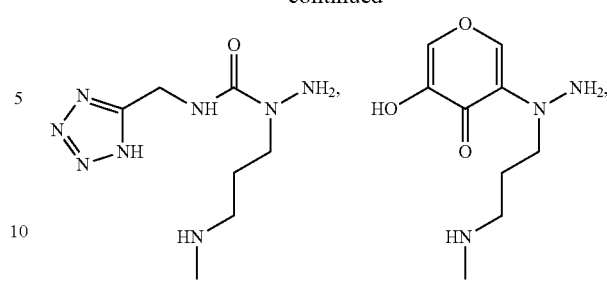
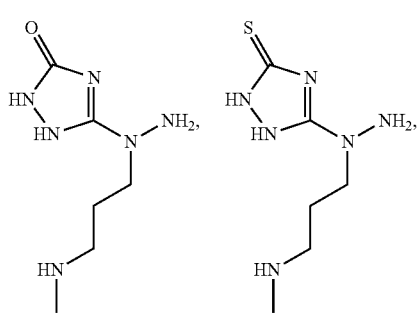
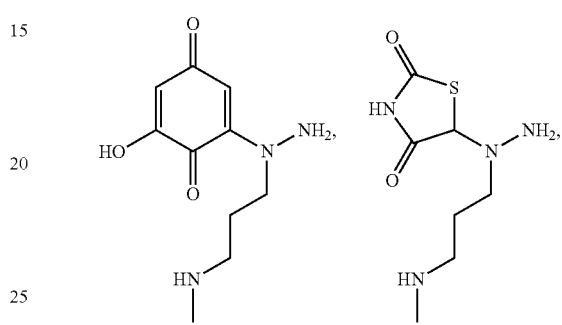
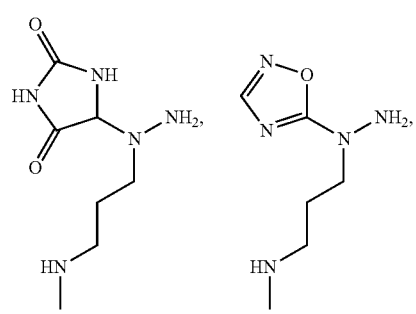
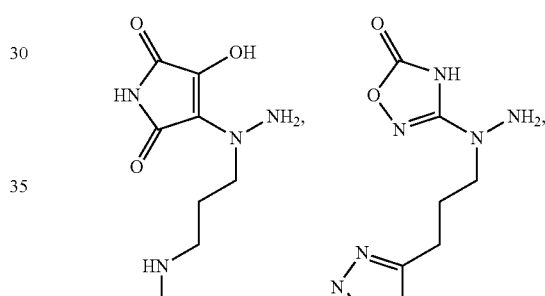
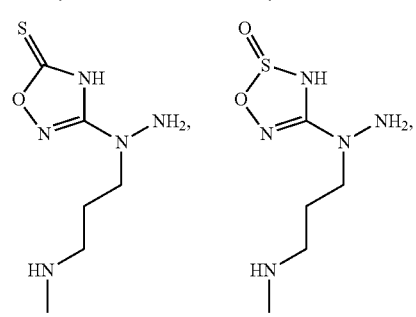
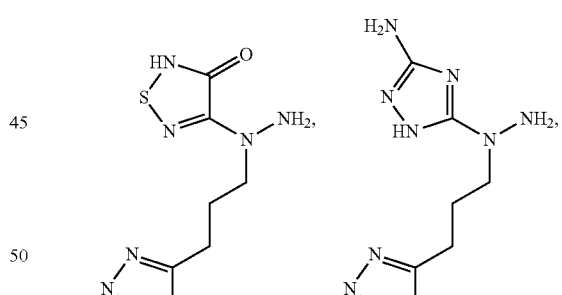
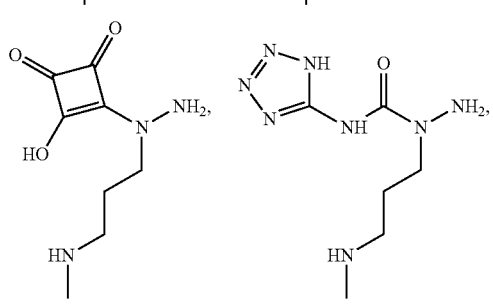
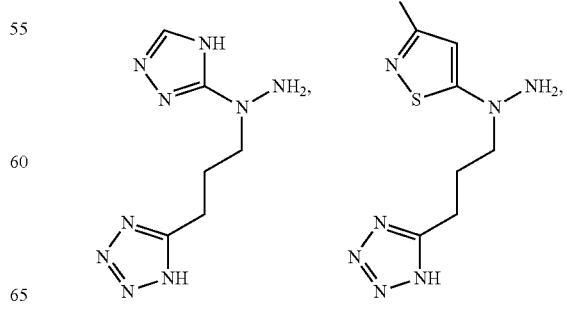

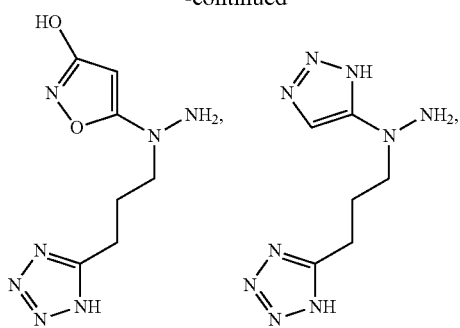
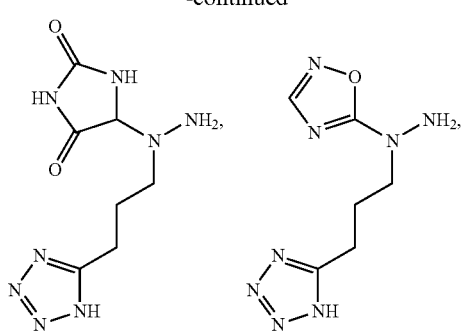

-continued

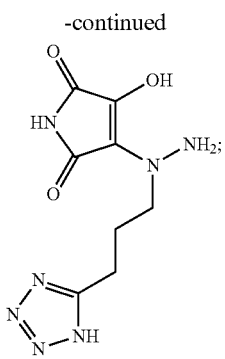

or a pharmaceutically acceptable salt, solvate, or prodrug thereof.

In some embodiments is a compound selected from:

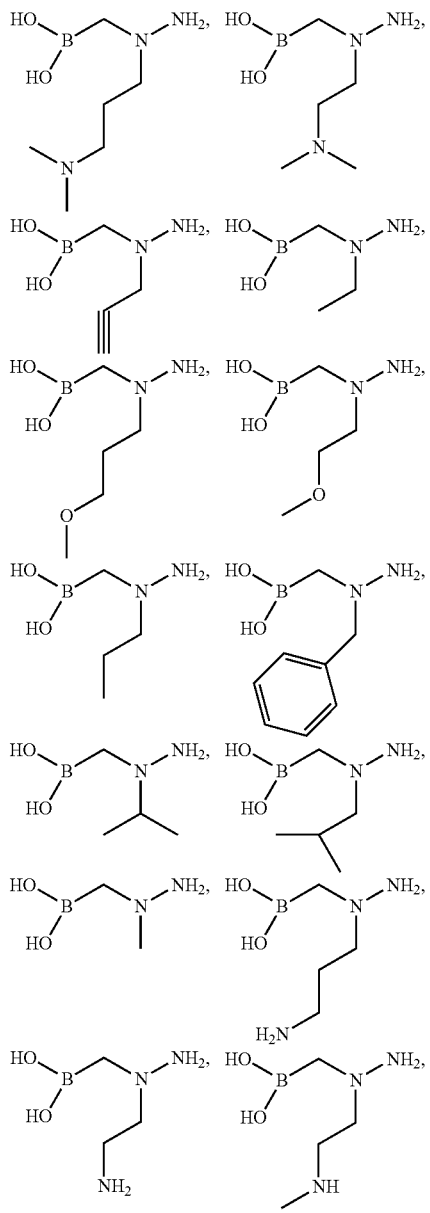

-continued

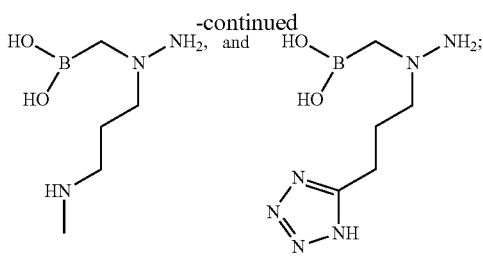

or a pharmaceutically acceptable salt, solvate, or prodrug thereof.

Provided herein are pharmaceutical compositions comprising a therapeutically effective amount of a compound of Formula (I), (II), (III), (IV), (V), or (VI), or a pharmaceutically acceptable salt, solvate, or prodrug thereof, and a pharmaceutically acceptable carrier, wherein the compound of Formula (I), (II), (III), (IV), (V), or (VI) is as described herein.

Routes of Administration

Suitable routes of administration include, but are not limited to, oral, intravenous, aerosol, parenteral, ophthalmic, pulmonary, transmucosal, transdermal, nasal, and topical administration. In addition, by way of example only, parenteral delivery includes intramuscular, subcutaneous, intravenous, intramedullary injections, as well as intrathecal, direct intraventricular, intraperitoneal, intralymphatic, and/or intranasal injections.

In certain embodiments, a compound of Formula (I), (II), (III), (IV), (V), or (VI) is administered in a local rather than systemic manner, for example, via topical application of the compound directly on to skin, or intravenously, or subcutaneously, often in a depot preparation or sustained release formulation. In specific embodiments, long acting formulations are administered by implantation (for example subcutaneously or intramuscularly) or by intramuscular injection. In yet other embodiments, the compound as described herein is provided in the form of a rapid release formulation, in the form of an extended release formulation, or in the form of an intermediate release formulation. In yet other embodiments, the compound described herein is administered topically (e.g., as a patch, an ointment, or in combination with a wound dressing, or as a wash or a spray). In alternative embodiments, a formulation is administered systemically (e.g., by injection, or as a pill).

Pharmaceutical Compositions/Formulations

In some embodiments, the compounds described herein are formulated into pharmaceutical compositions. Pharmaceutical compositions are formulated in a conventional manner using one or more pharmaceutically acceptable inactive ingredients that facilitate processing of the active compounds into preparations that can be used pharmaceutically. Proper formulation is dependent upon the route of administration chosen. A summary of pharmaceutical compositions described herein can be found, for example, in Remington: The Science and Practice of Pharmacy, Nineteenth Ed (Easton, Pa.: Mack Publishing Company, 1995); Hoover, John E., Remington's Pharmaceutical Sciences, Mack Publishing Co., Easton, Pa. 1975; Liberman, H. A. and Lachman, L., Eds., Pharmaceutical Dosage Forms, Marcel Decker, New York, N.Y., 1980; and Pharmaceutical Dosage Forms and Drug Delivery Systems, Seventh Ed. (Lippincott Williams & Wilkins 1999), herein incorporated by reference for such disclosure.

Provided herein are pharmaceutical compositions that include a compound of Formula (I), (II), (III), (IV), (V), or (VI) and at least one pharmaceutically acceptable inactive ingredient. In some embodiments, the compounds described herein are administered as pharmaceutical compositions in which compounds of Formula (I), (II), (III), (IV), (V), or (VI) are mixed with other active ingredients, as in combination therapy. In other embodiments, the pharmaceutical compositions include other medicinal or pharmaceutical agents, carriers, adjuvants, preserving, stabilizing, wetting or emulsifying agents, solution promoters, salts for regulating the osmotic pressure, and/or buffers. In yet other embodiments, the pharmaceutical compositions include other therapeutically valuable substances.

A pharmaceutical composition, as used herein, refers to a mixture of a compound of Formula (I), (II), (III), (IV), (V), or (VI) with other chemical components (i.e. pharmaceutically acceptable inactive ingredients), such as carriers, excipients, binders, filling agents, suspending agents, flavoring agents, sweetening agents, disintegrating agents, dispersing agents, surfactants, lubricants, colorants, diluents, solubilizers, moistening agents, plasticizers, stabilizers, penetration enhancers, wetting agents, anti-foaming agents, antioxidants, preservatives, or one or more combination thereof. The pharmaceutical composition facilitates administration of the compound to an organism. In practicing the methods of treatment or use provided herein, therapeutically effective amounts of compounds described herein are administered in a pharmaceutical composition to a mammal having a disease, disorder, or condition to be treated. In some embodiments, the mammal is a human. A therapeutically effective amount can vary widely depending on the severity of the disease, the age and relative health of the subject, the potency of the compound used and other factors. The compounds can be used singly or in combination with one or more therapeutic agents as components of mixtures.

The pharmaceutical formulations described herein are administered to a subject by appropriate administration routes, including but not limited to, oral, parenteral (e.g., intravenous, subcutaneous, intramuscular), intranasal, buccal, topical, or transdermal administration routes. The pharmaceutical formulations described herein include, but are not limited to, aqueous liquid dispersions, self-emulsifying dispersions, solid solutions, liposomal dispersions, aerosols, solid dosage forms, powders, immediate release formulations, controlled release formulations, fast melt formulations, tablets, capsules, pills, delayed release formulations, extended release formulations, pulsatile release formulations, multiparticulate formulations, and mixed immediate and controlled release formulations.

Pharmaceutical compositions including a compound of Formula (I), (II), (III), (IV), (V), or (VI) are manufactured in a conventional manner, such as, by way of example only, by means of conventional mixing, dissolving, granulating, dragee-making, levigating, emulsifying, encapsulating, entrapping or compression processes.

The pharmaceutical compositions will include at least one compound of Formula (I), (II), (III), (IV), (V), or (VI) as an active ingredient in free-acid or free-base form, or in a pharmaceutically acceptable salt form. In addition, the methods and pharmaceutical compositions described herein include the use of N-oxides (if appropriate), crystalline forms, amorphous phases, as well as active metabolites of these compounds having the same type of activity.

In some embodiments, compounds of Formula (I), (II), (III), (IV), (V), or (VI) exist in unsolvated form or in solvated forms with pharmaceutically acceptable solvents such as water, ethanol, and the like. The solvated forms of the compounds of Formula (I), (II), (III), (IV), (V), or (VI) are also considered to be disclosed herein.

In some embodiments, the compounds of Formula (I), (II), (III), (IV), (V), or (VI) exist as tautomers. All tautomers are included within the scope of the compounds presented herein. As such, it is to be understood that a compound of the Formula (I), (II), (III), (IV), (V), or (VI) or a salt thereof may exhibit the phenomenon of tautomerism whereby two chemical compounds that are capable of facile interconversion by exchanging a hydrogen atom between two atoms, to either of which it forms a covalent bond. Since the tautomeric compounds exist in mobile equilibrium with each other they may be regarded as different isomeric forms of the same compound. It is to be understood that the formulae drawings within this specification can represent only one of the possible tautomeric forms. However, it is also to be understood that the present disclosure encompasses any tautomeric form, and is not to be limited merely to any one tautomeric form utilized within the formulae drawings. The formulae drawings within this specification can represent only one of the possible tautomeric forms and it is to be understood that the specification encompasses all possible tautomeric forms of the compounds drawn not just those forms which it has been convenient to show graphically herein. For example, tautomerism may be exhibited by a tetrazole group or a triazole group bonded as indicated by the wavy line:

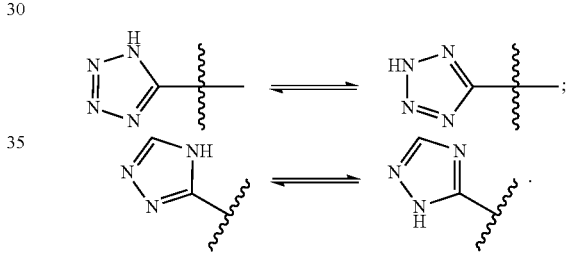

In some embodiments, compounds of Formula (I), (II), (III), (IV), (V), or (VI) exist as enantiomers, diastereomers, or other steroisomeric forms. The compounds disclosed herein include all enantiomeric, diastereomeric, and epimeric forms as well as mixtures thereof.

In some embodiments, compounds described herein may be prepared as prodrugs. A "prodrug" refers to an agent that is converted into the parent drug in vivo. Prodrugs are often useful because, in some situations, they may be easier to administer than the parent drug. They may, for instance, be bioavailable by oral administration whereas the parent is not. The prodrug may also have improved solubility in pharmaceutical compositions over the parent drug. An example, without limitation, of a prodrug would be a compound described herein, which is administered as an ester (the "prodrug") to facilitate transmittal across a cell membrane where water solubility is detrimental to mobility but which then is metabolically hydrolyzed to the carboxylic acid, the active entity, once inside the cell where water-solubility is beneficial. A further example of a prodrug might be a short peptide (polyaminoacid) bonded to an acid group where the peptide is metabolized to reveal the active moiety. In certain embodiments, upon in vivo administration, a prodrug is chemically converted to the biologically, pharmaceutically or therapeutically active form of the compound. In certain embodiments, a prodrug is enzymatically metabolized by one or more steps or processes to the biologically, pharmaceutically or therapeutically active form of the compound.

Prodrug forms of the herein described compounds, wherein the prodrug is metabolized in vivo to produce a compound of Formula (I), (II), (III), (IV), (V), or (VI) as set forth herein are included within the scope of the claims. Prodrug forms of the herein described compounds, wherein the prodrug is metabolized in vivo to produce a compound of Formula (I), (II), (III), (IV), or (V) as set forth herein are included within the scope of the claims. In some cases, some of the compounds described herein may be a prodrug for another derivative or active compound. In some embodiments described herein, hydrazones are metabolized in vivo to produce a compound of Formula (I), (II), (III), (IV), or (V). In some embodiments, compounds of Formula (VI) are metabolized in vivo to produce a compound of Formula (I), (II), (III), (IV), or (V).

In certain embodiments, compositions provided herein include one or more preservatives to inhibit microbial activity. Suitable preservatives include mercury-containing substances such as merfen and thiomersal; stabilized chlorine dioxide; and quaternary ammonium compounds such as benzalkonium chloride, cetyltrimethylammonium bromide and cetylpyridinium chloride.

In some embodiments, formulations described herein benefit from antioxidants, metal chelating agents, thiol containing compounds and other general stabilizing agents. Examples of such stabilizing agents, include, but are not limited to: (a) about 0.5% to about 2% w/v glycerol, (b) about 0.1% to about 1% w/v methionine, (c) about 0.1% to about 2% w/v monothioglycerol, (d) about 1 mM to about 10 mM EDTA, (e) about 0.01% to about 2% w/v ascorbic acid, (f) 0.003% to about 0.02% w/v polysorbate 80, (g) 0.001% to about 0.05% w/v. polysorbate 20, (h) arginine, (i) heparin, (j) dextran sulfate, (k) cyclodextrins, (l) pentosan polysulfate and other heparinoids, (m) divalent cations such as magnesium and zinc; or (n) combinations thereof.

The pharmaceutical compositions described herein, which include a compound of Formula (I), (II), (III), (IV), (V), or (VI) are formulated into any suitable dosage form, including but not limited to, aqueous oral dispersions, liquids, gels, syrups, elixirs, slurries, suspensions, solid oral dosage forms, aerosols, controlled release formulations, fast melt formulations, effervescent formulations, lyophilized formulations, tablets, powders, pills, dragees, capsules, delayed release formulations, extended release formulations, pulsatile release formulations, multiparticulate formulations, and mixed immediate release and controlled release formulations.

Certain Topical Compositions

In some embodiments, compounds of Formula (I), (II), (III), (IV), (V), or (VI) are prepared as transdermal dosage forms. In one embodiment, the transdermal formulations described herein include at least three components: (1) a formulation of a compound of Formula (I), (II), (III), (IV), (V), or (VI); (2) a penetration enhancer; and (3) an optional aqueous adjuvant. In some embodiments the transdermal formulations include additional components such as, but not limited to, gelling agents, creams and ointment bases, and the like. In some embodiments, the transdermal formulation is presented as a patch or a wound dressing. In some embodiments, the transdermal formulation further include a woven or non-woven backing material to enhance absorption and prevent the removal of the transdermal formulation from the skin. In other embodiments, the transdermal formulations described herein can maintain a saturated or supersaturated state to promote diffusion into the skin.

In one aspect, formulations suitable for transdermal administration of compounds described herein employ transdermal delivery devices and transdermal delivery patches and can be lipophilic emulsions or buffered, aqueous solutions, dissolved and/or dispersed in a polymer or an adhesive. In one aspect, such patches are constructed for continuous, pulsatile, or on demand delivery of pharmaceutical agents. Still further, transdermal delivery of the compounds described herein can be accomplished by means of iontophoretic patches and the like. In one aspect, transdermal patches provide controlled delivery of a compound of Formula (I), (II), (III), (IV), (V), or (VI). In one aspect, transdermal devices are in the form of a bandage comprising a backing member, a reservoir containing the compound optionally with carriers, optionally a rate controlling barrier to deliver the compound to the skin of the host at a controlled and predetermined rate over a prolonged period of time, and means to secure the device to the skin.

In further embodiments, topical formulations include gel formulations (e.g., gel patches which adhere to the skin). In some of such embodiments, a gel composition includes any polymer that forms a gel upon contact with the body (e.g., gel formulations comprising hyaluronic acid, pluronic polymers, poly(lactic-co-glycolic acid (PLGA)-based polymers or the like). In some forms of the compositions, the formulation comprises a low-melting wax such as, but not limited to, a mixture of fatty acid glycerides, optionally in combination with cocoa butter which is first melted. Optionally, the formulations further comprise a moisturizing agent.

In certain embodiments, delivery systems for pharmaceutical compounds may be employed, such as, for example, liposomes and emulsions. In certain embodiments, compositions provided herein can also include an mucoadhesive polymer, selected from among, for example, carboxymethylcellulose, carbomer (acrylic acid polymer), poly(methylmethacrylate), polyacrylamide, polycarbophil, acrylic acid/butyl acrylate copolymer, sodium alginate and dextran.

In some embodiments, the compounds described herein may be administered topically and can be formulated into a variety of topically administrable compositions, such as solutions, suspensions, lotions, gels, pastes, medicated sticks, balms, creams or ointments. Such pharmaceutical compounds can contain solubilizers, stabilizers, tonicity enhancing agents, buffers and preservatives.

In alternative embodiments, a compound of Formula (I), (II), (III), (IV), (V), or (VI) is formulated and presented as a wash or rinse liquid which is used to irrigate the affected area. In further embodiments, a compound of Formula (I), (II), (III), (IV), (V), or (VI) is formulated and presented as a spray which is applied to the affected area.

Wound Dressings

In one aspect, a compound of Formula (I), (II), (III), (IV), (V), or (VI) is presented as part of a wound dressing. A dressing is an adjunct used for application to a wound to promote healing and/or prevent further harm. A dressing is designed to be in direct contact with a wound. In some embodiments, a wound dressing comprising a CSE inhibitor described herein provides a controlled release of the CSE inhibitor. In other embodiments, a wound dressing comprising a CSE inhibitor described herein provides sustained release of the CSE inhibitor. In other embodiments, a wound dressing comprising a CSE inhibitor described herein provides intermediate release of the CSE inhibitor. In further embodiments, a wound dressing comprising a CSE inhibitor described herein provides intermediate release of the CSE inhibitor. In other embodiments, a wound dressing comprising a CSE inhibitor described herein provides a combination of sustained, intermediate or immediate release of the CSE inhibitor.

Optionally a wound dressing comprising a CSE inhibitor comprises particles of the CSE inhibitor designed for controlled release (e.g., micronized particles, nanosized particles or a mixture thereof, non-sized particles, coated particles for controlled and/or sustained release). In some embodiments, a wound dressing is a gel patch that adheres to the skin at the site of the wound or cutaneous injury or condition. In some embodiments, a gel patch comprises any suitable gelling polymer (e.g., hyaluronan, carbomer polymers, pluronic polymers, PLGA polymers or the like). In some embodiments, a wound dressing comprises a coating on a sticky tape (e.g., medicated bandage or tape). In some embodiments, a wound dressing is a liquid which gels upon contacting the skin and is administered as a spray-on or paint.

In some additional embodiments, a CSE inhibitor is administered topically or systemically in combination with a wound dressing. In some of such embodiments, the wound dressing is non-medicated (i.e., does not comprise the CSE inhibitor). In some other embodiments, the wound dressing comprises a CSE inhibitor as described above.

In further embodiments, a CSE inhibitor is administered topically or systemically in combination with a wound dressing and a bandage.

Certain Systemically Administered Compositions

In one aspect, a compound of Formula (I), (II), (III), (IV), (V), or (VI) is formulated into a pharmaceutical composition suitable for intramuscular, subcutaneous, or intravenous injection. In one aspect, formulations suitable for intramuscular, subcutaneous, or intravenous injection include physiologically acceptable sterile aqueous or non-aqueous solutions, dispersions, suspensions or emulsions, and sterile powders for reconstitution into sterile injectable solutions or dispersions. Examples of suitable aqueous and non-aqueous carriers, diluents, solvents, or vehicles include water, ethanol, polyols (propyleneglycol, polyethylene-glycol, glycerol, cremophor and the like), suitable mixtures thereof, vegetable oils (such as olive oil) and injectable organic esters such as ethyl oleate. Proper fluidity can be maintained, for example, by the use of a coating such as lecithin, by the maintenance of the required particle size in the case of dispersions, and by the use of surfactants. In some embodiments, formulations suitable for subcutaneous injection also contain additives such as preserving, wetting, emulsifying, and dispensing agents. Prevention of the growth of microorganisms can be ensured by various antibacterial and antifungal agents, such as parabens, chlorobutanol, phenol, sorbic acid, and the like. In some cases it is desirable to include isotonic agents, such as sugars, sodium chloride, and the like. Prolonged absorption of the injectable pharmaceutical form can be brought about by the use of agents delaying absorption, such as aluminum monostearate and gelatin.

For intravenous injections or drips or infusions, compounds described herein are formulated in aqueous solutions, preferably in physiologically compatible buffers such as Hank's solution, Ringer's solution, or physiological saline buffer. For transmucosal administration, penetrants appropriate to the barrier to be permeated are used in the formulation. Such penetrants are generally known in the art. For other parenteral injections, appropriate formulations include aqueous or nonaqueous solutions, preferably with physiologically compatible buffers or excipients. Such excipients are known.

Parenteral injections may involve bolus injection or continuous infusion. Formulations for injection may be presented in unit dosage form, e.g., in ampoules or in multi-dose containers, with an added preservative. The pharmaceutical composition described herein may be in a form suitable for parenteral injection as a sterile suspensions, solutions or emulsions in oily or aqueous vehicles, and may contain formulatory agents such as suspending, stabilizing and/or dispersing agents. In one aspect, the active ingredient is in powder form for constitution with a suitable vehicle, e.g., sterile pyrogen-free water, before use.

For administration by inhalation, a compound of Formula (I), (II), (III), (IV), (V), or (VI) is formulated for use as an aerosol, a mist or a powder. Pharmaceutical compositions described herein are conveniently delivered in the form of an aerosol spray presentation from pressurized packs or a nebuliser, with the use of a suitable propellant, e.g., dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. Capsules and cartridges of, such as, by way of example only, gelatin for use in an inhaler or insufflator may be formulated containing a powder mix of the compound described herein and a suitable powder base such as lactose or starch.

Representative intranasal formulations are described in, for example, U.S. Pat. Nos. 4,476,116, 5,116,817 and 6,391,452. Formulations that include a compound of Formula (I) are prepared as solutions in saline, employing benzyl alcohol or other suitable preservatives, fluorocarbons, and/or other solubilizing or dispersing agents known in the art. See, for example, Ansel, H. C. et al., Pharmaceutical Dosage Forms and Drug Delivery Systems, Sixth Ed. (1995). Preferably these compositions and formulations are prepared with suitable nontoxic pharmaceutically acceptable ingredients. These ingredients are known to those skilled in the preparation of nasal dosage forms and some of these can be found in REMINGTON: THE SCIENCE AND PRACTICE OF PHARMACY, 21st edition, 2005. The choice of suitable carriers is dependent upon the exact nature of the nasal dosage form desired, e.g., solutions, suspensions, ointments, or gels. Nasal dosage forms generally contain large amounts of water in addition to the active ingredient. Minor amounts of other ingredients such as pH adjusters, emulsifiers or dispersing agents, preservatives, surfactants, gelling agents, or buffering and other stabilizing and solubilizing agents are optionally present. Preferably, the nasal dosage form should be isotonic with nasal secretions.

Pharmaceutical preparations for oral use are obtained by mixing one or more solid excipient with one or more of the compounds described herein, optionally grinding the resulting mixture, and processing the mixture of granules, after adding suitable auxiliaries, if desired, to obtain tablets or dragee cores. Suitable excipients include, for example, fillers such as sugars, including lactose, sucrose, mannitol, or sorbitol; cellulose preparations such as, for example, maize starch, wheat starch, rice starch, potato starch, gelatin, gum tragacanth, methylcellulose, microcrystalline cellulose, hydroxypropylmethylcellulose, sodium carboxymethylcellulose; or others such as: polyvinylpyrrolidone (PVP or povidone) or calcium phosphate. If desired, disintegrating agents are added, such as the cross-linked croscarmellose sodium, polyvinylpyrrolidone, agar, or alginic acid or a salt thereof such as sodium alginate. In some embodiments, dyestuffs or pigments are added to the tablets or dragee coatings for identification or to characterize different combinations of active compound doses.

In some embodiments, pharmaceutical formulations of a compound of Formula (I), (II), (III), (IV), (V), or (VI) are in the form of a capsules, including push-fit capsules made of gelatin, as well as soft, sealed capsules made of gelatin and a plasticizer, such as glycerol or sorbitol. The push-fit capsules contain the active ingredients in admixture with filler such as lactose, binders such as starches, and/or lubricants such as talc or magnesium stearate and, optionally, stabilizers. In soft capsules, the active compounds are dissolved or suspended in suitable liquids, such as fatty oils, liquid paraffin, or liquid polyethylene glycols. In some embodiments, stabilizers are added. A capsule may be prepared, for example, by placing the bulk blend of the formulation of the compound described above, inside of a capsule. In some embodiments, the formulations (non-aqueous suspensions and solutions) are placed in a soft gelatin capsule. In other embodiments, the formulations are placed in standard gelatin capsules or non-gelatin capsules such as capsules comprising HPMC. In other embodiments, the formulation is placed in a sprinkle capsule, wherein the capsule is swallowed whole or the capsule is opened and the contents sprinkled on food prior to eating.

All formulations for oral administration are in dosages suitable for such administration.

In one aspect, solid oral dosage forms are prepared by mixing a compound of Formula (I), (II), (III), (IV), (V), or (VI) with one or more of the following: antioxidants, flavoring agents, and carrier materials such as binders, suspending agents, disintegration agents, filling agents, surfactants, solubilizers, stabilizers, lubricants, wetting agents, and diluents.

In some embodiments, the solid dosage forms disclosed herein are in the form of a tablet, (including a suspension tablet, a fast-melt tablet, a bite-disintegration tablet, a rapid-disintegration tablet, an effervescent tablet, or a caplet), a pill, a powder, a capsule, solid dispersion, solid solution, bioerodible dosage form, controlled release formulations, pulsatile release dosage forms, multiparticulate dosage forms, beads, pellets, granules. In other embodiments, the pharmaceutical formulation is in the form of a powder.

Compressed tablets are solid dosage forms prepared by compacting the bulk blend of the formulations described above. In various embodiments, tablets will include one or more flavoring agents.

In other embodiments, the tablets will include a film surrounding the final compressed tablet. In some embodiments, the film coating can provide a delayed release of the compound of Formula (I), (II), (III), (IV), (V), or (VI) from the formulation. In other embodiments, the film coating aids in patient compliance (e.g., Opadry® coatings or sugar coating). Film coatings including Opadry® typically range from about 1% to about 3% of the tablet weight.

In some embodiments, solid dosage forms, e.g., tablets, effervescent tablets, and capsules, are prepared by mixing particles of a compound with one or more pharmaceutical excipients to form a bulk blend composition. The bulk blend is readily subdivided into equally effective unit dosage forms, such as tablets, pills, and capsules. In some embodiments, the individual unit dosages include film coatings. These formulations are manufactured by conventional formulation techniques.

In another aspect, dosage forms include microencapsulated formulations. In some embodiments, one or more other compatible materials are present in the microencapsulation material. Exemplary materials include, but are not limited to, pH modifiers, erosion facilitators, anti-foaming agents, antioxidants, flavoring agents, and carrier materials such as binders, suspending agents, disintegration agents, filling agents, surfactants, solubilizers, stabilizers, lubricants, wetting agents, and diluents.

Exemplary useful microencapsulation materials include, but are not limited to, hydroxypropyl cellulose ethers (HPC) such as Klucel® or Nisso HPC, low-substituted hydroxypropyl cellulose ethers (L-HPC), hydroxypropyl methyl cellulose ethers (HPMC) such as Seppifilm-LC, Pharmacoat®, Metolose SR, Methocel®-E, Opadry YS, PrimaFlo, Benecel MP824, and Benecel MP843, methylcellulose polymers such as Methocel®-A, hydroxypropylmethylcellulose acetate stearate Aqoat (HF-LS, HF-LG,HF-MS) and Metolose®, Ethylcelluloses (EC) and mixtures thereof such as E461, Ethocel®, Aqualon®-EC, Surelease®, Polyvinyl alcohol (PVA) such as Opadry AMB, hydroxyethylcelluloses such as Natrosol®, carboxymethylcelluloses and salts of carboxymethylcelluloses (CMC) such as Aqualon®-CMC, polyvinyl alcohol and polyethylene glycol co-polymers such as Kollicoat IR®, monoglycerides (Myverol), triglycerides (KLX), polyethylene glycols, modified food starch, acrylic polymers and mixtures of acrylic polymers with cellulose ethers such as Eudragit® EPO, Eudragit® L30D-55, Eudragit® FS 30D Eudragit® L100-55, Eudragit® L100, Eudragit® S100, Eudragit® RD100, Eudragit® E100, Eudragit® L12.5, Eudragit® S12.5, Eudragit® NE30D, and Eudragit® NE 40D, cellulose acetate phthalate, sepifilms such as mixtures of HPMC and stearic acid, cyclodextrins, and mixtures of these materials.

Liquid formulation dosage forms for oral administration are optionally aqueous suspensions selected from the group including, but not limited to, pharmaceutically acceptable aqueous oral dispersions, emulsions, solutions, elixirs, gels, and syrups. See, e.g., Singh et al., Encyclopedia of Pharmaceutical Technology, 2nd Ed., pp. 754-757 (2002). In addition to a CSE inhibitor, the liquid dosage forms optionally include additives, such as: (a) disintegrating agents; (b) dispersing agents; (c) wetting agents; (d) at least one preservative, (e) viscosity enhancing agents, (f) at least one sweetening agent, and (g) at least one flavoring agent. In some embodiments, the aqueous dispersions further includes a crystal-forming inhibitor.

In some embodiments, the pharmaceutical formulations described herein are self-emulsifying drug delivery systems (SEDDS). Emulsions are dispersions of one immiscible phase in another, usually in the form of droplets. Generally, emulsions are created by vigorous mechanical dispersion. SEDDS, as opposed to emulsions or microemulsions, spontaneously form emulsions when added to an excess of water without any external mechanical dispersion or agitation. An advantage of SEDDS is that only gentle mixing is required to distribute the droplets throughout the solution. Additionally, water or the aqueous phase is optionally added just prior to administration, which ensures stability of an unstable or hydrophobic active ingredient. Thus, the SEDDS provides an effective delivery system for oral and parenteral delivery of hydrophobic active ingredients. In some embodiments, SEDDS provides improvements in the bioavailability of hydrophobic active ingredients. Methods of producing self-emulsifying dosage forms include, but are not limited to, for example, U.S. Pat. Nos. 5,858,401, 6,667,048, and 6,960,563.

Buccal formulations that include a compound of Formula (I), (II), (III), (IV), (V), or (VI) are administered using a variety of formulations known in the art. For example, such formulations include, but are not limited to, U.S. Pat. Nos.

4,229,447, 4,596,795, 4,755,386, and 5,739,136. In addition, the buccal dosage forms described herein can further include a bioerodible (hydrolysable) polymeric carrier that also serves to adhere the dosage form to the buccal mucosa. For buccal or sublingual administration, the compositions may take the form of tablets, lozenges, or gels formulated in a conventional manner.

For intravenous injections, a CSE inhibitor is optionally formulated in aqueous solutions, preferably in physiologically compatible buffers such as Hank's solution, Ringer's solution, or physiological saline buffer. For transmucosal administration, penetrants appropriate to the barrier to be permeated are used in the formulation. For other parenteral injections, appropriate formulations include aqueous or non-aqueous solutions, preferably with physiologically compatible buffers or excipients.

Parenteral injections optionally involve bolus injection or continuous infusion. Formulations for injection are optionally presented in unit dosage form, e.g., in ampoules or in multi dose containers, with an added preservative. In some embodiments, a pharmaceutical composition described herein is in a form suitable for parenteral injection as a sterile suspensions, solutions or emulsions in oily or aqueous vehicles, and contain formulatory agents such as suspending, stabilizing and/or dispersing agents. Pharmaceutical formulations for parenteral administration include aqueous solutions of an agent that modulates the activity of a carotid body in water soluble form. Additionally, suspensions of an agent that modulates the activity of a carotid body are optionally prepared as appropriate, e.g., oily injection suspensions.

Conventional formulation techniques include, e.g., one or a combination of methods: (1) dry mixing, (2) direct compression, (3) milling, (4) dry or non-aqueous granulation, (5) wet granulation, or (6) fusion. Other methods include, e.g., spray drying, pan coating, melt granulation, granulation, fluidized bed spray drying or coating (e.g., wurster coating), tangential coating, top spraying, tableting, extruding and the like.

Suitable carriers for use in the solid dosage forms described herein include, but are not limited to, acacia, gelatin, colloidal silicon dioxide, calcium glycerophosphate, calcium lactate, maltodextrin, glycerine, magnesium silicate, sodium caseinate, soy lecithin, sodium chloride, tricalcium phosphate, dipotassium phosphate, sodium stearoyl lactylate, carrageenan, monoglyceride, diglyceride, pregelatinized starch, hydroxypropylmethylcellulose, hydroxypropylmethylcellulose acetate stearate, sucrose, microcrystalline cellulose, lactose, mannitol and the like.

Suitable filling agents for use in the solid dosage forms described herein include, but are not limited to, lactose, calcium carbonate, calcium phosphate, dibasic calcium phosphate, calcium sulfate, microcrystalline cellulose, cellulose powder, dextrose, dextrates, dextran, starches, pregelatinized starch, hydroxypropylmethylcellulose (HPMC), hydroxypropylmethycellulose phthalate, hydroxypropylmethylcellulose acetate stearate (HPMCAS), sucrose, xylitol, lactitol, mannitol, sorbitol, sodium chloride, polyethylene glycol, and the like.

Suitable disintegrants for use in the solid dosage forms described herein include, but are not limited to, natural starch such as corn starch or potato starch, a pregelatinized starch, or sodium starch glycolate, a cellulose such as methylcrystalline cellulose, methylcellulose, microcrystalline cellulose, croscarmellose, or a cross-linked cellulose, such as cross-linked sodium carboxymethylcellulose, cross-linked carboxymethylcellulose, or cross-linked croscarmellose, a cross-linked starch such as sodium starch glycolate, a cross-linked polymer such as crospovidone, a cross-linked polyvinylpyrrolidone, alginate such as alginic acid or a salt of alginic acid such as sodium alginate, a gum such as agar, guar, locust bean, Karaya, pectin, or tragacanth, sodium starch glycolate, bentonite, sodium lauryl sulfate, sodium lauryl sulfate in combination starch, and the like.

Binders impart cohesiveness to solid oral dosage form formulations: for powder filled capsule formulation, they aid in plug formation that can be filled into soft or hard shell capsules and for tablet formulation, they ensure the tablet remaining intact after compression and help assure blend uniformity prior to a compression or fill step. Materials suitable for use as binders in the solid dosage forms described herein include, but are not limited to, carboxymethylcellulose, methylcellulose, hydroxypropylmethylcellulose, hydroxypropylmethylcellulose acetate stearate, hydroxyethylcellulose, hydroxypropylcellulose, ethylcellulose, and microcrystalline cellulose, microcrystalline dextrose, amylose, magnesium aluminum silicate, polysaccharide acids, bentonites, gelatin, polyvinylpyrrolidone/vinyl acetate copolymer, crospovidone, povidone, starch, pregelatinized starch, tragacanth, dextrin, a sugar, such as sucrose, glucose, dextrose, molasses, mannitol, sorbitol, xylitol, lactose, a natural or synthetic gum such as acacia, tragacanth, ghatti gum, mucilage of isapol husks, starch, polyvinylpyrrolidone, larch arabogalactan, polyethylene glycol, waxes, sodium alginate, and the like.

In general, binder levels of 20-70% are used in powder-filled gelatin capsule formulations. Binder usage level in tablet formulations varies whether direct compression, wet granulation, roller compaction, or usage of other excipients such as fillers which itself can act as moderate binder. Binder levels of up to 70% in tablet formulations is common.

Suitable lubricants or glidants for use in the solid dosage forms described herein include, but are not limited to, stearic acid, calcium hydroxide, talc, corn starch, sodium stearyl fumerate, alkali-metal and alkaline earth metal salts, such as aluminum, calcium, magnesium, zinc, stearic acid, sodium stearates, magnesium stearate, zinc stearate, waxes, Stearowet®, boric acid, sodium benzoate, sodium acetate, sodium chloride, leucine, a polyethylene glycol or a methoxypolyethylene glycol such as Carbowax™, PEG 4000, PEG 5000, PEG 6000, propylene glycol, sodium oleate, glyceryl behenate, glyceryl palmitostearate, glyceryl benzoate, magnesium or sodium lauryl sulfate, and the like.

Suitable diluents for use in the solid dosage forms described herein include, but are not limited to, sugars (including lactose, sucrose, and dextrose), polysaccharides (including dextrates and maltodextrin), polyols (including mannitol, xylitol, and sorbitol), cyclodextrins and the like.

Suitable wetting agents for use in the solid dosage forms described herein include, for example, oleic acid, glyceryl monostearate, sorbitan monooleate, sorbitan monolaurate, triethanolamine oleate, polyoxyethylene sorbitan monooleate, polyoxyethylene sorbitan monolaurate, quaternary ammonium compounds (e.g., Polyquat 10®), sodium oleate, sodium lauryl sulfate, magnesium stearate, sodium docusate, triacetin, vitamin E TPGS and the like.

Suitable surfactants for use in the solid dosage forms described herein include, for example, sodium lauryl sulfate, sorbitan monooleate, polyoxyethylene sorbitan monooleate, polysorbates, polaxomers, bile salts, glyceryl monostearate, copolymers of ethylene oxide and propylene oxide, e.g., Pluronic® (BASF), and the like.

Suitable suspending agents for use in the solid dosage forms described here include, but are not limited to, polyvinylpyrrolidone, e.g., polyvinylpyrrolidone K12, polyvinylpyrrolidone K17, polyvinylpyrrolidone K25, or polyvinylpyrrolidone K30, polyethylene glycol, e.g., the polyethylene glycol can have a molecular weight of about 300 to about 6000, or about 3350 to about 4000, or about 7000 to about 5400, vinyl pyrrolidone/vinyl acetate copolymer (S630), sodium carboxymethylcellulose, methylcellulose, hydroxy-propylmethylcellulose, polysorbate-80, hydroxyethylcellulose, sodium alginate, gums, such as, e.g., gum tragacanth and gum acacia, guar gum, xanthans, including xanthan gum, sugars, cellulosics, such as, e.g., sodium carboxymethylcellulose, methylcellulose, sodium carboxymethylcellulose, hydroxypropylmethylcellulose, hydroxyethylcellulose, polysorbate-80, sodium alginate, polyethoxylated sorbitan monolaurate, polyethoxylated sorbitan monolaurate, povidone and the like.

Suitable antioxidants for use in the solid dosage forms described herein include, for example, e.g., butylated hydroxytoluene (BHT), sodium ascorbate, and tocopherol.

It should be appreciated that there is considerable overlap between additives used in the solid dosage forms described herein. Thus, the above-listed additives should be taken as merely exemplary, and not limiting, of the types of additives that can be included in solid dosage forms of the pharmaceutical compositions described herein. The amounts of such additives can be readily determined by one skilled in the art, according to the particular properties desired.

In various embodiments, the particles of a compound of Formula (I), (II), (III), (IV), (V), or (VI) and one or more excipients are dry blended and compressed into a mass, such as a tablet, having a hardness sufficient to provide a pharmaceutical composition that substantially disintegrates within less than about 30 minutes, less than about 35 minutes, less than about 40 minutes, less than about 45 minutes, less than about 50 minutes, less than about 55 minutes, or less than about 60 minutes, after oral administration, thereby releasing the formulation into the gastrointestinal fluid.

In other embodiments, a powder including a compound of Formula (I), (II), (III), (IV), (V), or (VI) is formulated to include one or more pharmaceutical excipients and flavors. Such a powder is prepared, for example, by mixing the compound and optional pharmaceutical excipients to form a bulk blend composition. Additional embodiments also include a suspending agent and/or a wetting agent. This bulk blend is uniformly subdivided into unit dosage packaging or multi-dosage packaging units.

In still other embodiments, effervescent powders are also prepared. Effervescent salts have been used to disperse medicines in water for oral administration.

Controlled Release Formulations

In some embodiments, the pharmaceutical dosage forms are formulated to provide a controlled release of a compound of Formula (I), (II), (III), (IV), (V), or (VI). Controlled release refers to the release of the compound from a dosage form in which it is incorporated according to a desired profile over an extended period of time. Controlled release profiles include, for example, sustained release, prolonged release, pulsatile release, and delayed release profiles. In contrast to immediate release compositions, controlled release compositions allow delivery of an agent to a subject over an extended period of time according to a predetermined profile. Such release rates can provide therapeutically effective levels of agent for an extended period of time and thereby provide a longer period of pharmacologic response while minimizing side effects as compared to conventional rapid release dosage forms. Such longer periods of response provide for many inherent benefits that are not achieved with the corresponding short acting, immediate release preparations.

In some embodiments, the solid dosage forms described herein are formulated as enteric coated delayed release oral dosage forms, i.e., as an oral dosage form of a pharmaceutical composition as described herein which utilizes an enteric coating to affect release in the small intestine or large intestine. In one aspect, the enteric coated dosage form is a compressed or molded or extruded tablet/mold (coated or uncoated) containing granules, powder, pellets, beads or particles of the active ingredient and/or other composition components, which are themselves coated or uncoated. In one aspect, the enteric coated oral dosage form is in the form of a capsule containing pellets, beads or granules, which include a compound of Formula (I), (II), (III), (IV), (V), or (VI), that are coated or uncoated.

Any coatings should be applied to a sufficient thickness such that the entire coating does not dissolve in the gastrointestinal fluids at pH below about 5, but does dissolve at pH about 5 and above. Coatings are typically selected from any of the following:

Shellac—this coating dissolves in media of pH>7; Acrylic polymers—examples of suitable acrylic polymers include methacrylic acid copolymers and ammonium methacrylate copolymers. The Eudragit series E, L, S, RL, RS and NE (Rohm Pharma) are available as solubilized in organic solvent, aqueous dispersion, or dry powders. The Eudragit series RL, NE, and RS are insoluble in the gastrointestinal tract but are permeable and are used primarily for colonic targeting. The Eudragit series E dissolve in the stomach. The Eudragit series L, L-30D and S are insoluble in stomach and dissolve in the intestine; Poly Vinyl Acetate Phthalate (PVAP)—PVAP dissolves in pH>5, and it is much less permeable to water vapor and gastric fluids.

Conventional coating techniques such as spray or pan coating are employed to apply coatings. The coating thickness must be sufficient to ensure that the oral dosage form remains intact until the desired site of topical delivery in the intestinal tract is reached.

In other embodiments, the formulations described herein are delivered using a pulsatile dosage form. A pulsatile dosage form is capable of providing one or more immediate release pulses at predetermined time points after a controlled lag time or at specific sites. Exemplary pulsatile dosage forms and methods of their manufacture are disclosed in U.S. Pat. Nos. 5,011,692, 5,017,381, 5,229,135, 5,840,329 and 5,837,284. In one embodiment, the pulsatile dosage form includes at least two groups of particles, (i.e. multiparticulate) each containing the formulation described herein. The first group of particles provides a substantially immediate dose of the compound of Formula (I) upon ingestion by a mammal. The first group of particles can be either uncoated or include a coating and/or sealant. In one aspect, the second group of particles comprises coated particles. The coating on the second group of particles provides a delay of from about 2 hours to about 7 hours following ingestion before release of the second dose. Suitable coatings for pharmaceutical compositions are described herein or known in the art.

In some embodiments, pharmaceutical formulations are provided that include particles of a compound of Formula (I), (II), (III), (IV), (V), or (VI) and at least one dispersing agent or suspending agent for oral administration to a subject. The formulations may be a powder and/or granules for suspension, and upon admixture with water, a substantially uniform suspension is obtained.

In some embodiments, particles formulated for controlled release are incorporated in a gel or a patch or a wound dressing.

In one aspect, liquid formulation dosage forms for oral administration and/or for topical administration as a wash are in the form of aqueous suspensions selected from the group including, but not limited to, pharmaceutically acceptable aqueous oral dispersions, emulsions, solutions, elixirs, gels, and syrups. See, e.g., Singh et al., Encyclopedia of Pharmaceutical Technology, 2nd Ed., pp. 754-757 (2002). In addition to the particles of a compound of Formula (I), (II), (III), (IV), (V), or (VI), the liquid dosage forms include additives, such as: (a) disintegrating agents; (b) dispersing agents; (c) wetting agents; (d) at least one preservative, (e) viscosity enhancing agents, (f) at least one sweetening agent, and (g) at least one flavoring agent. In some embodiments, the aqueous dispersions can further include a crystalline inhibitor.

In some embodiments, the liquid formulations also include inert diluents commonly used in the art, such as water or other solvents, solubilizing agents, and emulsifiers. Exemplary emulsifiers are ethyl alcohol, isopropyl alcohol, ethyl carbonate, ethyl acetate, benzyl alcohol, benzyl benzoate, propyleneglycol, 1,3-butyleneglycol, dimethylformamide, sodium lauryl sulfate, sodium doccusate, cholesterol, cholesterol esters, taurocholic acid, phosphotidylcholine, oils, such as cottonseed oil, groundnut oil, corn germ oil, olive oil, castor oil, and sesame oil, glycerol, tetrahydrofurfuryl alcohol, polyethylene glycols, fatty acid esters of sorbitan, or mixtures of these substances, and the like.

Furthermore, pharmaceutical compositions optionally include one or more pH adjusting agents or buffering agents, including acids such as acetic, boric, citric, lactic, phosphoric and hydrochloric acids; bases such as sodium hydroxide, sodium phosphate, sodium borate, sodium citrate, sodium acetate, sodium lactate and tris-hydroxymethylaminomethane; and buffers such as citrate/dextrose, sodium bicarbonate and ammonium chloride. Such acids, bases and buffers are included in an amount required to maintain pH of the composition in an acceptable range.

Additionally, pharmaceutical compositions optionally include one or more salts in an amount required to bring osmolality of the composition into an acceptable range. Such salts include those having sodium, potassium or ammonium cations and chloride, citrate, ascorbate, borate, phosphate, bicarbonate, sulfate, thiosulfate or bisulfite anions; suitable salts include sodium chloride, potassium chloride, sodium thiosulfate, sodium bisulfite and ammonium sulfate.

Other pharmaceutical compositions optionally include one or more preservatives to inhibit microbial activity. Suitable preservatives include mercury-containing substances such as merfen and thiomersal; stabilized chlorine dioxide; and quaternary ammonium compounds such as benzalkonium chloride, cetyltrimethylammonium bromide and cetylpyridinium chloride.

In one embodiment, the aqueous suspensions and dispersions described herein remain in a homogenous state, as defined in The USP Pharmacists' Pharmacopeia (2005 edition, chapter 905), for at least 4 hours. In one embodiment, an aqueous suspension is re-suspended into a homogenous suspension by physical agitation lasting less than 1 minute. In still another embodiment, no agitation is necessary to maintain a homogeneous aqueous dispersion.

Examples of disintegrating agents for use in the aqueous suspensions and dispersions include, but are not limited to, a starch, e.g., a natural starch such as corn starch or potato starch, a pregelatinized starch, or sodium starch glycolate; a cellulose such as methylcrystalline cellulose, methylcellulose, croscarmellose, or a cross-linked cellulose, such as cross-linked sodium carboxymethylcellulose, cross-linked carboxymethylcellulose, or cross-linked croscarmellose; a cross-linked starch such as sodium starch glycolate; a cross-linked polymer such as crospovidone; a cross-linked polyvinylpyrrolidone; alginate such as alginic acid or a salt of alginic acid such as sodium alginate; a gum such as agar, guar, locust bean, Karaya, pectin, or tragacanth; sodium starch glycolate; bentonite; a natural sponge; a surfactant; a resin such as a cation-exchange resin; citrus pulp; sodium lauryl sulfate; sodium lauryl sulfate in combination starch; and the like.

In some embodiments, the dispersing agents suitable for the aqueous suspensions and dispersions described herein include, for example, hydrophilic polymers, electrolytes, Tween® 60 or 80, PEG, polyvinylpyrrolidone, and the carbohydrate-based dispersing agents such as, for example, hydroxypropylcellulose and hydroxypropyl cellulose ethers, hydroxypropyl methylcellulose and hydroxypropyl methylcellulose ethers, carboxymethylcellulose sodium, methylcellulose, hydroxyethylcellulose, hydroxypropylmethyl-cellulose phthalate, hydroxypropylmethyl-cellulose acetate stearate, noncrystalline cellulose, magnesium aluminum silicate, triethanolamine, polyvinyl alcohol (PVA), polyvinylpyrrolidone/vinyl acetate copolymer, 4-(1,1,3,3-tetramethylbutyl)-phenol polymer with ethylene oxide and formaldehyde (also known as tyloxapol), poloxamers; and poloxamines. In other embodiments, the dispersing agent is selected from a group not comprising one of the following agents: hydrophilic polymers; electrolytes; Tween® 60 or 80; PEG; polyvinylpyrrolidone (PVP); hydroxypropylcellulose and hydroxypropyl cellulose ethers; hydroxypropyl methylcellulose and hydroxypropyl methylcellulose ethers; carboxymethylcellulose sodium; methylcellulose; hydroxyethylcellulose; hydroxypropylmethyl-cellulose phthalate; hydroxypropylmethyl-cellulose acetate stearate; non-crystalline cellulose; magnesium aluminum silicate; triethanolamine; polyvinyl alcohol (PVA); 4-(1,1,3,3-tetramethylbutyl)-phenol polymer with ethylene oxide and formaldehyde; poloxamers; or poloxamines.

Wetting agents suitable for the aqueous suspensions and dispersions described herein include, but are not limited to, cetyl alcohol, glycerol monostearate, polyoxyethylene sorbitan fatty acid esters (e.g., the commercially available Tweens® such as e.g., Tween 20® and Tween 80®, and polyethylene glycols, oleic acid, glyceryl monostearate, sorbitan monooleate, sorbitan monolaurate, triethanolamine oleate, polyoxyethylene sorbitan monooleate, polyoxyethylene sorbitan monolaurate, sodium oleate, sodium lauryl sulfate, sodium docusate, triacetin, vitamin E TPGS, sodium taurocholate, simethicone, phosphotidylcholine and the like Suitable preservatives for the aqueous suspensions or dispersions described herein include, for example, potassium sorbate, parabens (e.g., methylparaben and propylparaben), benzoic acid and its salts, other esters of parahydroxybenzoic acid such as butylparaben, alcohols such as ethyl alcohol or benzyl alcohol, phenolic compounds such as phenol, or quaternary compounds such as benzalkonium chloride. Preservatives, as used herein, are incorporated into the dosage form at a concentration sufficient to inhibit microbial growth.

Suitable viscosity enhancing agents for the aqueous suspensions or dispersions described herein include, but are not limited to, methyl cellulose, xanthan gum, carboxymethyl cellulose, hydroxypropyl cellulose, hydroxypropylmethyl cellulose, Plasdon® S-630, carbomer, polyvinyl alcohol, alginates, acacia, chitosans and combinations thereof. The concentration of the viscosity enhancing agent will depend upon the agent selected and the viscosity desired.

Examples of sweetening agents suitable for the aqueous suspensions or dispersions described herein include, for example, acacia syrup, acesulfame K, alitame, aspartame, chocolate, cinnamon, citrus, cocoa, cyclamate, dextrose, fructose, ginger, glycyrrhetinate, glycyrrhiza (licorice) syrup, monoammonium glyrrhizinate (MagnaSweet®), maltol, mannitol, menthol, neohesperidine DC, neotame, Prosweet® Powder, saccharin, sorbitol, stevia, sucralose, sucrose, sodium saccharin, saccharin, aspartame, acesulfame potassium, mannitol, sucralose, tagatose, thaumatin, vanilla, xylitol, or any combination thereof.

Methods of Dosing and Treatment Regimens

A method for treating any of the diseases or conditions described herein in a subject in need of such treatment, involves administration of pharmaceutical compositions that include at least one compound of Formula (I), (II), (III), (IV), (V), or (VI) or a pharmaceutically acceptable salt, pharmaceutically acceptable prodrug, or pharmaceutically acceptable solvate thereof, in therapeutically effective amounts to said subject. In another embodiment, the compounds of Formula (I), (II), (III), (IV), (V), or (VI) are used in the preparation of medicaments for the treatment of acute kidney injury (AKI) secondary to a toxic agent (e.g., cisplatin, aminoglycosides, and radiologic contrast material), nociceptive pain, including acute post-operative pain, neuropathic pain (e.g., trigeminal neuralgia, diabetic peripheral neuropathy, and herpetic neuralgia), inflammatory pain, mixed neuropathic pain and inflammatory pain states, rheumatoid arthritis, inflammatory bowel disease, irritable bowel syndrome, osteoarthritis, acute pancreatitis, chronic pancreatitis, pain associated with acute pancreatitis, pain associated with chronic pancreatitis, migraine headache, gout, ankylosing spondylititis, systemic lupus erythematosus (SLE), system inflammatory response syndrome (SIRS), multi-organ dysfunction syndrome (MODS), asthma, chronic obstructive pulmonary disease (COPD), sensitive skin (e.g., acne, rosacea, burning, stinging and contact dermatitis), or pain associated with cancer (e.g., pancreatic cancer, lung cancer, prostate cancer and breast cancer), or conditions as described herein.

In certain embodiments, the compositions containing the compound(s) described herein are administered for prophylactic and/or therapeutic treatments. In certain therapeutic applications, the compositions are administered to a patient already suffering from a disease or condition, in an amount sufficient to cure or at least partially arrest at least one of the symptoms of the disease or condition. Amounts effective for this use depend on the severity and course of the disease or condition, previous therapy, the patient's health status, weight, and response to the drugs, and the judgment of the treating physician. Therapeutically effective amounts are optionally determined by methods including, but not limited to, a dose escalation clinical trial.

In prophylactic applications, compositions containing the compounds described herein are administered to a patient susceptible to or otherwise at risk of a particular disease, disorder or condition. Such an amount is defined to be a "prophylactically effective amount or dose." In this use, the precise amounts also depend on the patient's state of health, weight, and the like. When used in a patient, effective amounts for this use will depend on the severity and course of the disease, disorder or condition, previous therapy, the patient's health status and response to the drugs, and the judgment of the treating physician. In one aspect, prophylactic treatments include administering to a mammal, who previously experienced at least one symptom of the disease being treated and is currently in remission, a pharmaceutical composition comprising a compound of Formula (I), (II), (III), (IV), (V), or (VI) in order to prevent a return of the symptoms of the disease or condition.

In certain embodiments wherein the patient's condition does not improve, upon the doctor's discretion the administration of the compound of Formula (I), (II), (III), (IV), (V), or (VI) is administered chronically, that is, for an extended period of time, including throughout the duration of the patient's life in order to ameliorate or otherwise control or limit the symptoms of the patient's disease or condition.

In certain embodiments wherein a patient's status does improve, the dose of drug being administered may be temporarily reduced or temporarily suspended for a certain length of time (i.e., a "drug holiday"). In specific embodiments, the length of the drug holiday is between 2 days and 1 year, including by way of example only, 2 days, 3 days, 4 days, 5 days, 6 days, 7 days, 10 days, 12 days, 15 days, 20 days, 28 days, or more than 28 days. The dose reduction during a drug holiday is, by way of example only, by 10%-100%, including by way of example only 10%, 15%, 20%, 25%, 30%, 35%, 40%, 45%, 50%, 55%, 60%, 65%, 70%, 75%, 80%, 85%, 90%, 95%, and 100%.

In certain embodiments the dose of drug being administered may be temporarily reduced or temporarily suspended for a certain length of time (i.e., a "drug diversion"). In specific embodiments, the length of the drug diversion is between 2 days and 1 year, including by way of example only, 2 days, 3 days, 4 days, 5 days, 6 days, 7 days, 10 days, 12 days, 15 days, 20 days, 28 days, or more than 28 days. The dose reduction during a drug diversion is, by way of example only, by 10%-100%, including by way of example only 10%, 15%, 20%, 25%, 30%, 35%, 40%, 45%, 50%, 55%, 60%, 65%, 70%, 75%, 80%, 85%, 90%, 95%, and 100%. After a suitable length of time, the normal dosing schedule is optionally reinstated.

In some embodiments, once improvement of the patient's conditions has occurred, a maintenance dose is administered if necessary. Subsequently, in specific embodiments, the dosage or the frequency of administration, or both, is reduced, as a function of the symptoms, to a level at which the improved disease, disorder or condition is retained. In certain embodiments, however, the patient requires intermittent treatment on a long-term basis upon any recurrence of symptoms.

The amount of a given agent that corresponds to such an amount varies depending upon factors such as the particular compound, disease condition and its severity, the identity (e.g., weight, sex) of the subject or host in need of treatment, but can nevertheless be determined according to the particular circumstances surrounding the case, including, e.g., the specific agent being administered, the route of administration, the condition being treated, and the subject or host being treated. In general, however, doses employed for adult human treatment are typically in the range of 0.01 mg-5000 mg per day. In one aspect, doses employed for adult human treatment are from about 1 mg to about 1000 mg per day. In one embodiment, the desired dose is conveniently presented in a single dose or in divided doses administered simultaneously (or over a short period of time) or at appropriate intervals, for example as two, three, four or more sub-doses per day.

In some embodiments, as a patient is started on a regimen of a CSE inhibitor, the patient is also weaned off (e.g., step-wise decrease in dose) a second treatment regimen (e.g., a methylxanthine).

In one embodiment, the daily dosages appropriate for a compound of Formula (I), (II), (III), (IV), (V), or (VI) described herein are from about 0.01 to about 10 mg/kg per body weight. In specific embodiments, an indicated daily dosage in a large mammal, including, but not limited to, humans, is in the range from about 0.5 mg to about 1000 mg, conveniently administered in divided doses, including, but not limited to, up to four times a day. In one embodiment, the daily dosage is administered in extended release form. In certain embodiments, suitable unit dosage forms for oral administration comprise from about 1 to 500 mg active ingredient. In other embodiments, the daily dosage or the amount of active in the dosage form are lower or higher than the ranges indicated herein, based on a number of variables in regard to an individual treatment regime. In various embodiments, the daily and unit dosages are altered depending on a number of variables including, but not limited to, the activity of the compound used, the disease or condition to be treated, the mode of administration, the requirements of the individual subject, the severity of the disease or condition being treated, and the judgment of the practitioner.

Toxicity and therapeutic efficacy of such therapeutic regimens are determined by standard pharmaceutical procedures in cell cultures or experimental animals, including, but not limited to, the determination of the $LD_{50}$ and the $ED_{50}$. The dose ratio between the toxic and therapeutic effects is the therapeutic index and it is expressed as the ratio between $LD_{50}$ and $ED_{50}$. In certain embodiments, the data obtained from cell culture assays and animal studies are used in formulating the therapeutically effective daily dosage range and/or the therapeutically effective unit dosage amount for use in mammals, including humans. In some embodiments, the daily dosage amount of the compounds described herein lies within a range of circulating concentrations that include the $ED_{50}$ with minimal toxicity. In certain embodiments, the daily dosage range and/or the unit dosage amount varies within this range depending upon the dosage form employed and the route of administration utilized.

Combination Therapy

In one embodiment, the CSE inhibitors of Formula (I), (II), (III), (IV), (V), or (VI) are administered to an individual in need thereof in combination with an anti-inflammatory agent. Examples of such anti-inflammatory agents include and are not limited to analgesics, non-steroidal anti-inflammatory drugs (NSAIDs), COX-2 inhibitors, and the like.

In another embodiment, the CSE inhibitors of Formula (I), (II), (III), (IV), (V), or (VI) are administered to an individual in need thereof in combination with a pain medication. Examples of such pain medications include and are not limited to paracetamol, gabapentin, pregablin, duloxetine, the non-steroidal anti-inflammatory drugs (NSAIDs) such as the salicylates, opioid drugs such as morphine and opium, and analogues such as codeine, oxycodone and the like, as well as opioid-sparing compounds.

In additional embodiments, the CSE inhibitors of Formula (I), (II), (III), (IV), (V), or (VI) are administered to an individual in need thereof in combination with an antiseptic agent (e.g., hydrogen peroxide, iodine, chlorhexidine, boric acid, benzalkonium chloride (BAC), cetyl trimethylammonium bromide (CTMB), cetylpyridinium chloride (Cetrim, CPC), benzethonium chloride (BZT) and the like.

In further embodiments, the CSE inhibitors of Formula (I), (II), (III), (IV), (V), or (VI) are administered to an individual in need thereof in combination with an anesthetic agent (e.g., benzocaine, lidocaine and the like).

In additional embodiments, the CSE inhibitors of Formula (I), (II), (III), (IV), (V), or (VI) are administered to an individual in need thereof in combination with one or more agents used to treat allergy, including, but not limited to: antihistamine and decongestant combinations (cetirizine and pseudoephedrine; desloratadine and pseudoephedrine ER; fexofenadine and pseudoephedrine; loratadine and pseudoephedrine); antihistamines (azelastine nasal spray; brompheniramine; brompheniramine oral suspension; carbinoxamine; cetirizine; chlorpheniramine; clemastine; desloratadine; dexchlorpheniramine ER; dexchlorpheniramine oral syrup; diphenhydramine oral; fexofenadine; loratadine; promethazine); decongestants (pseudoephedrine); leukotriene modifiers (montelukast; montelukast granules); nasal anticholinergics (ipratropium); nasal corticosteroids (beclomethasone nasal inhalation; budesonide nasal inhaler; flunisolide nasal inhalation; fluticasone nasal inhalation; mometasone nasal spray; triamcinolone nasal inhalation; triamcinolone nasal spray); nasal decongestants (phenylephrine); nasal mast cell stabilizers (cromolyn nasal spray) and the like.

In further embodiments, the CSE inhibitors of Formula (I), (II), (III), (IV), (V), or (VI) are administered to an individual in need thereof in combination with antibiotics. In yet other embodiments, the CSE inhibitors of Formula (I), (II), (III), (IV), (V), or (VI) are administered to an individual in need thereof in combination with a wound dressing.

Examples of agents suitable for combination therapy with an agent that modulates the activity of the carotid body include carbonic anhydrase inhibitors (e.g., acetazolamide), cholinesterase inhibitors (e.g., donepezil), adenosine inhibitors (e.g., theophylline), progestational agents (e.g., progestone), opiod antagonists (e.g., naloxone), central nervous system stimulants (e.g., nicotine), serotonergic agents (e.g., paroxetine) including selective serotonin reuptake inhibitors (SSRIs), antidepressants (e.g., protriptyline) including conventional and/or tricyclic antidepressants, antihypertensives (e.g., metoprolol, cilazapril, propranolol, atenolol, hydrochlorothiazide), calcium channel antagonists (e.g., isradipine), ACE inhibitors (e.g., spirapril), respiratory stimulants (e.g., doxapram), alpha-2 adrenergic agonists (e.g., clonidine), gama aminobutyric acid agonists (e.g., baclofen), glutamate antagonists (e.g., sabeluzole), or gaseous respiration stimulants such as carbon dioxide.

Combination Formulations and Kits

Also provided herein are kits for therapies described herein. In some embodiments, the kit comprises a CSE inhibitor and a second treatment regimen. Such kits generally will comprise one or more of the active agent as disclosed herein, and instructions for using the kit.

In some embodiments, kits include a carrier, package, or container that is compartmentalized to receive one or more containers such as vials, tubes, and the like, each of the container(s) including one of the separate elements to be used in a method described herein. Suitable containers include, for example, bottles, vials, syringes, and test tubes. In other embodiments, the containers are formed from a variety of materials such as glass or plastic.

In certain embodiments, the pharmaceutical compositions are presented in a pack or dispenser device which contains one or more unit dosage forms containing a CSE inhibitor. In another embodiment, the pack for example contains metal or plastic foil, such as a blister pack.

Assays for Identification of CSE Inhibitors

In some embodiments, CSE inhibitors are identified by use of in vitro assays. By way of example, an in vitro assay for CSE enzyme activity is described in Zhong et al. *Chinese Medical Journal*, 2009, 122, 326-330. In some embodiments, in vitro enzyme assays are adapted for high-throughput screening (HTS) using any suitable method.

In some embodiments, in vivo assays are used to determine the effect of CSE inhibitor. In some embodiments, an in vivo assay for identifying a CSE inhibitor comprises (a) preparing organ or tissue homogenates from a test animal that has been administered a test compound; and (b) calculating $H_2S$ concentration based on absorbance; wherein a decrease in $H_2S$ concentration indicates that the test compound is a CSE inhibitor. In some embodiments of the aforementioned assay, the test animal is subjected to normoxia, acute hypoxia, chronic intermittent hypoxia, hypercapnia, or a combination thereof. Optional intermediate steps include:

effecting enzymatic reaction on L-cysteine;

quenching the enzymatic reaction with zinc acetate and trichloroacetic acid;

reacting the zinc sulfide with acidic N,N-dimethyl-p-phenylendiamine sulfate and ferric chloride; and measuring the absorbance of the assay mixture with a micro-plate reader.

In some embodiments, an in vivo assay for identifying a CSE inhibitor comprises (a) isolating an organ or tissue from a test animal that has been administered a test compound;

(b) challenging the organ or tissue in the recording chamber by perfusing the recording chamber with varying levels of oxygen and/or carbon dioxide; and (c) recording action potentials;

wherein a decrease in action potential indicates that the test compound is a CSE inhibitor. In some embodiments of the aforementioned assay, the test animal is subjected to normoxia, acute hypoxia, chronic intermittent hypoxia, hypercapnia, or a combination thereof. Optional intermediate steps include:

placing the organ or tissue in a recording chamber superfused with warm physiological saline.

Optional instruments for recording action potentials include a suction electrode on a PowerLab/8P machine.

EXAMPLES

The following specific examples are to be construed as merely illustrative, and not limitative of the remainder of the disclosure in any way whatsoever.

All synthetic chemistry was performed in standard laboratory glassware unless indicated otherwise in the examples. Commercial reagents were used as received.

Example 1: Synthesis of 3-(1-(1H-tetrazol-5-yl) hydrazinyl)-N,N-dimethylpropan-1-amine (3)

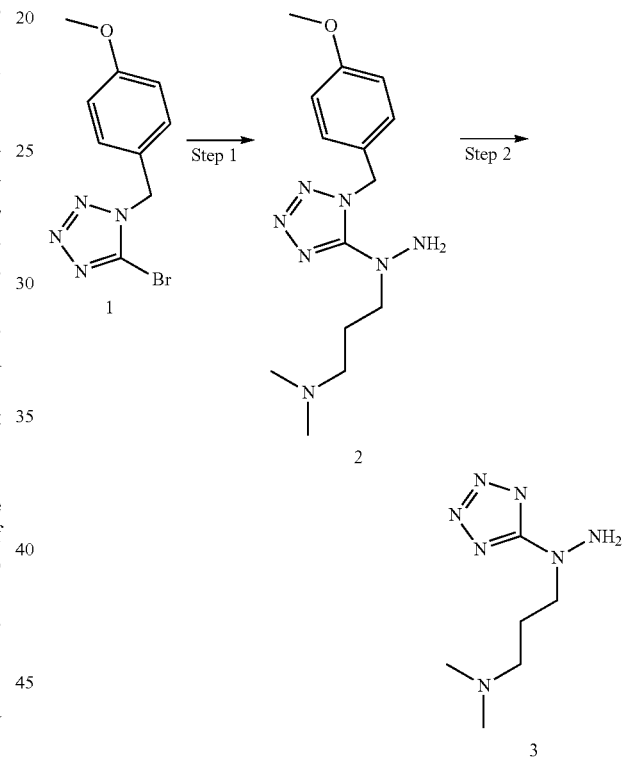

Step 1: Synthesis of 3-(1-(1-(4-methoxybenzyl)-1H-tetrazol-5-yl)hydrazinyl)-N,N-dimethylpropan-1-amine (2)

A mixture of 5-bromo-1-(4-methoxybenzyl)-1H-tetrazole (1) (500 mg, 1.85 mmol) and (3-hydrazinopropyl)dimethylamine (436 mg, 3.72 mmol) in 2-propanol (5 mL) was stirred at 80° C. for 18 h. The reaction mixture was evaporated and the residue was dissolved in a mixture of dichloromethane (20 mL) and brine (10 mL). The layers were separated and the aqueous layer was extracted with dichloromethane (20 mL). The combined organic layers were washed with water (10 mL), dried over sodium sulfate, filtered and evaporated. The crude product was purified by column chromatography eluting with dichloromethane: methanol:triethylamine (100:5:0.5) to give 3-(1-(1-(4-methoxybenzyl)-1H-tetrazol-5-yl)hydrazinyl)-N,N-dimethylpropan-1-amine (2) (320 mg, 1.05 mmol, 57%) as an orange oil. ESMS m/z 306 (M+H)⁺.

Step 2: Synthesis of 3-(1-(1H-tetrazol-5-yl)hydrazinyl)-N,N-dimethylpropan-1-amine (3)

A mixture of (3-{N-[1-(4-methoxybenzyl)-1H-tetrazol-5-yl]hydrazino}propyl)dimethylamine (120 mg, 0.39 mmol) and 6M hydrochloric acid (1.2 mL) was heated under microwave irradiation at 120° C. for 1.5 h. The reaction mixture was evaporated and the crude product was purified by column chromatography eluting with dichloromethane:methanol:ammonia (4:1:0.2→1:1:0.5). The product was triturated with methanol to give 3-(1-(1H-tetrazol-5-yl)hydrazinyl)-N,N-dimethylpropan-1-amine (3) (10 mg, 0.05 mmol, 13%) as a white crystalline solid. ESMS m/z 186 (M+H)⁺; ¹H NMR (400 MHz, D₂O) δ 3.55 (t, J=6.5 Hz, 2H), 3.16-3.27 (m, 2H), 2.90 (s, 6H), 2.03-2.13 (m, 2H).

Example 2: Synthesis of 2-(1-(1H-tetrazol-5-yl)hydrazinyl)-N,N-dimethylethanamine (4)

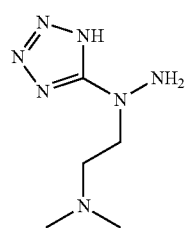

2-(1-(1H-tetrazol-5-yl)hydrazinyl)-N,N-dimethylethanamine (4) was prepared following a similar procedure as in Example 1. ESMS m/z 172 (M+H)⁺.

Example 3: Synthesis of 5-(1-(prop-2-ynyl)hydrazinyl)-1H-tetrazole (7)

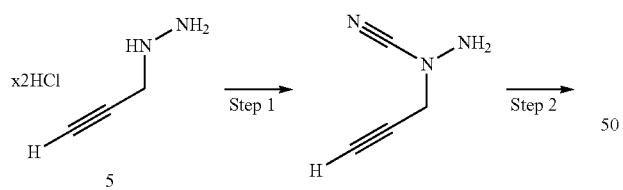

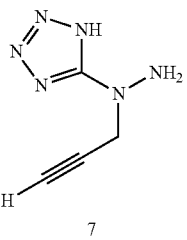

Step 1: Synthesis of 1-(prop-2-ynyl)hydrazinecarbonitrile (6)

To a solution of cyanogen bromide (0.37 g, 3.49 mmol) in dichloromethane (16.5 mL) was added a mixture of prop-2-ynyl hydrazine dihydrochloride (5) (0.50 g, 3.49 mmol) and potassium carbonate (0.97 g, 6.99 mmol) in water (10 mL) at 0° C. The reaction mixture was stirred at 0° C. for 1 h. The layers were separated and the aqueous layer was extracted with dichloromethane (2×30 mL). The combined organic layers were dried over magnesium sulfate, filtered and evaporated. The residue was purified by column chromatography eluting with dichloromethane:methanol (100:1) to give 1-(prop-2-ynyl)hydrazinecarbonitrile (6) (120 mg, 1.26 mmol, 36%) as a pale yellow oil. ESMS m/z 96 (M+H)³⁰; ¹H NMR (500 MHz, CDCl₃) δ 4.25 (br. s, 2H), 3.97 (d, J=2.4 Hz, 2H), 2.53 (t, J=2.4 Hz, 1H).

Step 2: Synthesis of 5-(1-(prop-2-ynyl)hydrazinyl)-1H-tetrazole (7)

A mixture of 1-(prop-2-ynyl)hydrazinecarbonitrile (6) (145 mg, 1.52 mmol), sodium azide (119 mg, 1.83 mmol) and ammonium chloride (98 mg, 1.83 mmol) in N,N-dimethylformamide (2 mL) was stirred at 90° C. for 1 h. The resulting mixture was filtered and evaporated. The residue was purified by column chromatography eluting with dichloromethane:methanol:ammonium hydroxide (4:1:0.2) to give the title compound (120 mg, 0.87 mmol, 57%) as a pale yellow gum. ESMS m/z 139 (M+H)¹; ¹H NMR (500 MHz, DMSO-d₆, salt) δ 4.13 (d, J=2.0 Hz, 2H), 3.05 (br. s, 1H).

Examples 4-11

The following compounds were prepared by the method of Example 3 using an appropriately functionalized hydrazine in Step 1.

| Example | Structure | MW | ESMS m/z | ¹H NMR | Yield |
|---|---|---|---|---|---|
| 4 | 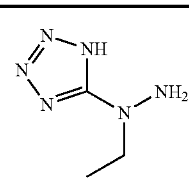 | 128 | 129 | ¹H NMR (500 MHz, DMSO-d₆) salt δ 6.02 (none, 3H), 3.41 (q, J = 7.3 Hz, 2H), 1.10 (t, J = 7.3 Hz, 3H). | 32 |

-continued

| Example | Structure | MW | ESMS m/z | ¹H NMR | Yield |
|---|---|---|---|---|---|
| 5 | 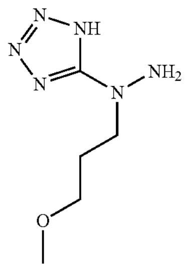 | 172 | 173 | ¹H NMR (500 MHz, DMSO-d₆) δ 4.87 (br. s, 2H), 3.51 (t, J = 7.1 Hz, 2H), 3.36 (t, J = 6.4 Hz, 2H), 3.21 (s, 3H), 1.82-1.90 (m, 2H). | 12 |
| 6 | 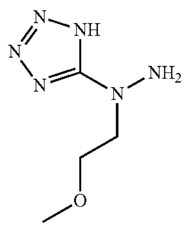 | 158 | 159 | ¹H NMR (500 MHz, CDCl₃) salt δ 5.99 (br. s, 3H), 3.84 (br. s, 2H), 3.74 (t, J = 4.6 Hz, 2H), 3.36 (s, 3H). | 38 |
| 7 | 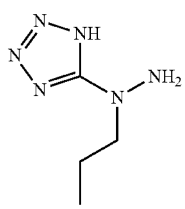 | 142 | 143 | ¹H NMR (500 MHz, D₂O) δ 3.50 (t, J = 7.1 Hz, 2H), 1.62-1.72 (m, 2H), 0.90 (t, J = 7.6 Hz, 3H). | 15 |
| 8 | 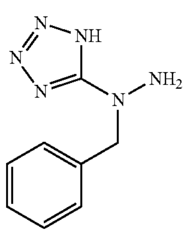 [SMILES: NN(Cc1ccccc1)c1nnn[nH]1] | 190 | 191 | ¹H NMR (500 MHz, DMSO-d₆) salt δ 7.76 (br. s, 3H), 7.27-7.40 (m, 5H), 4.74 (s, 2H). | 9 |
| 9 | 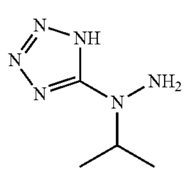 | 142 | 143 | ¹H NMR (500 MHz, DMSO-d₆) δ 4.21-5.12 (m, 2H), 4.09-4.20 (m, 1H), 1.09 (d, J = 6.8 Hz, 6H). | 14 |
| 10 | 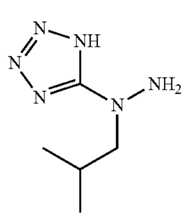 | 156 | 157 | ¹H NMR (400 MHz, D₂O) δ 3.41 (d, J = 7.5 Hz, 2H), 2.06-2.20 (m, 1H), 0.95 (d, J = 6.8 Hz, 6H). | 33 |
| 11 | 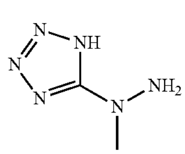 | 114 | 115 | ¹H NMR (500 MHz, DMSO-d₆) δ 14.57 (br. s, 1H), 4.94 (br. s, 2H), 3.14 (s, 3H). | 60 |

Example 12: Synthesis of 3-(1-(1H-tetrazol-5-yl)hydrazinyl)propan-1-amine dihydrochloride (13)

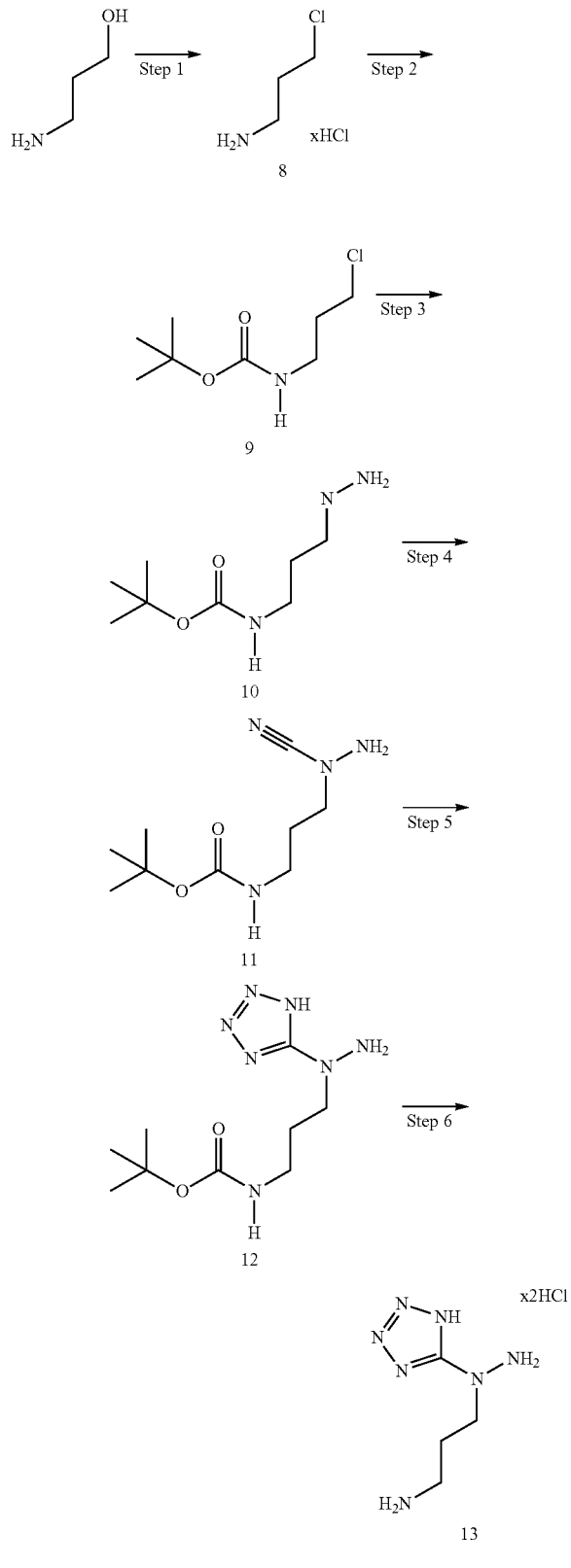

Step 1: Synthesis of 3-chloropropylamine hydrochloride (8)

To solution of thionyl chloride (8.68 g, 1.32 mmol) in anhydrous chloroform (30 mL) was added dropwise to 3-aminopropan-1-ol (4.49 g, 59.19 mmol) while maintaining the temperature at 0-10° C. The mixture was allowed to warm to room temperature and then heated at reflux for 3 h. The mixture was cooled to room temperature and the precipitate was collected to give 3-chloropropylamine hydrochloride (8) (7.07 g, 55.15 mmol, 93%) as a green solid. ESMS m/z 94 (M+H)+.

Step 2: Synthesis of tert-butyl 3-chloropropylcarbamate (9)

A mixture of 3-chloropropylamine hydrochloride (8) (5.00 g, 38.46 mmol) and triethylamine (4.11 g, 40.58 mmol) in dichloromethane was stirred at room temperature for 30 min. The mixture was cooled to 0° C. and a solution of di-tert-butyl dicarbonate (8.86 g, 40.58 mmol) in dichloromethane (30 mL) was added. The mixture was stirred at room temperature for 2 h. The reaction mixture was washed with 10% aqueous potassium hydrogen sulfate (40 mL) and water (40 mL). The organic layer was dried over sodium sulfate, filtered and evaporated to give tert-butyl 3-chloropropylcarbamate (9) (7.89 g, 40.77 mmol, quantitative) as a light brown oil. The crude material was used in the next step without further purification. ESMS m/z 138 (M+H−t-Bu)+.

Step 3: Synthesis of tert-butyl 3-hydrazinylpropylcarbamate (10)

To a refluxing solution of hydrazine hydrate (6.40 g, 128.00 mmol) in ethanol (14.5 mL) was added a solution of tert-butyl 3-chloropropylcarbamate (9) (3.80 g, 19.62 mmol) in ethanol (14.5 mL), dropwise over 80 min. The mixture stirred at reflux for 1 h. The reaction mixture was then evaporated and the residue diluted with diethyl ether (60 mL). The two layers were separated. The organic layer was washed with saturated sodium carbonate solution (17 mL) and evaporated to give tert-butyl 3-hydrazinylpropylcarbamate (10) (1.60 g, 8.45 mmol, 43%) as a yellow oil. The crude material was used in the next step without further purification. ESMS m/z 190 (M+H)+.

Step 4: Synthesis of tert-butyl 3-(1-cyanohydrazinyl)propylcarbamate (11)

A solution of cyanogen bromide (1.68 g, 15.8 mmol) in dichloromethane (50 mL) was added simultaneously a mixture of tert-butyl 3-hydrazinylpropylcarbamate (10) (3.00 g, 15.85 mmol) in water (16 mL) and a solution of sodium carbonate (837 mg, 7.90 mmol) in water (16 mL) at 0° C. The reaction mixture was stirred at 0° C. for 1 h. The two layers were then separated. The organic layer was dried over sodium sulfate, filtered and evaporated while maintaining the temperature below 10° C. to give tert-butyl 3-(1-cyanohydrazinyl)propylcarbamate (11) (2.12 g, 9.89 mmol, 63%) as a yellow oil. ESMS m/z 159 (M+H−t-Bu)+.

Step 5: Synthesis of tert-butyl 3-(1-(1H-tetrazol-5-yl)hydrazinyl)propylcarbamate (12)

A mixture of tert-butyl 3-(1-cyanohydrazinyl)propylcarbamate (11) (2.12 g, 9.89 mmol), sodium azide (780 mg, 12.00 mmol) and ammonium chloride (642 mg, 12.00 mmol) in anhydrous N,N-dimethylformamide (20 mL) was stirred at 40° C. for 18 h. The reaction mixture was filtered and evaporated. The residue was purified by column chromatography eluting with chloroform:methanol (95:5) to give tert-butyl 3-(1-(1H-tetrazol-5-yl)hydrazinyl)propylcarbamate (12) (1.08, 4.20 mmol, 42%) as a yellow oil. ESMS m/z 258 (M+H)$^+$.

Step 6: Synthesis of 3-(1-(1H-tetrazol-5-yl)hydrazinyl)propan-1-amine dihydrochloride (13)

To tert-butyl 3-(1-(1H-tetrazol-5-yl)hydrazinyl)propylcarbamate (12) (134 mg, 0.52 mmol) was added a 4.0M solution of hydrogen chloride in methanol (1.5 mL), and the mixture was stirred at room temperature for 2 h. The precipitate was collected and washed with methanol (2×0.5 mL) to give 3-(1-(1H-tetrazol-5-yl)hydrazinyl)propan-1-amine dihydrochloride (13) (59 mg, 0.26 mmol, 51%) as a white solid. ESMS m/z 158 (M+H)$^+$; $^1$H NMR (500 MHz, D$_2$O) δ 3.73 (t, J=5.0 Hz, 2H), 3.13 (m, 2H), 2.14 (m, 2H).

Examples 13-15

The following compounds were prepared by the method of Example 12 using an appropriately functionalized amine in Step 1.

Example 16: Synthesis of 5-(3-(1-(1H-tetrazol-5-yl)hydrazinyl)propyl)-1H-tetrazole (19)

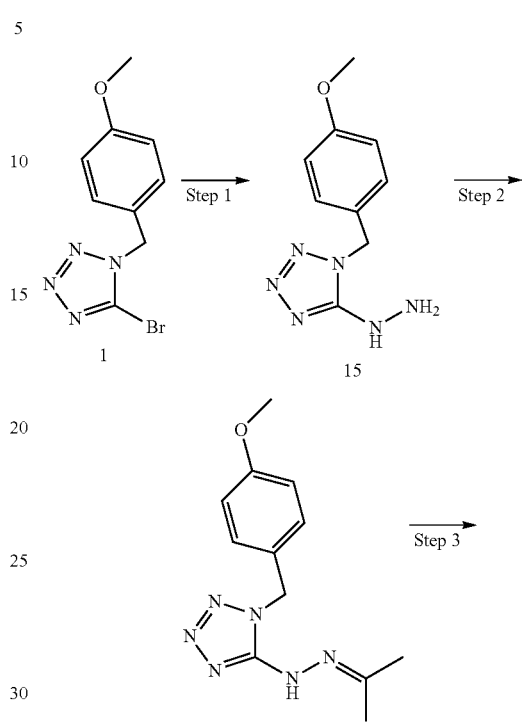

| Example | Structure | MW | ESMS m/z | $^1$H NMR | Yield |
|---|---|---|---|---|---|
| 13 | 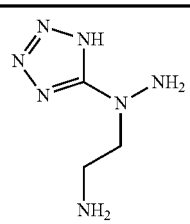 | 143 | 144 | 1H NMR (500 MHz, D2O) δ 3.88 (t, J = 5.6 Hz, 2H), 3.40 (t, J = 5.6 Hz, 2H). | 61 |
| 14 | 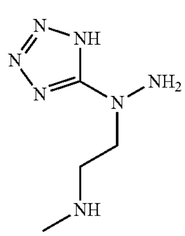 | 157 | 158 | $^1$H NMR (500 MHz, D$_2$O) δ 3.92 (t, J = 5.0 Hz, 2H), 3.45 (t, J = 5.0 Hz, 2H), 2.78 (s, 1H). | 61 |
| 15 | 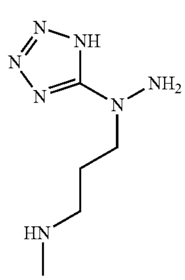 | 171 | 172 | $^1$H NMR (500 MHz, D$_2$O) δ 3.63 (t, J = 5.0 Hz, 2H), 3.07 (m, 2H), 2.67 (s, 3H), 2.06 (m, 2H). | 52 |

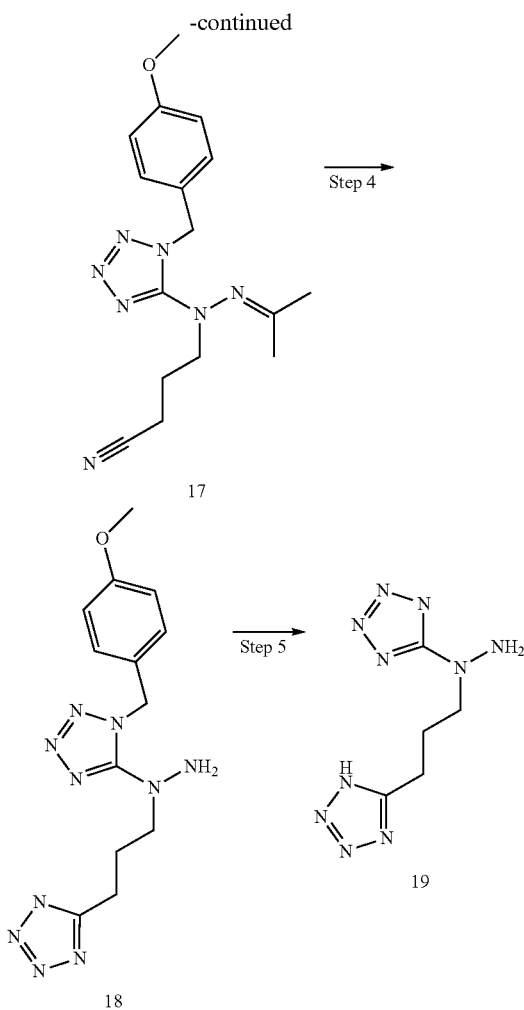

Step 1: Synthesis of 5-hydrazinyl-1-(4-methoxybenzyl)-1H-tetrazole (15)

A mixture of 5-bromo-1-(4-methoxybenzyl)-1H-tetrazole (1) (3.10 g, 11.43 mmol) and hydrazine hydrate (2.21 mL, 45.67 mmol) in 2-propanol (25 mL) was stirred at 60° C. for 16 h. 2-Propanol was evaporated, and the residue was triturated with water (20 mL) to give 5-hydrazinyl-1-(4-methoxybenzyl)-1H-tetrazole (15) (2.04 g, 9.17 mmol, 80%) as an off-white crystalline solid. ESMS m/z 221 (M+H)⁺.

Step 2: Synthesis of 1-(4-methoxybenzyl)-5-(2-(propan-2-ylidene)hydrazinyl)-1H-tetrazole (16)

A mixture of [1-(4-methoxybenzyl)-1H-tetrazol-5-yl]hydrazine (15) (1.80 g, 8.17 mmol), acetone (18 mL) and 3 drops of 4 M hydrochloric acid in diethyl ether was stirred at room temperature for 16 h. The precipitate was collected to give 1-(4-methoxybenzyl)-5-(2-(propan-2-ylidene)hydrazinyl)-1H-tetrazole (16) (1.91 g, 7.33 mmol, 90%) as an off-white crystalline solid. ESMS m/z 261 (M+H)⁺.

Step 3: Synthesis of 4-(1-(1-(4-methoxybenzyl)-1H-tetrazol-5-yl)-2-(propan-2-ylidene)hydrazinyl)butanenitrile (17)

A mixture of 1-(4-methoxybenzyl)-5-(2-(propan-2-ylidene)hydrazinyl)-1H-tetrazole (16) (0.50 g, 1.92 mmol), sodium hydride (0.12 g, 3.00 mmol, 60% dispersion) and anhydrous tetrahydrofuran (5 mL) was stirred at 0° C. for 0.5 h. 4-Bromobutyronitrile (285 μL, 2.87 mmol) was added to the stirred mixture at 0° C., and the reaction mixture was allowed to warm to room temperature and stirred for 18 h. Additional portions of sodium hydride (76 mg, 1.90 mmol, 60%) and 4-bromobutyronitrile (190 μL, 1.90 mmol) were added at room temperature and the reaction mixture was stirred for 24 h and evaporated. The residue was dissolved in water (15 mL) and extracted with dichloromethane (3×15 mL). The combined organic layers were dried over sodium sulfate, filtered and evaporated. The crude product was purified by column chromatography eluting with n-hexane: ethyl acetate (2:3 v/v) to give 4-(1-(1-(4-methoxybenzyl)-1H-tetrazol-5-yl)-2-(propan-2-ylidene)hydrazinyl)butanenitrile (17) (492 mg, 1.50 mmol, 78%) as a yellow oil. ESMS m/z 328 (M+H)⁺.

Step 4: Synthesis of 5-(1-(3-(1H-tetrazol-5-yl)propyl)hydrazinyl)-1-(4-methoxybenzyl)-1H-tetrazole (18)

A mixture of 4-(1-(1-(4-methoxybenzyl)-1H-tetrazol-5-yl)-2-(propan-2-ylidene)hydrazinyl)butanenitrile (17) (490 mg, 1.50 mmol), sodium azide (117 mg, 1.80 mmol) and ammonium chloride (96 mg, 1.80 mmol) in anhydrous N,N-dimethylformamide (10 mL) was stirred at 90° C. for 18 h. More sodium azide (78 mg, 1.20 mmol) and ammonium chloride (64 mg, 1.20 mmol) was added to the mixture and the stirring was continued further at 90° C. for 18 h. Additional portions of sodium azide (2×78 mg, 1.20 mmol) and ammonium chloride (2×64 mg, 1.20 mmol) were added to the mixture at 24 h intervals and the reaction was stirred at 90° C. After a total of 3 days, the mixture was evaporated, the residue was suspended in 2-propanol (20 mL) and filtered. The filtrate was evaporated to give 5-(1-(3-(1H-tetrazol-5-yl)propyl)hydrazinyl)-1-(4-methoxybenzyl)-1H-tetrazole (18) (320 mg, 0.97 mmol, 65%) as a yellow oil. (M+H)⁺331. The crude product was used in the next step without purification.

Step 5: Synthesis of 5-(3-(1-(1H-tetrazol-5-yl)hydrazinyl)propyl)-1H-tetrazole (19)

A mixture of 5-(1-(3-(1H-tetrazol-5-yl)propyl)hydrazinyl)-1-(4-methoxybenzyl)-1H-tetrazole (18) (320 mg, 0.97 mmol) and 6 M hydrochloric acid in water was stirred at 100° C. for 3 h under microwave heating. The mixture was evaporated and purified by column chromatography eluting with dichloromethane:methanol:ammonia (4:1:0.2→3:2:0.5). The product was recrystallized from ethanol to give 5-(3-(1-(1H-tetrazol-5-yl)hydrazinyl)propyl)-1H-tetrazole (19) (15 mg, 0.07 mmol, 7%) as an off-white crystalline solid. ESMS m/z 211 (M+H)⁺; ¹H NMR (400 MHz, MeOH-d4) δ 3.66 (t, J=6.9 Hz, 2H), 3.03 (t, J=7.4 Hz, 2H), 2.23 (quint, J=7.2 Hz, 2H).

Example 17: Synthesis of (E)-5-(2-benzylidenehydrazinyl)-1H-tetrazole (21)

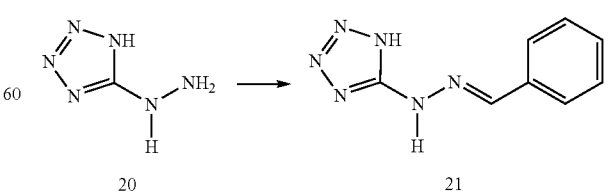

A mixture of 5-hydrazinyl-1H-tetrazole (20) (10 mg, 0.10 mmol) and benzaldehyde (11 mg, 0.10 mmol) in 1,4-dioxane (100 µL) was stirred at room temperature for 18 h. The precipitate was collected to afford (E)-5-(2-benzylidenehydrazinyl)-1H-tetrazole (21) (6.5 mg, 0.03 mmol, 34%) as a white crystalline solid. ESMS m/z 189 (M+H)+; 1H NMR (500 MHz, DMSO-d$_6$) δ 11.79 (s, 1H), 8.04 (s, 1H), 7.78 (d, J=6.9 Hz, 2H), 7.43 (t, J=7.3 Hz, 2H), 7.36-7.41 (m, 1H).

Examples 18-25

The following compounds were prepared by the method of Example 17 using an appropriately functionalized aldehyde or ketone.

| Example | Structure | MW | ESMS m/z | 1H NMR | Yield |
|---|---|---|---|---|---|
| 18 | 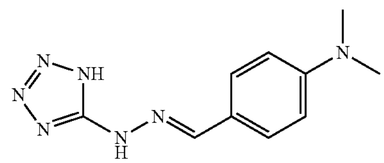 [SMILES: CN(C)c1ccc(/C=N/Nc2nnn[nH]2)cc1] | 231 | 232 | 1H NMR (500 MHz, DMSO-d$_6$) δ 11.37 (s, 1H), 7.90 (s, 1H), 7.57 (d, J = 8.8 Hz, 2H), 6.73 (d, J = 8.8 Hz, 2H), 2.96 (s, 6H). | 54 |
| 19 | 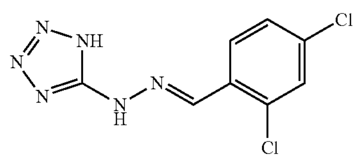 [SMILES: Clc1ccc(/C=N/Nc2nnn[nH]2)c(Cl)c1] | 257 | 257 | 1H NMR (500 MHz, DMSO-d$_6$) δ 12.13 (s, 1H), 8.35 (s, 1H), 8.23 (d, J = 8.3 Hz, 1H), 7.68 (d, J = 2.0 Hz, 1H), 7.54 (dd, J = 8.6, 1.7 Hz, 1H). | 88 |
| 20 | 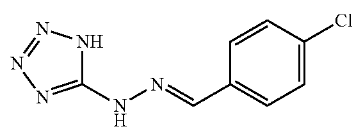 [SMILES: Clc1ccc(/C=N/Nc2nnn[nH]2)cc1] | 223 | 250 | 1H NMR (400 MHz, DMSO-d6) δ 11.88 (s, 1H), 8.04 (s, 1H), 7.82 (d, J = 8.5 Hz, 2H), 7.50 (d, J = 8.5 Hz, 2H). | 48 |
| 21 | 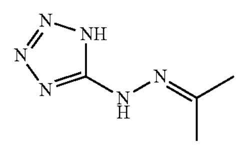 | 140 | 141 | 1H NMR (500 MHz, DMSO-d$_6$) δ 15.04 (br. s, 1H), 10.23 (s, 1H), 1.97 (s, 3H), 1.91 (s, 3H). | 89 |
| 22 | 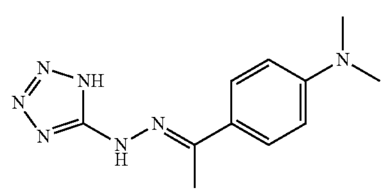 [SMILES: C/C(=N\Nc1nnn[nH]1)c1ccc(N(C)C)cc1] | 245 | 246 | 1H NMR (400 MHz, DMSO-d$_6$) δ 10.59 (br. s, 1H), 9.89 (br. s, 1H), 7.83 (d, J = 8.8 Hz, 2H), 6.89 (br. s, 2H), 2.98 (s, 6H), 2.24 (s, 3H). | 72 |
| 23 | 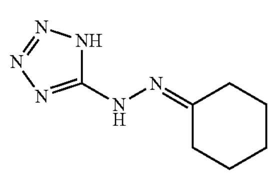 [SMILES: C1CCC(=NNc2nnn[nH]2)CC1] | 180 | 181 | 1H NMR (500 MHz, DMSO-d$_6$) δ 10.39 (s, 1H), 2.39-2.43 (m, 2H), 2.23-2.31 (m, 2H), 1.63 (br. s, 2H), 1.51-1.60 (m, 4H). | 35 |
| 24 | 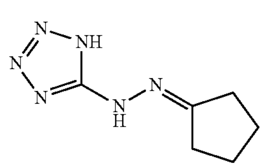 [SMILES: C1CCC(=NNc2nnn[nH]2)C1] | 166 | 167 | 1H N NMR (500 MHz, DMSO-d$_6$) δ 10.16 (s, 1H), 2.30-2.41 (m, 4H), 1.73-1.81 (m, 2H), 1.66-1.73 (m, 2H). | 42 |
| 25 | 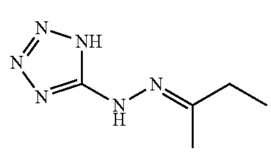 | 154 | 155 | 1H NMR (500 MHz, DMSO-d$_6$, 4:1 Z:E isomers) δ 10.34 (br. s, 0.2H), 10.22 (br. s, 0.8H), 2.34 (q, J = 7.3 Hz, 0.4H), 2.26 (q, J = 7.3 Hz, 1.6H), 1.95 (s, 0.6H), 1.89 (s, 2.4H), 1.07 (t, J = 7.3 Hz, 2.4H), 1.02 (t, J = 7.3 Hz, 0.6H). | 52 |

Example 26: Synthesis of (E)-3-(2-(1H-tetrazol-5-yl)hydrazono)-1-(4-(dimethylamino)phenyl)propan-1-one (23)

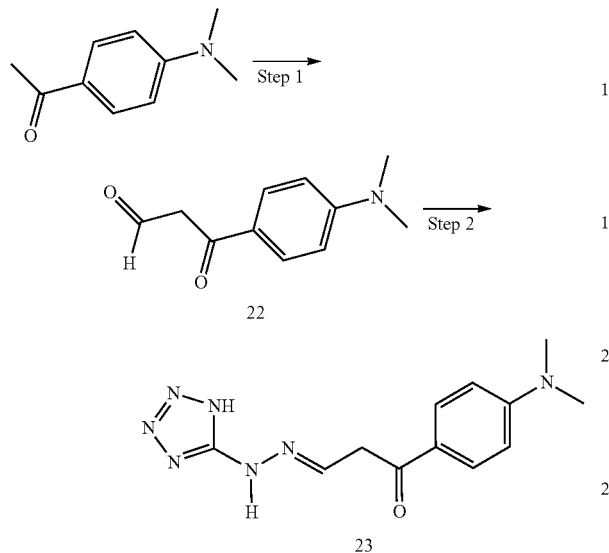

Step 1: Synthesis of 3-(4-(dimethylamino)phenyl)-3-oxopropanal (22)

To a mixture of 4-dimethylaminoacetophenone (1.00 g, 6.13 mmol) and ethyl formate (580 µL, 7.16 mmol) in anhydrous tetrahydrofuran (10 mL) was added 25% sodium methoxide in methanol (1.70 mL, 7.18 mmol) at 0-5° C. The reaction mixture was stirred for 1 h at this temperature, then for 18 h at room temperature. The precipitate was collected and washed with diethyl ether (10 mL) to afford 3-(4-(dimethylamino)phenyl)-3-oxopropanal (22) (0.53 g, 2.48 mmol, 40%) as a pale yellow crystalline solid. ESMS m/z 192 (M+H)$^+$.

Step 2: Synthesis of (E)-3-(2-(1H-tetrazol-5-yl)hydrazono)-1-(4-(dimethylamino)phenyl)propan-1-one (23)

To a mixture of 3-(4-(dimethylamino)phenyl)-3-oxopropanal (22) (50 mg, 0.23 mmol) and ethanol (3 mL) was added (1H-tetrazol-5-yl)hydrazine hydrochloride (37 mg, 0.27 mmol) at 0° C. The reaction mixture was stirred at this temperature for 10 min. The precipitate was collected and washed with ethanol (1 ml) to afford (E)-3-(2-(1H-tetrazol-5-yl)hydrazono)-1-(4-(dimethylamino)phenyl)propan-1-one (23) (31 mg, 0.11 mmol, 48%, 4:1 E:Z) as a pale yellow crystalline solid. ESMS m/z 274 (M+H)$^+$; $^1$H NMR (500 MHz, DMSO-d$_6$) δ 11.41 (s, 0.8H), 10.93 (s, 0.2H), 7.80-7.89 (m, 2H), 7.56 (t, J=5.6 Hz, 0.8H), 7.09 (t, J=5.1 Hz, 0.2H), 6.71-6.78 (m, 2H), 4.10 (d, J=5.4 Hz, 0.4H), 3.93 (d, J=5.9 Hz, 1.6H), 3.04 (s, 1.2H), 3.03 (s, 4.8H).

Example 27: Synthesis of (E)-N,N-dimethyl-4-((2-methyl-2-(1H-tetrazol-5-yl)hydrazono)methyl)aniline (26)

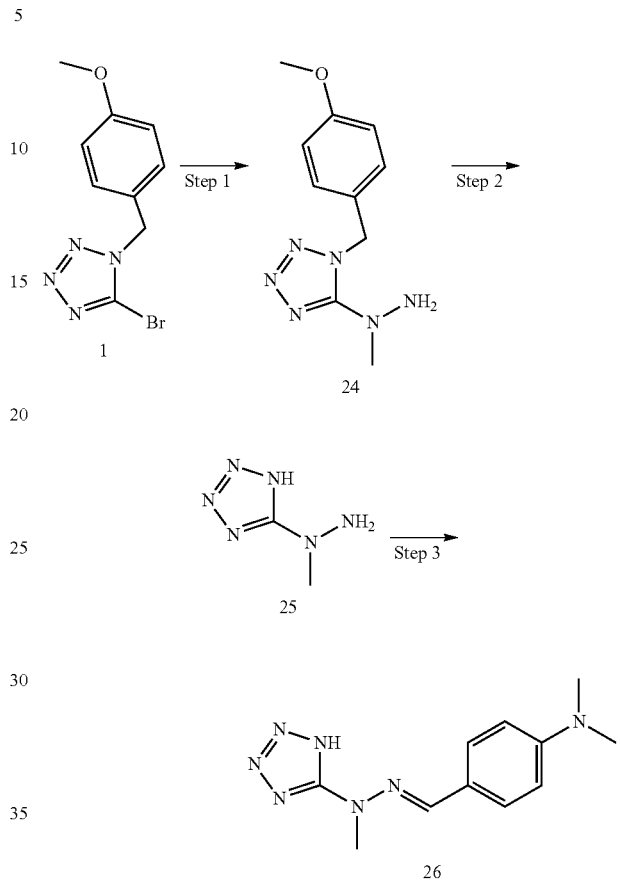

Step 1: Synthesis of 1-(4-methoxybenzyl)-5-(1-methylhydrazinyl)-1H-tetrazole (24)

A mixture of 5-bromo-1-(4-methoxybenzyl)-1H-tetrazole (1) (600 mg, 2.23 mmol) and methyl hydrazine (235 µL, 4.46 mmol) in 2-propanol (5.3 mL) was stirred at 60° C. for 20 h. The reaction mixture was evaporated, and the residue was recrystallized from 2-propanol to give 1-(4-methoxybenzyl)-5-(1-methylhydrazinyl)-1H-tetrazole (24) (54 mg, 0.23 mmol, 10%) as an off-white crystalline solid. ESMS m/z 235 (M+H)$^+$.

Step 2: Synthesis of 5-(1-methylhydrazinyl)-1H-tetrazole (25)

A mixture of 1-(4-methoxybenzyl)-5-(1-methylhydrazinyl)-1H-tetrazole (24) (391 mg, 1.67 mmol) and 10% palladium/carbon (195 mg) in methanol (4 mL) was stirred under a hydrogen atmosphere for 20 h. The reaction mixture was filtered through Celite and the filtrate was evaporated. The crude product was recrystallized from 2-propanol (3 mL) to give 5-(1-methylhydrazinyl)-1H-tetrazole (25) (72 mg, 0.63 mmol, 38%) as an off-white crystalline solid. ESMS m/z 114 (M+H)$^+$; $^1$H NMR (500 MHz, DMSO-d$_6$) δ 14.57 (br. s, 1H), 4.94 (br. s, 2H), 3.14 (s, 3H).

Step 3: Synthesis of (E)-N,N-dimethyl-4-((2-methyl-2-(1H-tetrazol-5-yl)hydrazono)methyl)aniline (26)

A mixture of 5-(1-methylhydrazinyl)-1H-tetrazole (25) (20 mg, 0.18 mmol), 4-dimethylaminobenzaldehyde (26 mg, 0.17 mmol) and a drop of 3.8M hydrogen chloride solution in 1,4-dioxane was stirred in 1,4-dioxane (400 µL) at room temperature for 18 h. The precipitate was collected to afford (E)-N,N-dimethyl-4-((2-methyl-2-(1H-tetrazol-5-yl)hydrazono)methyl)aniline (26) (17 mg, 0.07 mmol, 37%) as a white crystalline solid. ESMS m/z 246 (M+H)$^+$; $^1$H NMR (500 MHz, DMSO-d$_6$) δ 7.84 (s, 1H), 7.78 (d, J=8.8 Hz, 2H), 6.92 (br. s, 2H), 3.54 (s, 3H), 3.00 (s, 6H).

Example 28: Synthesis of 5-(1-methyl-2-(propan-2-ylidene)hydrazinyl)-1H-tetrazole (27)

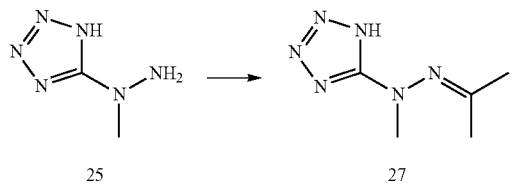

A mixture of 5-(1-methylhydrazinyl)-1H-tetrazole (25) (20 mg, 0.18 mmol) and acetone (500 µL) was stirred at room temperature for 18 h. The reaction mixture was evaporated to give 5-(1-methyl-2-(propan-2-ylidene)hydrazinyl)-1H-tetrazole (27) (27 mg, 0.18 mmol, 100%) as a pale yellow oil. ESMS m/z 155 (M+H)$^+$; $^1$H NMR (500 MHz, CDCl$_3$) δ 3.31 (s, 3H), 2.13 (s, 3H), 2.12 (br. s, 3H).

Example 29: Synthesis of 2-methyl-5-(1-methylhydrazinyl)-2H-tetrazole (28)

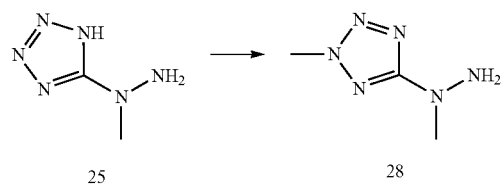

To a mixture of 5-(1-methylhydrazinyl)-1H-tetrazole (25) (100 mg, 0.87 mmol) and methanol (25 mL) was added a solution of diazomethane (8.76 mmol) in diethyl ether (60 mL) at 0° C. The reaction mixture was stirred for 1 h at 0° C., then at room temperature for 18 h. The reaction mixture was evaporated and the crude product was purified by column chromatography eluting with n-hexane:ethyl acetate (3:2) to give 2-methyl-5-(1-methylhydrazinyl)-2H-tetrazole (28) (6 mg, 0.04 mmol, 5%) as a pale yellow crystalline solid. ESMS m/z 129 (M+H)$^+$. $^1$H NMR (500 MHz, MeOH-d$_4$) δ 4.18 (s, 3H), 3.15 (s, 3H), structure determined by $^1$H,$^{15}$N HMBC.

Example 30: Synthesis of 5-(2-(1-ethoxycyclopropyl)hydrazinyl)-1H-tetrazole (29)

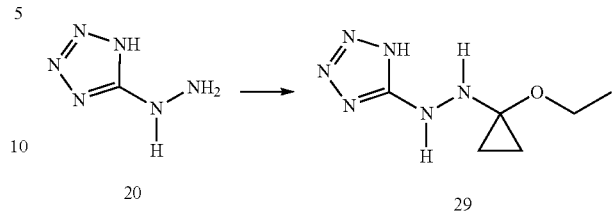

A mixture of 5-hydrazinyl-1H-tetrazole dihydrochloride (150 mg, 0.87 mmol), sodium acetate (141 mg, 1.72 mmol) and (1-ethoxycyclopropoxy)trimethylsilane (174 µL, 0.87 mmol) in ethanol (7.5 mL) was stirred at 80° C. for 16 h. The reaction mixture was evaporated and the residue was triturated with anhydrous tetrahydrofuran (10 mL). The filtrate was evaporated and the crude product was recrystallized from 2-propanol (3 mL). The product was collected and washed with diisopropyl ether (1 mL) to afford 5-(2-(1-ethoxycyclopropyl)hydrazinyl)-1H-tetrazole (29) (30 mg, 0.16 mmol, 18%) as an off-white crystalline solid. ESMS m/z 185 (M+H)$^+$; $^1$H NMR (500 MHz, DMSO-d$_6$) δ 14.47 (br. s, 1H), 8.44 (s, 1H), 6.23 (s, 1H), 3.56 (q, J=6.9 Hz, 2H), 1.03 (t, J=6.9 Hz, 3H), 0.77-0.83 (m, 2H), 0.71-0.77 (m, 2H).

Example 31: Synthesis of 5-(1-ethylhydrazinyl)-1H-1,2,4-triazole hydrochloride (37)

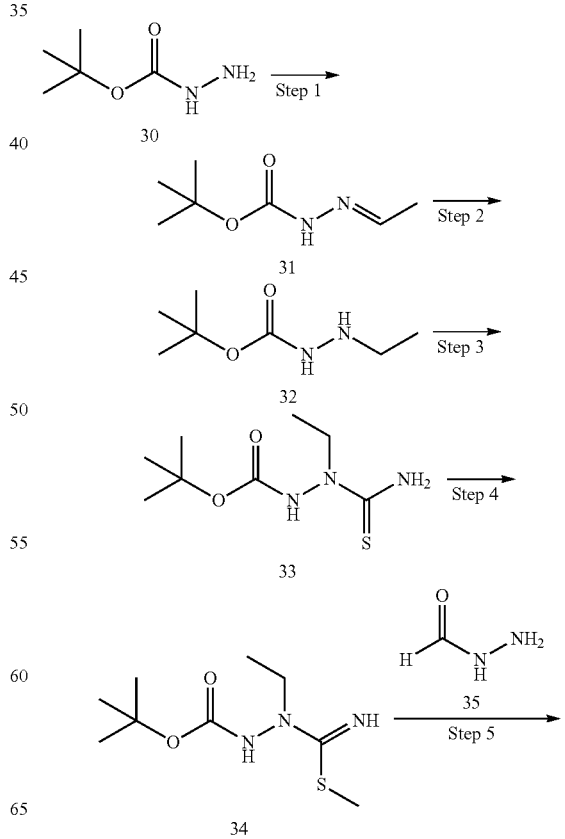

-continued

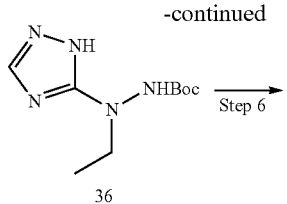

Step 1: Synthesis of (E)-tert-butyl 2-ethylidenehydrazinecarboxylate (31)

To a stirred solution of tert-butyl hydrazinecarboxylate 30 (2.0 g, 12.6 mmol) in toluene (15 ml) was added acetaldehyde (0.7 ml, 13.9 mmol). The solution was heated to 50° C. for 1 h and then stirred at RT for 24 h. The mixture was concentrated to give (E)-tert-butyl 2-ethylidenehydrazinecarboxylate (31) as colorless oil (97.5%). ESMS: 159 ($M^+$+1).

Step 2: Synthesis of tert-butyl 2-ethylhydrazinecarboxylate (32)

To a stirred solution of (E)-tert-butyl 2-ethylidenehydrazinecarboxylate (31) (6.6 g, 37.0 mmol) in THF (50 mL) at −78° C. was added DIBAL (31 ml, 92.6 mmol) as a 1.5 M solution in toluene. The reaction was maintained at −78° C. for 2 h and then −40° C. for 2 h. The mixture was then warmed to room temperature before Rochelle's salt (aqueous potassium sodium tartrate) solution was added and the reaction mixture stirred at room temperature overnight. The organic phase was separated and the aqueous phase extracted with $Et_2O$ (2×75 ml). The combined organic extracts were washed with brine, dried ($Na_2SO_4$), filtered, and concentrated in vacuo. Purification by flash chromatography on silica gel gave tert-butyl 2-ethylhydrazinecarboxylate (32) as colorless oil (3.0 g, 49%). ESMS: 183 ($M^+$+23).

Step 3: Synthesis of tert-butyl 2-carbamothioyl-2-ethylhydrazinecarboxylate (33)

To a stirred solution of tert-butyl 2-ethylhydrazinecarboxylate (32) (5.8 g, 36.6 mmol) in ethyl acetate (30 mL) was added TMSSCN (4.8 g, 36.6 mmol) and the reaction mixture was heated at reflux for 5 h. After completion of reaction, solvent was evaporated under reduced pressure to obtain tert-butyl 2-carbamothioyl-2-ethylhydrazinecarboxylate (33) in 48% yield. $^1$H NMR (400 MHz, $CD_3OD$) δ 1.2 (t, 3H), 1.5 (s, 9H), 4.1 (br s, 2H), 6.2 (br s, 2H), 6.4 (br s, 1H).

Step 4: Synthesis of tert-butyl 2-ethyl-2-(imino (methylthio)methyl)hydrazinecarboxylate (34)

To a stirred solution of tert-butyl 2-carbamothioyl-2-ethylhydrazinecarboxylate (33) (3 g, 13.2 mmol) in acetonitrile (30 ml) was added methyl iodide (9.38 g, 66 mmol) and the reaction mixture was heated at 60° C. for 1 h. After completion of reaction solvent was evaporated under reduced pressure and the crude residue washed with diethyl ether and was dried to obtain tert-butyl 2-ethyl-2-(imino (methylthio)methyl)hydrazinecarboxylate (34) in 94% yield. ESMS: 234.1 ($M^+$+1).

Step 5: Synthesis of tert-butyl 2-ethyl-2-(1H-1,2,4-triazol-5-yl)hydrazinecarboxylate (36)

To a stirred solution of tert-butyl 2-ethyl-2-(imino(methylthio)methyl)hydrazinecarboxylate (34) (500 mg, 2.14 mmol) and formyl hydrazide (35) (155 mg, 2.57 mmol) in dimethyl formamide (10 ml) was added diisopropylethyl amine (830 mg, 6.43 mmol) and the reaction mixture was heated to reflux for 15 h. After completion of reaction, water was added to reaction mixture, and extracted with ethyl acetate (2×50 ml). The organic layer was separated and dried over sodium sulfate, filtered and concentrated under reduced pressure to afford the crude product. The crude product was purified by silica gel column chromatography to obtain tert-butyl 2-ethyl-2-(1H-1,2,4-triazol-5-yl)hydrazinecarboxylate (36) in 12% yield. $^1$H NMR (400 MHz, $CD_3OD$) δ 1.2 (t, 3H), 1.5 (s, 9H), 3.6 (br s, 2H), 7.7 (br s, 1H).

Step 6: Synthesis of 5-(1-ethylhydrazinyl)-1H-1,2,4-triazole hydrochloride (37)

To a stirred solution of MeOH.HCl (5 ml) was added tert-butyl 2-ethyl-2-(1H-1,2,4-triazol-5-yl)hydrazinecarboxylate (36) (40 mg, 0.17 mmol) and the resulting mixture was stirred for 12 h at room temperature. After completion of reaction, solvent was removed under reduced pressure, washed twice with ether and dried under reduced pressure to afford 5-(1-ethylhydrazinyl)-1H-1,2,4-triazole hydrochloride (37) in 75% yield. $^1$H NMR (400 MHz, CD3OD) δ 1.2 (t, 3H), 3.6 (q, 2H), 8.5 (s, 1H), 10.2-10.4 (brs, 2H). HPLC Purity: 90.89%; ESMS: 127.85 ($M^+$).

Example 32: Synthesis of 3-(1-methylhydrazinyl)-1,2,4-oxadiazol-5(4H)-one hydrochloride (42)

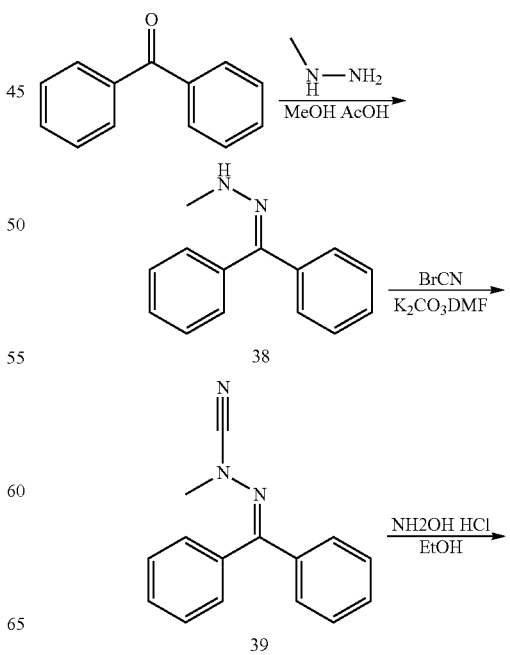

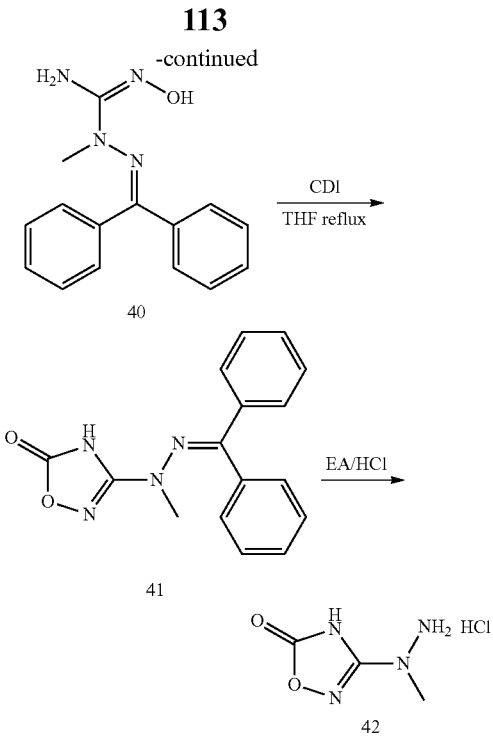

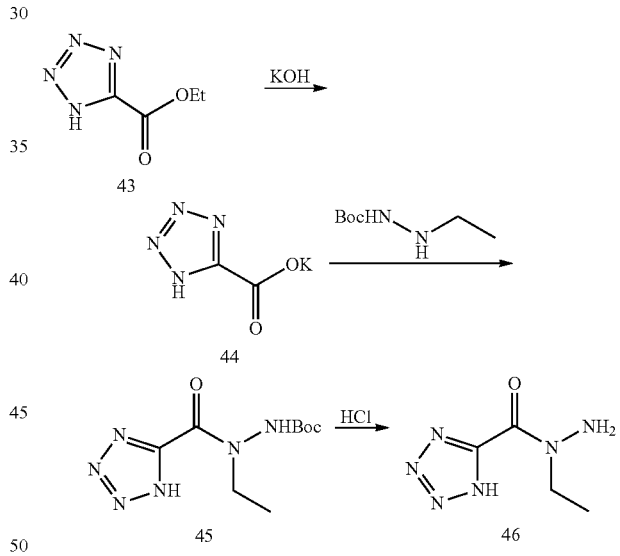

over Na₂SO₄ and concentrated under reduced pressure to afford 40 (5.5 g) as a yellow solid. LCMS (ESI): m/z 269.1 (M+1)⁺.

Step 4: Synthesis of 3-(2-(diphenylmethylene)-1-methylhydrazinyl)-1,2,4-oxadiazol-5(4H)-one (41)

A mixture of 40 (5.5 g, 20 mmol) and CDI (5 g, 30 mmol) in THF (60 mL) was stirred at reflux for 5 h. The mixture was cooled, concentrated under reduced pressure and purified with flash column chromatography (PE/ethyl acetate=3:1) to afford 41 (4 g) as a yellow solid. LCMS (ESI): m/z 295.1 (M+1)⁺.

Step 5: Synthesis of 3-(1-methylhydrazinyl)-1,2,4-oxadiazol-5(4H)-one hydrochloride (42)

To a solution of 41 (0.9 g, 9 mmol) in ethyl acetate (10 mL) was added 4 M HCl in ethyl acetate (15 mL) and the mixture was stirred at room temperature overnight. The mixture was then filtered and the solid was washed with ethyl acetate and MeOH to afford 3-(1-methylhydrazinyl)-1,2,4-oxadiazol-5(4H)-one HCl salt (42) (0.25 g, 1.5 mmol) as a white solid. ¹H NMR (400 MHz, DMSO-d₆): δ3.07 (s, 3H). LCMS (ESI): m/z 131.1 (M+1)⁺.

Example 33: Synthesis of N-ethyl-1H-tetrazole-5-carbohydrazide (46)

Step 1: Synthesis of 1-(diphenylmethylene)-2-methylhydrazine (38)

To a solution of benzophenone (18 g, 100 mmol) in MeOH (200 mL) and AcOH (200 mL) was added methylhydrazine (12 mL, 100 mmol) at 20° C. After stirring at 70° C. for 3 h, the mixture was concentrated, and diluted with ethyl acetate (10 mL) and water (15 mL). The organic layer was separated. The aqueous layer was washed with ethyl acetate (10 mL×2). The combined organic layers were washed with brine, dried over Na₂SO₄, filtered and concentrated under reduced pressure to afford 38 as white oil (10.5 g). LCMS (ESI): m/z 211.1 (M+1)⁺.

Step 2: Synthesis of 2-(diphenylmethylene)-1-methylhydrazinecarbonitrile (39)

A mixture of 38 (10.5 g, 50 mmol) and BrCN (5.3 g, 50 mmol) in DMF (100 mL) was heated to 50° C., then K₂CO₃ was added and stirred at 50° C. overnight. EtOAc (250 mL) was added and the solution was washed with brine (250 mL×3), dried over Na₂SO₄, filtered and concentrated under reduced pressure to afford a residue which was purified by flash column chromatography (PE/ethyl acetate=20:1) to afford 39 (5 g) as a white solid. ¹H NMR (400 MHz, CDCl₃): δ3.39 (s, 3H), 7.35-7.40 (m, 4H), 7.45-7.49 (m, 1H), 7.52-7.55 (m, 5H). LCMS (ESI): m/z 236 (M+1)⁺.

Step 3: Synthesis of (Z)-2-(diphenylmethylene)-N'-hydroxy-1-methylhydrazinecarboximidamide (40)

A mixture of 39 (5.5 g, 20 mmol), hydroxylamine hydrochloride (2.2 g, 30 mmol) and AcONa (3.2 g, 40 mmol) in EtOH (80 mL) was stirred at 25° C. overnight. The solvent was removed under reduced pressure and EtOAc (100 mL) was added, washed with water and brine (100 mL), dried Step 1: Synthesis of potassium 1H-tetrazole-5-carboxylate (44)

To a solution of 43 (500 mg, 3.5 mmol) in EtOH (10 mL) was added KOH (591 mg, 01 M). The mixture was stirred at RT for 3 min and then filtered. The solid was washed with cold EtOH and then dried under vacuum to afford 44 (500 mg) as a white solid. The compound was used in the next step without further purification.

Step 2: Synthesis of tert-butyl 2-ethyl-2-(1H-tetrazole-5-carbonyl)hydrazinecarboxylate (45)

To a mixture of 44 (500 mg, 3.3 mmol) and tert-butyl 2-ethylhydrazinecarboxylate (631 mg, 3.9 mmol) in dichloromethane (20 mL) was added HOBT (533 mg, 3.9 mmol) and EDCI (863 mg, 4.9 mmol). The mixture was stirred at RT for 14 h, washed with water and then the organic layer was concentrated. The residue was purified by HPLC to afford 45 (220 mg) as an oil. $^1$H NMR (400 MHz, CDCl$_3$): δ 1.32 (t, J=7.2 Hz, 3H), 1.42 (s, 9H), 3.84 (q, J=7.2 Hz, 2H), 7.56 (br.s, 1H).

Step 3: Synthesis of N-ethyl-1H-tetrazole-5-carbohydrazide (46)

A mixture of 45 (220 mg) in 4 M HCl/ethyl acetate (15 mL) was stirred at RT for 0.5 h. The solution was concentrated, and the solid was washed with ethyl acetate and filtered to afford N-ethyl-1H-tetrazole-5-carbohydrazide (46) (150 mg) as a white solid. $^1$H NMR (400 MHz, DMSO-d$_6$): δ 1.15-1.33 (m, 3H), 3.63 (m, 1H), 4.04 (br. s., 1H). LCMS (ESI): m/z 157.1 [M+1]$^+$.

Example 34: Synthesis of 1-ethyl-N-(1H-tetrazol-5-yl)hydrazinecarboxamide (49)

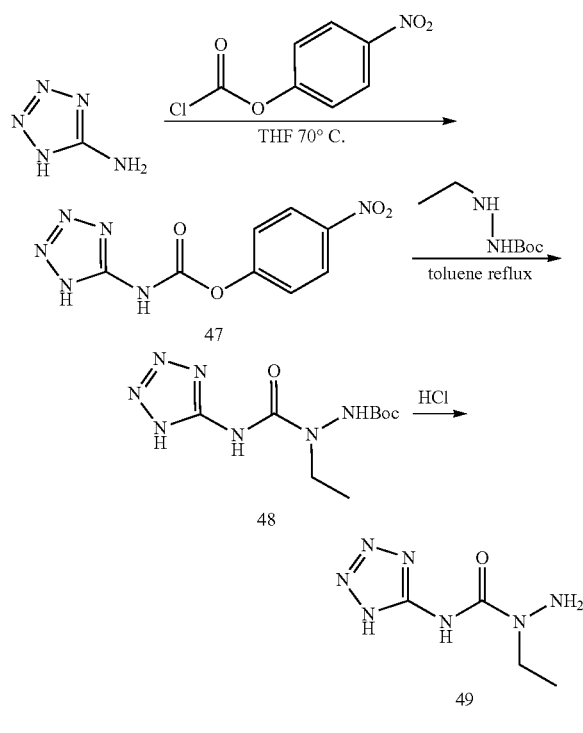

Step 1: Synthesis of 4-nitrophenyl 1H-tetrazol-5-ylcarbamate (47)

A mixture of 2H-tetrazol-5-amine (100 mg, 1.18 mmol) and 4-nitrophenyl carbonochloridate (718.6 mg, 3.54 mmol) in THF (20 mL) was heated to reflux and stirred for 3 h. The solvent was evaporated and the residue was purified on silica gel column (ethyl acetate/PE=1:10) to afford 47 (330 mg) as a white solid.

Step 2: Synthesis of tert-butyl 2-(1H-tetrazol-5-ylcarbamoyl)-2-ethylhydrazinecarboxylate (48)

A mixture of 47 (310 mg, 1.24 mmol) and tert-butyl 2-ethylhydrazinecarboxylate (294.1 mg, 1.86 mmol) in tolu-
ene (20 mL) was heated and refluxed for 3 h. The reaction solution was cooled to room temperature, washed with water and concentrated. The residue was purified by preparative HPLC to afford 48 (193 mg) as an oil.

Step 3: Synthesis of 1-ethyl-N-(1H-tetrazol-5-yl)hydrazinecarboxamide (49)

48 (193 mg) in 4 N HCl-ethyl acetate (15 mL) was stirred at RT for 30 min. The solvent was removed. The residue was washed with ethyl acetate and filtered to afford the compound 1-ethyl-N-(1H-tetrazol-5-yl)hydrazinecarboxamide (49) (100 mg) as a white solid.
$^1$H NMR (400 MHz, D$_2$O): δ 1.07 (t, J=7.2 Hz, 3H), 3.47 (q, J=7.2 Hz, 2H). LCMS (ESI): m/z 172.1 [M+1]$^-$.

Example 35: Synthesis of 1-ethyl-N-(phenylsulfonyl)hydrazinecarboxamide (54)

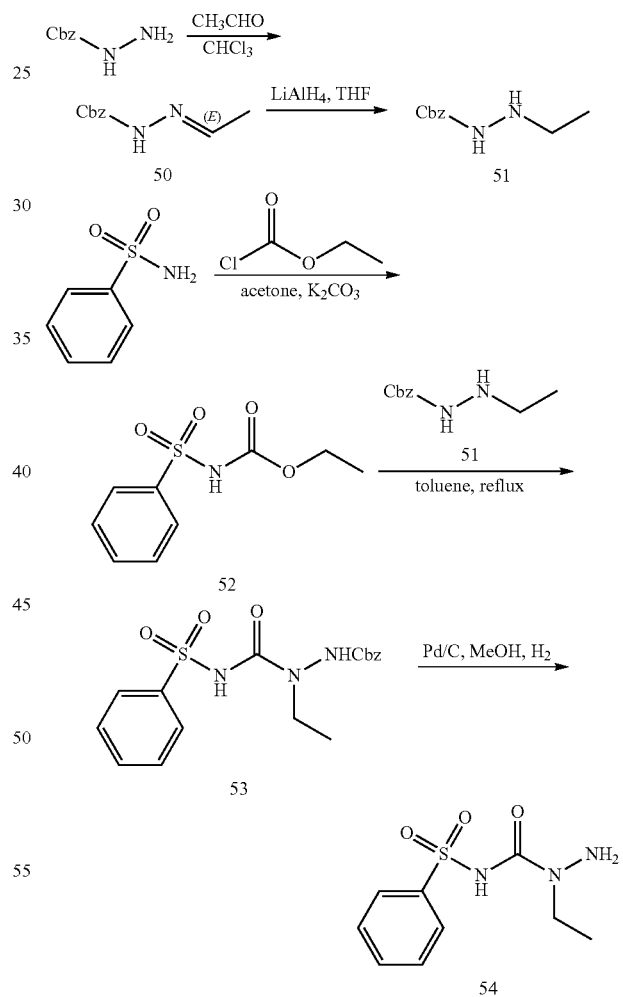

Step 1: Synthesis of (E)-benzyl 2-ethylidenehydrazinecarboxylate (50)

A mixture of benzyl hydrazinecarboxylate (5 g, 30.08 mmol), MgSO$_4$ (5 g) in 30 mL of CHCl$_3$ was added anhydrous CH$_3$CHO (2 g, 45.13 mmol) at 0° C. The mixture was stirred at room temperature for 2 h, then filtered and concentrated to afford 50 (5.9 g) as a yellow solid, which was used in the next step without further purification.

Step 2: Synthesis of benzyl 2-ethylhydrazinecarboxylate (51)

A mixture of LiAlH$_4$ (1.37 g, 36 mmol) in 30 mL of THF was added 50 (5.9 g, crude product from previous step) in 40 mL of THF at 0° C. under nitrogen atmosphere, stirred for 1 h at 0° C. and then 1 h at room temperature. Water (1.37 mL) was then added dropwise followed by 10% aq. NaOH (1.37 mL). The mixture was filtered, concentrated and then purified by flash chromatography on a silica gel (eluting with 5%-50% PE in ethyl acetate) to afford 51 (3.5 g) as a white solid. $^1$H NMR (400 MHz, CDCl$_3$): δ 1.08 (t, J=7.2 Hz, 3H), 2.84-2.98 (m, 2H), 3.63 (s, 1H), 5.15 (s, 2H), 6.60 (br. s, 1H), 7.30-7.44 (m, 5H).

Step 3: Synthesis of ethyl phenylsulfonylcarbamate (52)

A mixture of 51 (1.0 g, 6.36 mmol), K$_2$CO$_3$ (2.2 g, 15.92 mmol) in 50 mL of acetone and ethyl chloroformate (4.04 g, 37.2 mmol) in 5 mL of acetone was stirred at reflux for 1 h. The solvent was evaporated and the residue was dissolved in water, acidified with conc. HCl (pH=1) and extracted with ethyl acetate twice. The combined organic layer was washed with water twice and concentrated to afford 52 (1.1 g) as colorless oil. $^1$H NMR (400 MHz, CDCl$_3$): δ 1.23 (t, J=7.2 Hz, 3H), 4.13-4.20 (m, 2H), 7.56-7.62 (m, 2H), 7.64-7.71 (m, 1H), 7.86 (s, 1H), 8.06-8.09 (m, 2H).

Step 4: Synthesis of benzyl 2-ethyl-2-(phenylsulfonylcarbamoyl)hydrazinecarboxylate (53)

A mixture of 52 (704 mg, 3.07 mmol) and 51 (1.2 g, 6.14 mmol) in 20 mL of toluene was stirred at reflux overnight. The mixture was cooled, concentrated and purified by flash column chromatography (eluting with 5%-20% PE in ethyl acetate) to afford 53 (569 mg) as white solid. $^1$H NMR (400 MHz, CDCl$_3$): δ 1.07 (t, J=7.2 Hz, 3H), 3.60 (br. s, 2H), 5.18 (s, 2H), 6.92 (s, 1H), 7.28-7.48 (m, 5H), 7.49-7.53 (m, 2H), 7.61-7.65 (m, 1H), 8.04 (d, J=7.6 Hz, 2H), 8.64 (br.s, 1H).

Step 5: Synthesis of 3-(1-methylhydrazinyl)-1,2,4-oxadiazol-5(4H)-one hydrochloride (54)

A mixture of 53 (400 mg, 1.06 mmol) and Pd/C (0.2 g) in 40 mL of MeOH was stirred at room temperature for 2 h under an atmosphere of hydrogen (balloon). The mixture was filtered, concentrated and the solid was washed with ethyl acetate/PE (1:1) to afford 1-ethyl-N-(phenylsulfonyl) hydrazinecarboxamide (54) (100 mg) as white solid. $^1$H NMR (400 MHz, DMSO-d$_6$): δ 0.99 (t, J=7.2 Hz, 3H), 3.25-3.35 (m, 3H), 6.70 (br.s, 2H), 7.53-7.70 (m, 3H), 7.90-7.95 (d, J=7.2 Hz, 2H). LCMS (ESI): m/z 244.0 [M+1]$^+$.

Biological Examples

Measurements of H$_2$S levels. H$_2$S levels in the liver were assayed as follows. Briefly, liver tissue homogenates were prepared in 100 mM potassium phosphate buffer, pH 7.4+ 0.5% Triton-X100. The enzyme reaction was carried out in 96 well, deep square well plates with 700 µl Glass Insert (Waters Corporation Cat. #186000349) with TFE/Silicone MicroMat sealing covers (Sun-SRI Cat. #400 026). In the outer well in a total volume of 200 µl the assay mixture contained (in final concentration): L-cysteine, (5 mM); pyridoxal 5'-phosphate, (50 µM); potassium phosphate buffer, pH 7.4, (100 mM); and tissue homogenate (500 µg protein). The glass insert contained 100 µl alkaline zinc acetate solution (1% in 0.1N NaOH) to trap the generated H$_2$S. The reaction mixture was incubated at 37° C. for 3 h and at the end of the reaction, 100 µl N,N-dimethyl-p-phenylenediamine sulfate (20 µM in 7N HCl) and 100 µl ferric chloride (30 µM in 1.2N HCl) was added to the glass insert. Absorbance was measured at 671 nm using a micro-plate reader. A standard curve relating the concentration of Na$_2$S and absorbance was used to calculate H$_2$S concentration and expressed as nanomoles of H$_2$S formed per hour per milligram protein.

Example 1: CSE in Vitro Assay

Test compounds (from DMSO stock solutions) were added to (final concentrations) 20 ug/ml enzyme solution (human, mouse or rat recombinant CSE) plus 50 uM PLP in assay buffer (100 mM potassium phosphate pH 7.6) in 96 well plates in total volume of 190 ul. Plates were incubated for 30 minutes at room temperature before the addition of 10 ul of 200 mM (20× final in assay buffer) DL-Homocysteine substrate to each well. Plates were incubated at 37 C for 3 hours. 50 ul 20 mM DMPDA in 7.2N HCl was added to each well followed by 50 ul 30 mM FeCl3 in 1.2N HCl. Plates were incubated for 10 minutes with shaking at room temperature and then absorbance at 671 nm read in Promega GloMax microplate reader.

TABLE 1

| Example | Structure | IC50 (µM) |
|---|---|---|
| 1 | (structure) | B |
| 2 | (structure) | C |
| 3 | (structure) | A |

TABLE 1-continued

| Example | Structure | IC50 (μM) |
|---|---|---|
| 4 | 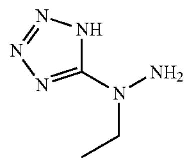 | A |
| 5 | 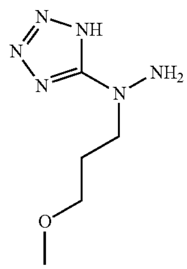 | C |
| 6 | 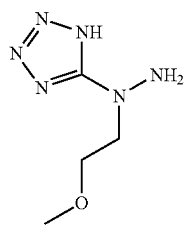 | B |
| 7 | 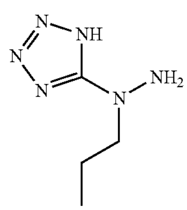 | B |
| 8 | 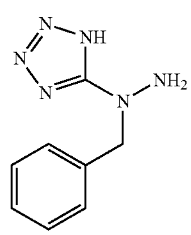 [SMILES: NN(Cc1ccccc1)c1nnn[nH]1] | C |
| 9 | 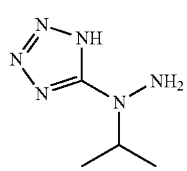 | C |
| 10 | 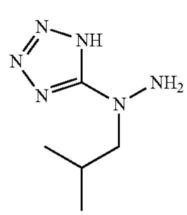 | C |
| 11 | 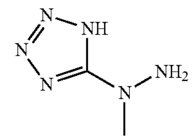 | A |
| 12 | 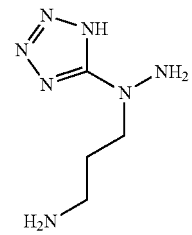 [SMILES: NCCCN(N)c1nnn[nH]1] | A |
| 13 | 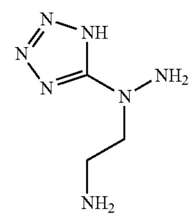 | A |
| 14 | 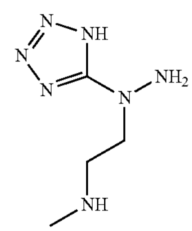 | B |
| 15 | 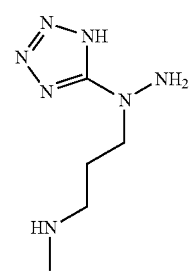 | A |
| 16 | 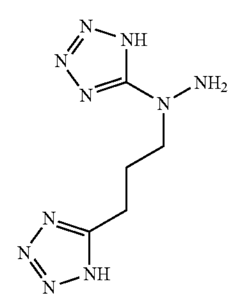 [SMILES: NN(CCCc1nnn[nH]1)c1nnn[nH]1] | B |
| 17 | 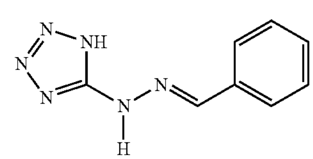 [SMILES: C(=N\Nc1nnn[nH]1)/c1ccccc1] | B |

TABLE 1-continued

| Example | Structure | IC50 (μM) |
|---|---|---|
| 18 | 4-(dimethylamino)benzaldehyde tetrazolyl hydrazone | B |
| 19 | 2,4-dichlorobenzaldehyde tetrazolyl hydrazone | C |
| 20 | 4-chlorobenzaldehyde tetrazolyl hydrazone | A |
| 21 | acetone tetrazolyl hydrazone | A |
| 22 | 4'-(dimethylamino)acetophenone tetrazolyl hydrazone | A |
| 23 | cyclohexanone tetrazolyl hydrazone | A |
| 24 | cyclopentanone tetrazolyl hydrazone | A |
| 25 | butan-2-one tetrazolyl hydrazone | A |
| 26 | 3-(4-(dimethylamino)phenyl)-3-oxopropanal tetrazolyl hydrazone | A |
| 27 | 4-(dimethylamino)benzaldehyde N-methyl tetrazolyl hydrazone | B |
| 28 | acetone N-methyl tetrazolyl hydrazone | A |
| 29 | 2-methyl-5-hydrazinyl tetrazole | C |
| 31 | 1-ethyl-3-hydrazinyl-1,2,4-triazole | C |
| 32 | 3-(1-methylhydrazinyl)-1,2,4-oxadiazol-5(4H)-one HCl | B |
| 33 | N-ethyl tetrazole-5-carbohydrazide | C |
| 34 | 1-ethyl-4-(1H-tetrazol-5-yl)semicarbazide | C |
| 35 | 1-ethyl-4-(phenylsulfonyl)semicarbazide | C |

IC50 (μM) A < 10 μM; 10 μM ≤ B ≤ 100 μM; C > 100 μM

TABLE 2

| Compound | IC50 (μM) |
|---|---|
| 2-hydrazinylacetic acid hydrochloride | A |
| 2-(2-(propan-2-ylidene)hydrazinyl)acetic acid | A |

TABLE 2-continued

| Compound | IC50 (µM) |
| --- | --- |
| 4-((2-(1H-tetrazol-5-yl)hydrazinyl)methyl)-N,N-dimethylaniline | C |
| (E)-4-((2-(1H-tetrazol-5-yl)hydrazono)methyl)-N,N-diethylaniline | B |
| (E)-1-((2-(1H-tetrazol-5-yl)hydrazono)methyl)naphthalen-2-ol | B |
| (E)-5-(2-(benzo[d][1,3]dioxol-5-ylmethylene)hydrazinyl)-1H-tetrazole | C |
| (E)-4-((2-(1H-tetrazol-5-yl)hydrazono)methyl)phenol | B |
| (E)-5-(2-(4-nitrobenzylidene)hydrazinyl)-1H-tetrazole | C |
| (E)-5-(2-(furan-2-ylmethylene)hydrazinyl)-1H-tetrazole | C |
| 5-hydrazinyl-1H-tetrazole | A |
| 5-(hydrazinylmethyl)-1H-tetrazole | B |

IC50 (µM) A < 10 µM; 10 µM ≤ B ≤ 100 µM; C > 100 µM

Example 2: Acute Post Surgical (Brennan) Model of Pain in the Rat

The method, which detects antihyperalgesic activity in rats with postoperative pain, follows that described by Brennan et al (*Pain,* 64, 493-501, 1996).

Incision of the plantar face of the hindpaw in rats is associated with hyperalgesia, allodynia and spontaneous pain which lasts for 3-4 days, and therefore constitutes a model of postoperative pain in humans. Antihyperalgesics reduce these signs of acute pain hypersensitivity.

Rats were anesthetized with isoflurane and a 1 cm-longitudinal incision was made though skin, fascia and muscle of the plantar aspect of the left hindpaw. The wound was then sutured. After local application of antibiotic pomade, the rats were allowed to recover.

Test compounds were dosed two hours prior to pain testing (L-propargylglycine (L-PAG), 100 mpk IP; Compound B (Cmpd B), 30 mpk oral; AMG-517; 3 mpk oral). Compound B is a compound of Formula I-VI. AMG-517 is N-[4-[[6-[4-(trifluoromethyl)phenyl]-4-pyrimidinyl]oxy]-2-benzothiazolyl]-acetamide.

Thermal Hyperalgesia Evaluation: Plantar Test

For heat stimulation, the apparatus (Ugo Basile, Reference: 7371) consisted of individual acrylic plastic boxes (18×11.5×14 cm) placed upon an elevated glass floor. A rat was placed in the box and left free to habituate for 10 minutes. A mobile infrared radiant source (96±10 mW/cm$^2$) was focused under the non-incised and then under the incised hindpaw and the paw-withdrawal latency was automatically recorded. In order to prevent tissue damage the heat source was automatically turned off after 45 seconds.

Tactile Hyperalgesia Evaluation: Pinchmeter Test

The device consists of a pair of large blunt forceps (15 cm long; flat contact area: 7 mm×1.5 mm with smooth edges) equipped with 2 strain gauges connected to a modified electronic dynamometer. The tips of the forceps were placed around the hind paw of the tested animal and the force applied is incremented by hand until the paw withdrawal response. The maximum force applied on the lesioned paw was automatically recorded and displayed by the dynamometer. In order to prevent tissue damage, the applied force was limited to a maximum of 1 kg. This procedure was carried out 3 times and the mean force per paw was calculated.

Example 3a: Chronic Constrictive Injury (Bennett) Model of Neuropathic Pain in the Rat The method, which detects antihyperalgesic activity in rats with neuropathic pain, follows that described by Bennett and Xie (*Pain,* 33, 87-107, 1988).

Chronic constriction injury (CCI) of the common sciatic nerve in rats is associated with hyperalgesia, allodynia and spontaneous pain, and therefore constitutes a model for peripheral neuropathic pain in humans. Antihyperalgesics reduce these chronic signs of pain hypersensitivity.

Rats were anesthetized (sodium pentobarbital 40 mg/kg i.p.) and an incision at mid-thigh level was performed to expose the common left sciatic nerve. Four ligatures spaced 1 mm apart were loosely tied around the sciatic nerve. The wound was then sutured. The rats received a s.c. injection of Duphamox LA® and were allowed to recover.

Test compounds were dosed two hours prior to pain testing (L-PAG, 100 mpk IP; Compound A (Cmpd A), 30 mpk oral; AMG-517; 3 mpk oral). Compound A is 5-(1-ethylhydrazinyl)-1H-tetrazole.

Tactile Allodynia Evaluation: Electronic Von Frey Test

For tactile stimulation, the animal was placed under an inverted acrylic plastic box (18×11.5×14 cm) on a grid floor. The tip of an electronic von Frey probe was then applied with increasing force to the lesioned paw (2 hindpaws for the pre-test) and the force required to induce paw-withdrawal was automatically recorded. This procedure was carried out 3 times and the mean force per paw is calculated (FIG. 1).

Thermal Hyperalgesia Evaluation: Plantar Test

Figure 2:
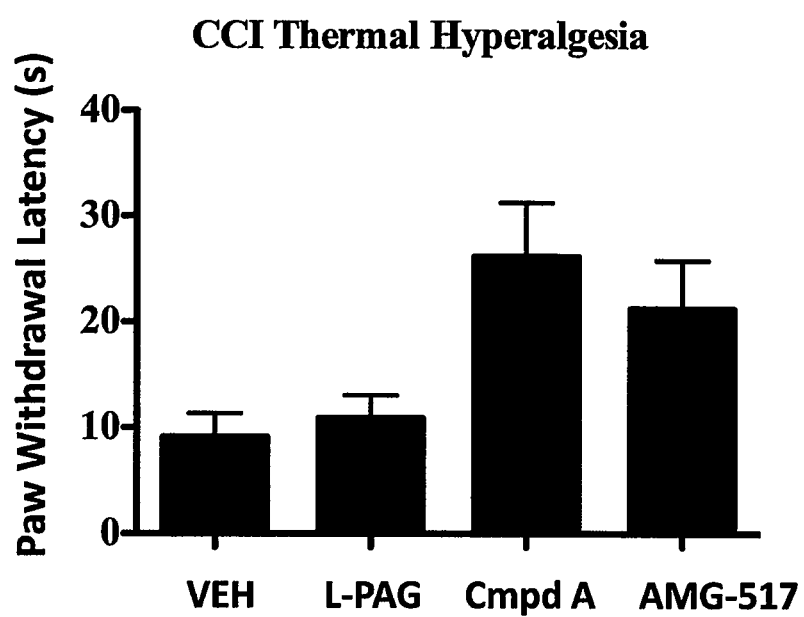
FIG. 2 shows a graph of L-PAG, 100 mpk IP; Compound A (Cmpd A), 30 mpk oral; and AMG-517; 3 mpk oral in the CCI Thermal Hyperalgesia model (Example 3a).

For heat stimulation, the apparatus consists of individual acrylic plastic boxes (18×11.5×14 cm) placed upon an elevated glass floor. A rat was placed in the box and left free to habituate for 10 minutes. A mobile infrared radiant source was then focused under the lesioned hindpaw and the paw-withdrawal latency was automatically recorded. In order to prevent tissue damage the heat source was automatically turned off after 45 seconds (FIG. 2).

Tactile Hyperalgesia Evaluation: Pinchmeter Test

Figure 3:
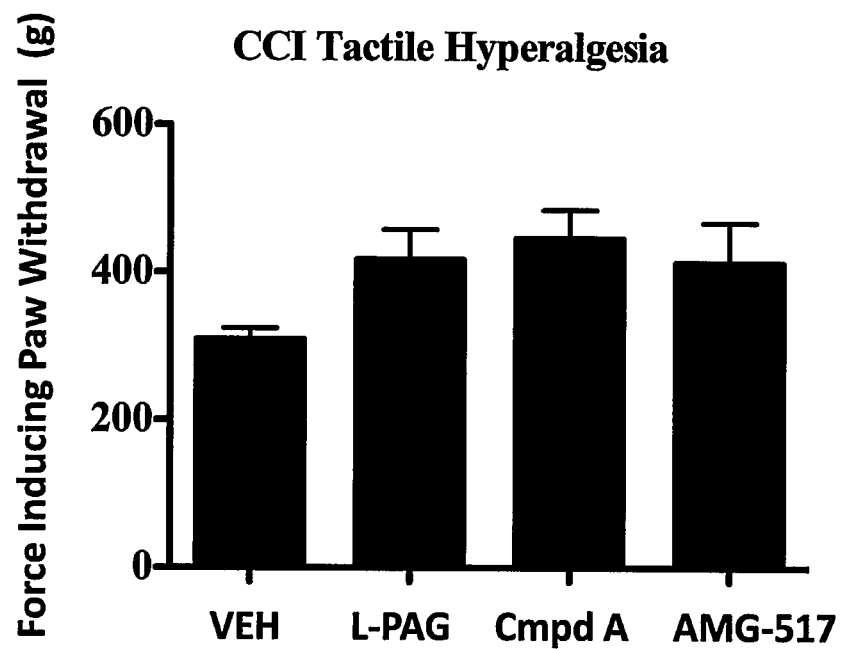
FIG. 3 shows a graph of L-PAG, 100 mpk IP; Compound A (Cmpd A), 30 mpk oral; and AMG-517; 3 mpk oral in the CCI Tactile Hyperalgesia model (Example 3a).

The device consists of a pair of large blunt forceps (15 cm long; flat contact area: 7 mm×1.5 mm with smooth edges) equipped with 2 strain gauges connected to a modified electronic dynamometer. The tips of the forceps were placed around the hind paw of the tested animal and the force applied is incremented by hand until the paw withdrawal response. The maximum force applied on the lesioned paw was automatically recorded and displayed by the dynamometer. In order to prevent tissue damage, the applied force was limited to a maximum of 1 kg. This procedure was carried out 3 times and the mean force per paw was calculated (FIG. 3).

Example 3b: Chronic Constrictive Injury (Bennett) Model of Neuropathic Pain in the Rat The method, which detects antihyperalgesic activity in rats with neuropathic pain, follows that described by Bennett and Xie (*Pain,* 33, 87-107, 1988).

Chronic constriction injury (CCI) of the common sciatic nerve in rats is associated with hyperalgesia, allodynia and spontaneous pain, and therefore constitutes a model for peripheral neuropathic pain in humans. Antihyperalgesics reduce these chronic signs of pain hypersensitivity.

Rats were anesthetized (2.5% Isoflurane) and an incision at mid-thigh level was performed to expose the common left sciatic nerve through the biceps femoralis muscle. Four chromic gut (3/0) ligatures spaced 1 mm apart were loosely tied around the sciatic nerve. The wound was then closed. The rats received a s.c. injection of amoxicillin (4 mg/kg) and were allowed to recover.

Test compounds were dosed one or two hours prior to pain testing. Compound A (Cmpd A), 1, 3, 10 mg/kg PO 2 hours pre test; Gabapentin; 300 mg/kg PO 1 hour pre test). Compound A 5-(1-ethylhydrazinyl)-1H-tetrazole.

Tactile Allodynia Evaluation: Electronic Von Frey Test

Figure 6:
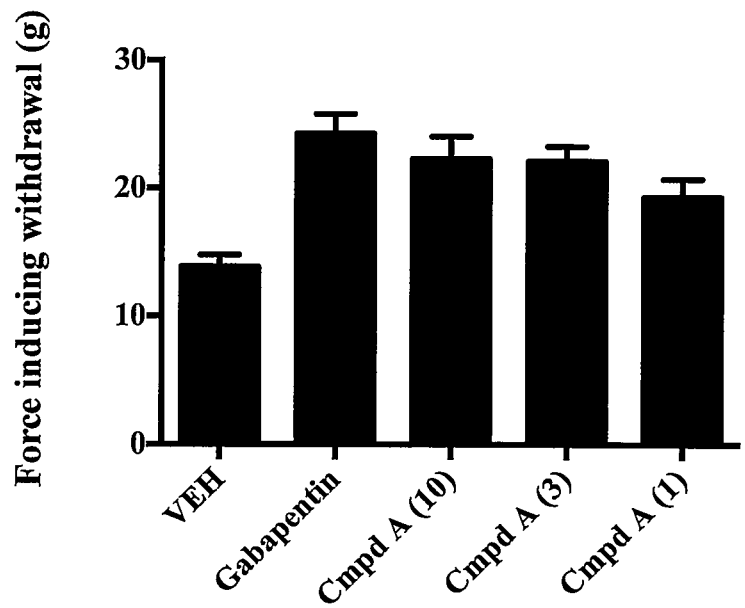
FIG. 6 shows a graph of Compound A (Cmpd A), 1, 3, 10 mpk oral; and Gabapentin; 300 mpk oral in the CCI Tactile Allodynia model (Example 3b).

For tactile stimulation, the animal was placed under an inverted acrylic plastic box (18×11.5×14 cm) on a grid floor. The tip of an electronic von Frey probe was then applied with increasing force to the lesioned paw and the force required to induce paw-withdrawal was automatically recorded. This procedure was carried out 5 times and the mean force per paw was calculated (FIG. 6).

Example 4a: Chronic Inflammatory Pain (Freund's Adjuvant Model) in the Rat

The method, which detects analgesic/anti-inflammatory activity in rats suffering from acute inflammation, follows that described by Butler et al (*Pain*, 48, 73-81, 1992).

An intra-plantar injection of Freund's adjuvant in rats induces clinical signs of inflammation with pain.

On Day 0, rats were weighed and injected with a suspension of Mycobacterium butyricum (Freund's adjuvant) into the plantar surface of one hind paw (0.1 mg in 0.01 ml paraffin oil, 18 µl). The other hind paw was injected with a corresponding volume of saline.

Test compounds were dosed two hours prior to pain testing (L-PAG, 100 mpk IP; Compound A (Cmpd A), 30 mpk oral; AMG-517; 3 mpk oral). Compound A is 5-(1-ethylhydrazinyl)-1H-tetrazole.

Tactile Allodynia Evaluation: Electronic Von Frey Test

Figure 4:
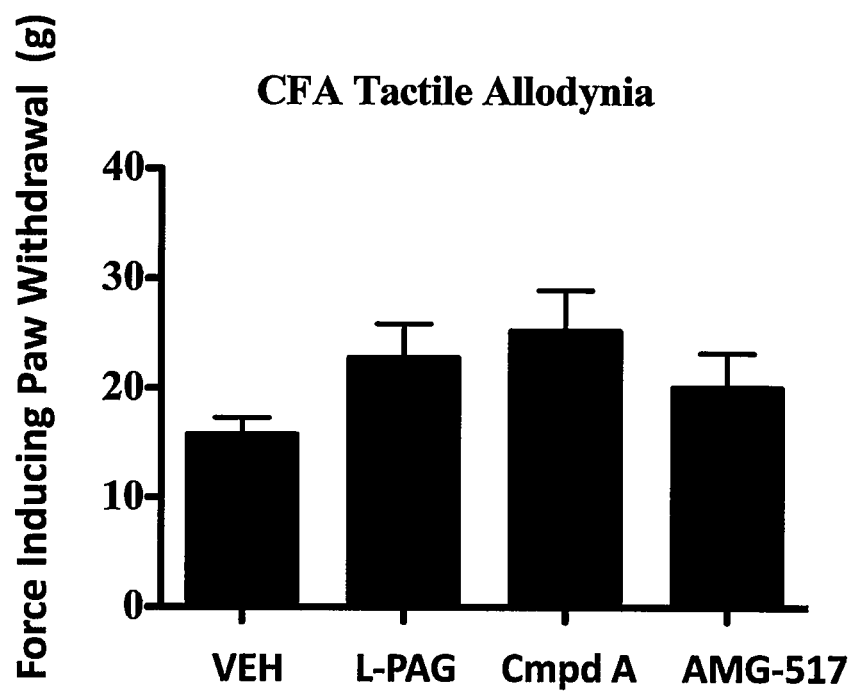
FIG. 4 shows a graph of L-PAG, 100 mpk IP; Compound A (Cmpd A), 30 mpk oral; and AMG-517; 3 mpk oral in the CFA Tactile Allodynia model (Example 4a).

For tactile stimulation, the animal was placed under an inverted acrylic plastic box (18×11.5×14 cm) on a grid floor. The tip of an electronic von Frey probe was then applied with increasing force to the lesioned paw (2 hindpaws for the pre-test) and the force required to induce paw-withdrawal was automatically recorded. This procedure was carried out 3 times and the mean force per paw was calculated (FIG. 4).

Thermal Hyperalgesia Evaluation: Plantar Test

Figure 5:
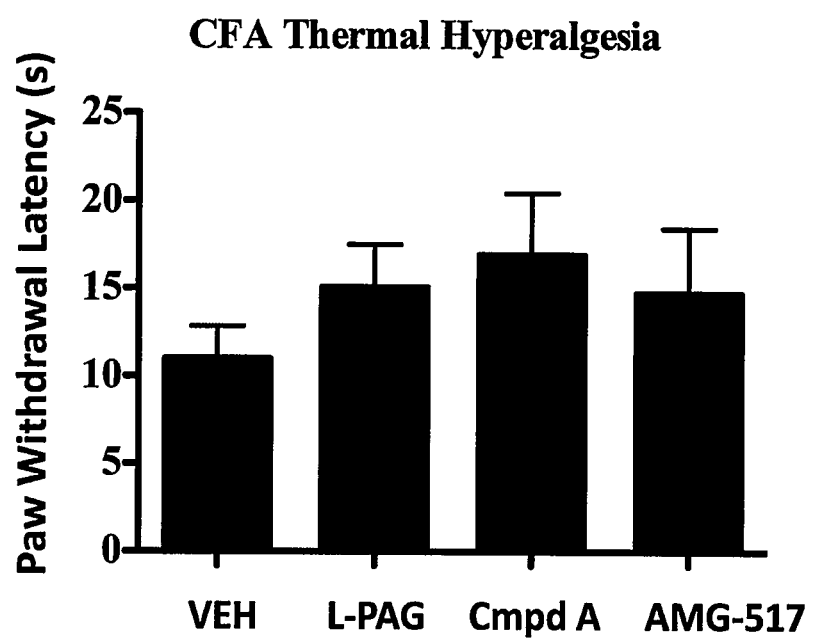
FIG. 5 shows a graph of L-PAG, 100 mpk IP; Compound A (Cmpd A), 30 mpk oral; and AMG-517; 3 mpk oral in the CFA Thermal Hyperalgesia model (Example 4a).

For heat stimulation, the apparatus consists of individual acrylic plastic boxes (18×11.5×14 cm) placed upon an elevated glass floor. A rat was placed in the box and left free to habituate for 10 minutes. A mobile infrared radiant source was then focused first under the non-inflamed and then the inflamed hindpaw and the paw-withdrawal latency was automatically recorded. In order to prevent tissue damage the heat source was automatically turned off after 45 seconds (FIG. 5).

Example 4b: Chronic Inflammatory Pain (Freund's Adjuvant Model) in the Rat

The method, which detects analgesic/anti-inflammatory activity in rats suffering from acute inflammation, follows that described by Butler et al (*Pain*, 48, 73-81, 1992).

An intra-plantar injection of Freund's adjuvant in rats induces clinical signs of inflammation with pain.

On Day 0, rats were weighed and injected with a suspension of Mycobacterium butyricum (Freund's adjuvant) into the plantar surface of one hind paw (0.1 mg in 0.01 ml paraffin oil, 18 µl).

Test compounds were dosed two hours prior to pain testing. Compound A (Cmpd A), 1, 3, 10 mg/kg PO; Naproxen; 30 mg/kg PO). Compound A is 5-(1-ethylhydrazinyl)-1H-tetrazole.

Tactile Allodynia Evaluation: Electronic Von Frey Test

Figure 7:
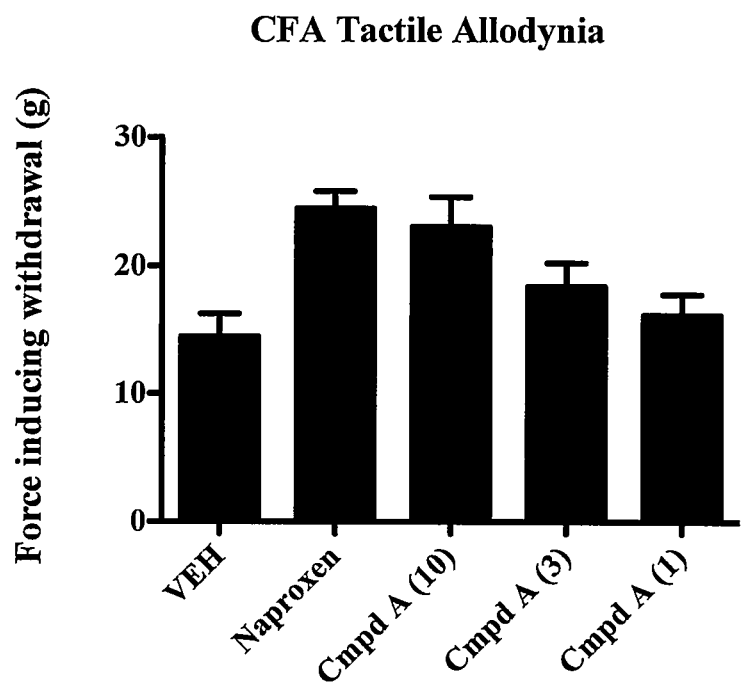
FIG. 7 shows a graph of Compound A (Cmpd A), 1, 3, 10 mpk oral; and Naproxen; 30 mpk oral in the CFA Tactile Allodynia model (Example 4b).

For tactile stimulation, the animal was placed under an inverted acrylic plastic box (18×1.5×14 cm) on a grid floor. The tip of an electronic von Frey probe was then applied with increasing force to the lesioned paw (2 hindpaws for the pre-test) and the force required to induce paw-withdrawal was automatically recorded. This procedure was carried out 3 times and the mean force per paw was calculated (FIG. 7).

Example 5: Arthritic Pain (Monosodium Iodoacetate Model (MIA)) in the Rat

The method, which detects analgesic/anti-inflammatory activity in rats after induction of osteoarthritis, follows that described by Guingamp et al (Arthritis & Rheumatism, 40(9):1670-9, 1997).

An intra-articular injection of monosodium iodoacetate in rats induces clinical signs of inflammatory osteoarthritic pain.

On Day 0, rats were weighed and injected with a suspension of monosodium iodoacetate into the articular space of one knee (hindlimb) (2 mg in 0.04 ml saline).

Test compounds were dosed one or two hours prior to pain testing. Compound A (Cmpd A), 1, 3, 10 mg/kg PO; Gabapentin; 300 mg/kg PO). Compound A is 5-(1-ethylhydrazinyl)-1H-tetrazole.

Tactile Allodynia Evaluation: Electronic Von Frey Test

Figure 8:
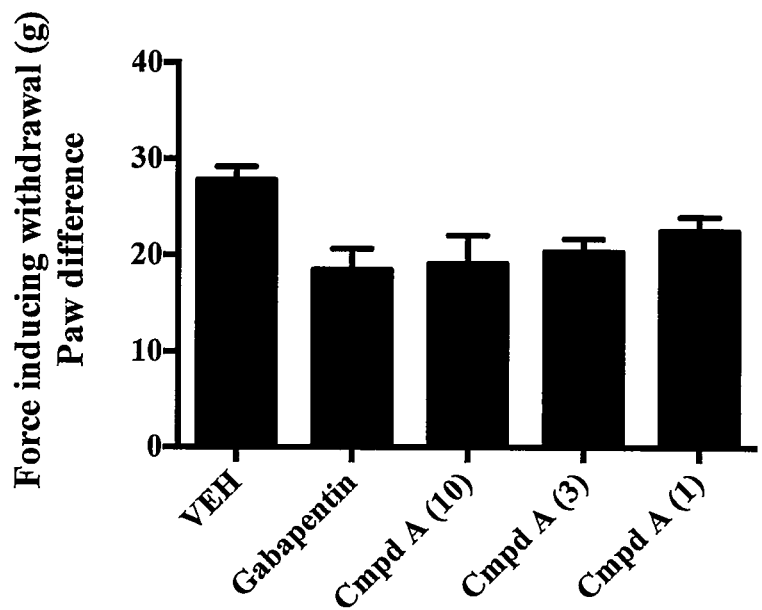
FIG. 8 shows a graph of Compound A (Cmpd A), 1, 3, 10 mpk oral; and Gabapentin; 300 mpk oral in the MIA Tactile Allodynia model (Example 5).

For tactile stimulation, the animal was placed under an inverted acrylic plastic box (18×11.5×14 cm) on a grid floor. The tip of an electronic von Frey probe was then applied with increasing force to the non lesioned and lesioned paws and the force required to induce paw-withdrawal was automatically recorded. This procedure was carried out 3 times on each paw and the mean difference in force that elicits withdrawal was calculated (FIG. 8).

Example 6: CSE Inhibition In Vivo Assay

Target Engagement

To evaluate in vivo CSE inhibition, male Sprague Dawley rats (approximately 300 grams) were orally dosed with 0.1, 0.3, 1, 3 mg/kg Compound A (Compound A is 5-(1-ethylhydrazinyl)-1H-tetrazole) or vehicle (20% HPβCD in water). Two hours post dosing, animals were anesthetized with isoflurane and approximately 1 gram of liver tissue was removed, quickly rinsed in ice cold saline and homogenized in ice cold assay buffer (100 mM potassium phosphate, pH 7.6) plus 0.5% Triton X-100 using a BioSpec Products Tissue-Tearor. Samples were centrifuged for 30 minutes at 4° C. at 20,000×G and the supernatant was collected. Protein was determined by Pierce BCA assay using BSA as a standard.

Figure 9:
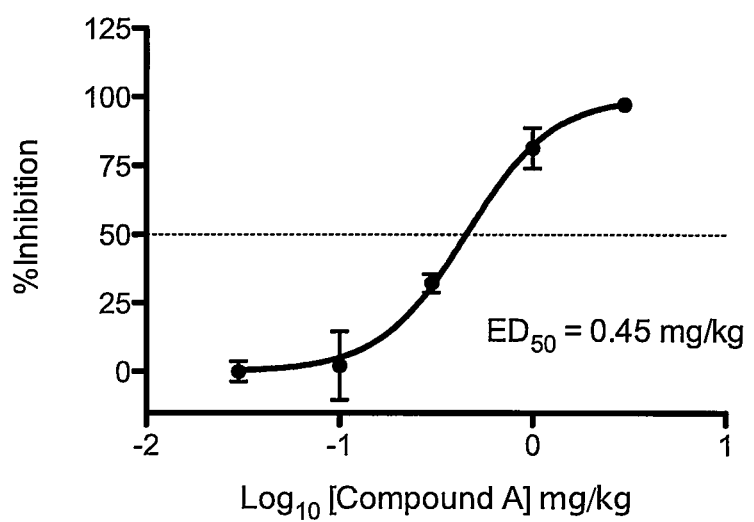
FIG. 9 shows a graph of target engagement of Compound A (Cmpd A), 0.1, 0.3, 1, 3 mpk oral; in the CSE inhibition assay (Example 6).

Inhibition of CSE-mediated $H_2S$ generation from cysteine was determined by incubating 200 µg liver homogenate protein in assay buffer (100 mM potassium phosphate, pH 7.6) plus 10 mM L-cysteine and 50 µM pyridoxal 5'-phosphate (200 µl final volume) for 3 hours at 37° C. in the outer well of 96-well deep well plates containing glass inserts (Waters #186000349) with 100 µl of trapping solution (1% alkaline zinc acetate in 0.2N NaOH) to capture the liberated $H_2S$ and sealed with TFE/silicone sealing mat (Sun SRI #400 026). The reaction was stopped and the $H_2S$ that was generated was determined adding 100 µl of 20 mM N,N-dimethyl-p-phenylenediamine sulphate in 7.2N HCl followed by addition of 100 µl of 30 mM $FeCl_3.6H_2O$ in 1.2N HCl. After mixing for 20 minutes at room temperature, 200 µl of this solution was transferred to a standard 96-well clear bottom assay plate and absorbance at 671 nm was measured using a SpectraMax plate reader (Molecular Devices). Results were normalized to no lysate control level (FIG. 9).

Duration of Effect

To evaluate in vivo duration of effect of CSE inhibition, male Sprague Dawley rats (approximately 300 grams) were orally dosed with 3 mg/kg Compound A (Compound A is 5-(1-ethylhydrazinyl)-1H-tetrazole) or vehicle (20% HPβCD in water). Two, 24, 48, 72 or 96 hours post dosing animals were anesthetized with isoflurane and approximately 1 gram of liver tissue was removed, quickly rinsed in ice cold saline and homogenized in ice cold assay buffer (100 mM potassium phosphate, pH 7.6) plus 0.5% Triton X-100 using a BioSpec Products Tissue-Tearor. Samples were centrifuged for 30 minutes at 4° C. at 20,000×G and the supernatant was collected. Protein was determined by Pierce BCA assay using BSA as a standard.

Figure 10:
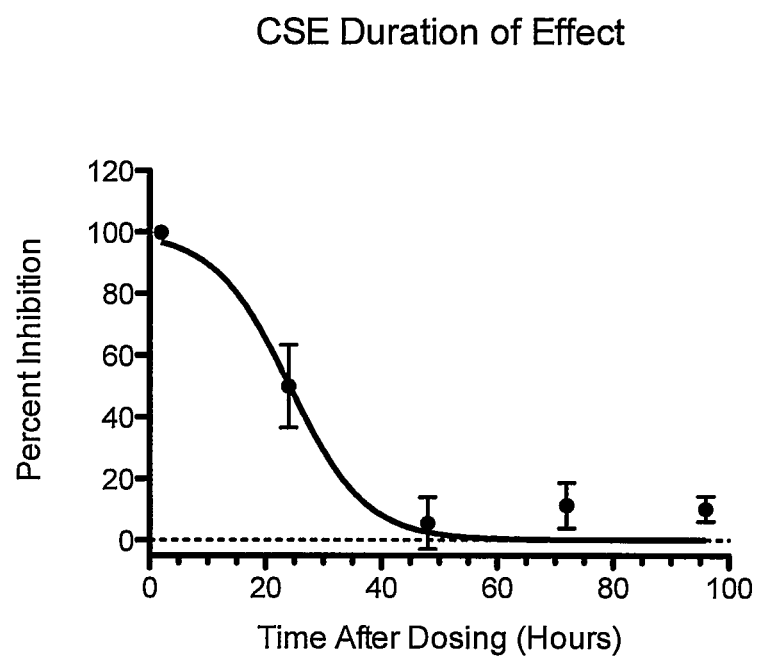
FIG. 10 shows a graph of duration of effect of Compound A (Cmpd A), 3 mpk oral; in the CSE inhibition assay (Example 6).

Inhibition of CSE-mediated $H_2S$ generated from cysteine was determined by incubating 200 µg liver homogenate protein in assay buffer (100 mM potassium phosphate, pH 7.6) plus 10 mM L-cysteine and 50 µM pyridoxal 5'-phosphate (200 µl final volume) for 3 hours at 37° C. in the outer well of 96-well deep well plates containing glass inserts (Waters #186000349) with 100 µl of trapping solution (1% alkaline zinc acetate in 0.2N NaOH) to capture the liberated $H_2S$ and sealed with TFE/silicone sealing mat (Sun SRI #400 026). The reaction was stopped and the $H_2S$ that was generated was determined adding 100 µl of 20 mM N,N-dimethyl-p-phenylenediamine sulphate in 7.2N HCl followed by addition of 100 µl of 30 mM $FeCl_3.6H_2O$ in 1.2N HCl. After mixing for 20 minutes at room temperature, 200 µl of the solution was transferred to a standard 96-well clear bottom assay plate and absorbance at 671 nm was measured using a SpectraMax plate reader (Molecular Devices). Results were normalized to no lysate control level (FIG. 10).

Example 7: A Study to Evaluate the Efficacy, Safety, and Tolerability of a Compound of Formula (I), (II), (III), (IV), (V), or (VI) in Patients With Neuropathic Pain (Postherpetic Neuralgia and Post-Traumatic Neuralgia)

The purpose of this study is to evaluate the safety and effectiveness of CSE Inhibitor in the treatment of moderate to severe neuropathic pain in patients with a diagnosis of postherpetic neuralgia and post-traumatic neuralgia.

| Condition | Intervention | Phase |
|---|---|---|
| Pain Neuralgia, Postherpetic Neuralgia Mononeuropathies | Drug: Compound of Formula (I), (II), (III), (IV), (V), or (VI) Drug: Placebo | Phase 2 |

Study Type: Interventional
Study Design:
Allocation: Randomized
Endpoint Classification: Safety/Efficacy Study
Intervention Model: Parallel Assignment
Masking: Double Blind (Subject, Investigator)
Primary Purpose: Treatment
Primary Outcome Measures:

The daily evening assessment of average pain intensity [Time Frame: Baseline (7 days before randomization) and last 7 days of the 12-week treatment phase] [Designated as safety issue: No]

Secondary Outcome Measures:

Pain at its worst [Time Frame: Daily for 12 weeks] [Designated as safety issue: No]

Brief Pain Inventory [Time Frame: Up to Week 13 (ie, at Visits 1, 3, 7, 8, 9)] [Designated as safety issue: No]

Neuropathic pain symptom inventory [Time Frame: Up to Week 13 (ie, at Visits 1, 3, 7, 8, 9)] [Designated as safety issue: No]

Patient Global Impression of Change [Time Frame: Up to Week 13 (ie, at Visits 1, 3, 7, 8, 9)] [Designated as safety issue: No]

| Arms | Assigned Interventions |
|---|---|
| Experimental: 001 Compound of Formula (I), (II), (III), (IV), (V), or (VI) SC injection (1, 3 or 10 milligrams) once every 28 days | Drug: Compound of Formula (I), (II), (III), (IV), (V), or (VI) Type = exact number, unit = mg, number = 1, 3, or 10, form = solution for injection, route = Subcutaneous use. One injection of 1, 3, or 10 mg of a Compound of Formula (I), (II), (III), (IV), (V), or (VI) every 28 days for up to 52 wks and then every 4, 8, or 12 weeks for up to an additional 52 weeks |
| Placebo Comparator: 002 Placebo SC injection once every 28 days | Drug: Placebo Form = solution for injection, route = Subcutaneous injection. One injection of matching placebo every 28 days for up to 52 wks |

Detailed Description:

The current study is a randomized (study drug assigned by chance), double-blind (neither the study doctor nor the patient knows the name of the assigned drug), placebo-controlled, dose-ranging study to evaluate the efficacy, safety, and tolerability of a compound of Formula (I), (II), (III), (IV), (V), or (VI) in patients with postherpetic neuralgia and post-traumatic neuralgia, followed by a double blind extension and an open-label (study doctor and patient knows the name of the study drug) extension. This study will evaluate the safety and effectiveness of a compound of Formula (I), (II), (III), (IV), (V), or (VI) in the treatment of patients with moderate to severe, chronic, neuropathic pain that is not controlled with or without standard pain therapy and who have a diagnosis of postherpetic neuralgia (PHN) or post-traumatic neuralgia. The total duration of the study will be approximately 130 weeks (i.e., includes screening phase, 12-week double-blind efficacy phase, double-blind safety extension phase, and the open-label safety extension phase). During the 12 week treatment and 40 week double-blind extension phases, PHN patients will receive Placebo, a compound of Formula (I), (II), (III), (IV), (V), or (VI) 1, 3, or 10 mg and post-traumatic neuralgia patients will receive placebo or a compound of Formula (I), (II), (III), (IV), (V), or (VI) 10 mg; all doses will be given as a single, subcutaneous (under the skin) (SC) injection every 28 days. During the 52-week open-label extension phase, all patients will receive a single SC injection of compound of Formula (I), (II), (III), (IV), (V), or (VI) up to 10 mg every 4, 8, or 12 weeks.

Eligibility
Ages Eligible for Study: 18 Years to 80 Years
Genders Eligible for Study: Both
Accepts Healthy Volunteers: No
Inclusion Criteria:

Patients diagnosed with postherpetic neuralgia or post-traumatic neuralgia and who have chronic neuropathic pain (pain persistent for >6 months) that is moderate to severe; Currently taking pain medication but are not adequately controlled by standard of care or are not currently taking pain medications because intolerable to, or not willing to use, standard of care.

Exclusion Criteria:

History of a separate pain condition (e.g., joint osteoarthritis) that is more severe than pain due to diagnosis of PHN or post-traumatic neuralgia Patients with post-traumatic neuralgia that are characteristic of complex regional pain syndrome Type I Patients with lumbar-sacral radiculopathy, failed low-back surgery, or spinal cord injury Patient whose nerve injury or pain is expected to recover in the next 4 months Patients with evidence of another neuropathic pain not under study, such as pain resulting from diabetic painful neuropathy, sensory neuropathies or pain caused by radiation, chemotherapy, alcohol, HIV infection Other peripheral neuropathy, paresthesia, or dysesthesia, or any other previously diagnosed neurologic condition causing the above noted symptoms that is not related with the PHN or post-traumatic neuralgia under the study Women who are pregnant.

History of a separate pain condition (e.g., joint osteoarthritis) that is more severe than pain due to diagnosis of PHN or post-traumatic neuralgia; Patients with post-traumatic neuralgia that are characteristic of complex regional pain syndrome Type I; Patients with lumbar-sacral radiculopathy, failed low-back surgery, or spinal cord injury; Patient whose nerve injury or pain is expected to recover in the next 4 months; Patients with evidence of another neuropathic pain not under study, such as pain resulting from diabetic painful neuropathy, sensory neuropathies or pain caused by radiation, chemotherapy, alcohol, HIV infection; Other peripheral neuropathy, paresthesia, or dysesthesia, or any other previously diagnosed neurologic condition causing the above noted symptoms that is not related with the PHN or post-traumatic neuralgia under the study; Women who are pregnant or breast-feeding; Type I or Type II diabetes.

Example 8: A Study Comparing the Efficacy and Safety of a Compound of Formula (I), (II), (III), (IV), (V), or (VI) to Placebo in Subjects With Diabetic Neuropathic Pain Purpose: To evaluate the safety and efficacy of a compound of Formula (I), (II), (III), (IV), (V), or (VI) compared to placebo in subjects with diabetic neuropathic pain. People with diabetes can, over time develop nerve damage throughout the body with symptoms such as pain, tingling, or numbness (loss of feeling) in the hands, arms, feet and legs.

| Condition | Intervention | Phase |
|---|---|---|
| Diabetic Neuropathic Pain | Drug: Compound of Formula (I), (II), (III), (IV), (V), or (VI) 6 mg<br>Drug: Compound of Formula (I), (II), (III), (IV), (V), or (VI) 12 mg<br>Drug: Compound of Formula (I), (II), (III), (IV), (V), or (VI) 12 mg-18 mg<br>Drug: Placebo comparator<br>Drug: Duloxetine | Phase 2 |

Study Type: Interventional
Study Design:
Allocation: Randomized
Endpoint Classification: Safety/Efficacy Study
Intervention Model: Parallel Assignment
Masking: Double Blind (Subject, Caregiver, Investigator)
Primary Purpose: Treatment
Primary Outcome Measures:
24-hour Average Pain Score [Time Frame: 12 weeks] [Designated as safety issue: No]
Weekly mean of 24-hour average pain score measured by a 11-point Numeric Rating Scale completed on subject's daily diary.
Secondary Outcome Measures:
Neuropathic Pain Symptom Inventory [Time Frame: 12 weeks] [Designated as safety issue: No]
Measures severity of common neuropathic pain qualities (burning, pressure, squeezing)
Patient Global Impression of Change [Time Frame: 12 weeks] [Designated as safety issue: No]
Captures the subject's evaluation of his/her overall general impression of feeling since beginning study medication
Brief Pain Inventory [Time Frame: 12 weeks] [Designated as safety issue: No]
Capture the subject's severity of pain and interference
Neuropathic Pain Impact on Quality of Life Questionnaire [Time Frame: 12 weeks] [Designated as safety issue: No]
Captures the subject's assessment of neuropathic pain and the effect it has on the quality of daily life
EuroQuality of Life-5 Dimension-5 Level [Time Frame: 12 weeks] [Designated as safety issue: No]
Capture's the subject's mobility, self-care, usual activity, pain/discomfort and anxiety/depression

| Arms | Assigned Interventions |
|---|---|
| Experimental: CSE Inhibitor 6 mg Compound of Formula (I), (II), (III), (IV), (V), or (VI) capsules - twice daily | Drug: Compound of Formula (I), (II), (III), (IV), (V), or (VI) 6 mg<br>See arm description for more information |
| Experimental: CSE Inhibitor 12 mg Compound of Formula (I), (II), (III), (IV), (V), or (VI) capsules twice daily | Drug: Compound of Formula (I), (II), (III), (IV), (V), or (VI) 12 mg<br>See arm description for more information |
| Experimental: CSE Inhibitor 12 mg-18 mg Compound of Formula (I), (II), (III), (IV), (V), or (VI) capsules twice daily | Drug: Compound of Formula (I), (II), (III), (IV), (V), or (VI) 12 mg-18 mg<br>See arm description for more information |

| Arms | Assigned Interventions |
|---|---|
| Placebo Comparator: Placebo Placebo capsules twice daily | Drug: Placebo comparator See arm description for more information Other Name: Placebo |
| Active Comparator: Duloxetine Duloxetine capsules once daily | Drug: Duloxetine See arm description for more information |

Eligibility
Ages Eligible for Study: 18 Years to 75 Years
Genders Eligible for Study: Both
Accepts Healthy Volunteers: No
Inclusion Criteria Subject is between the ages of 18-75 years with a diagnosis of diabetes mellitus and must have a diagnosis of painful distal symmetric diabetic polyneuropathy and presence of ongoing pain due to diabetic peripheral neuropathy for at least 6 months.

Subject must have a mean average score of greater than 4 on the 24 hour average pain score (0-10 numerical rating scale) prior to the Baseline Visit.

Subject has been on a medication for diabetic neuropathic pain for the past 3 months.

Exclusion Criteria

Subject has clinically symptomatic neuropathic pain conditions that cannot be distinguished from Diabetic Neuropathic Pain or interfere with the pain assessments of Diabetic Neuropathic Pain.

A subject has newly diagnosed or clinically significant medical conditions or mental disorders that would preclude participation or would interfere with Diabetic Neuropathic Pain assessments or other functions.

Subject has clinically significant abnormalities in clinical laboratory tests.

Subject has taken an opioid chronically, excluding tramadol within the last 3 months prior to Screening.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A compound of Formula (I), having the structure:

Formula (I)

wherein A is selected from and $R_1$ is H, substituted or unsubstituted $C_1$-$C_6$ alkyl, substituted or unsubstituted heteroalkyl, substituted or unsubstituted heterocycloalkyl, substituted or unsubstituted aryl, or substituted or unsubstituted heteroaryl; or a pharmaceutically acceptable salt, solvate, or prodrug thereof.

2. The compound of claim 1, wherein $R_1$ is H, substituted or unsubstituted $C_1$-$C_6$ alkyl, or substituted or unsubstituted heteroalkyl.

3. The compound of claim 2, wherein $R_1$ is H.

4. The compound of claim 2, wherein $R_1$ is substituted or unsubstituted $C_1$-$C_4$alkyl.

5. The compound of claim 4, wherein $R_1$ is —$CH_3$.

6. The compound of claim 4, wherein $R_1$ is —$CH_2CH_3$.

7. A compound of Formula (IV), having the structure:

Formula (IV)

wherein:
A is and
$R_1$ is substituted or unsubstituted $C_2$-$C_6$alkyl, substituted or unsubstituted heteroalkyl, substituted or unsubstituted heterocycloalkyl, or substituted or unsubstituted heteroaryl; or a pharmaceutically acceptable salt, solvate, or prodrug thereof.

8. The compound of claim 7, wherein $R_1$ is substituted or unsubstituted $C_2$-$C_6$alkyl, or substituted or unsubstituted heteroalkyl.

9. The compound of claim 8, wherein $R_1$ is substituted or unsubstituted $C_2$-$C_6$alkyl.

10. The compound of claim 9, wherein $R_1$ is —CH$_2$CH$_3$.

11. A compound of Formula (V), having the structure:

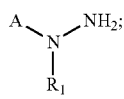

Formula (V)

wherein:

A is

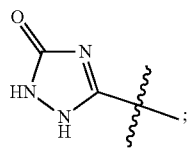

and $R_1$ is H, substituted or unsubstituted $C_3$-$C_6$alkyl, substituted or unsubstituted heteroalkyl, substituted or unsubstituted heterocycloalkyl, substituted or unsubstituted aryl, or substituted or unsubstituted heteroaryl; or a pharmaceutically acceptable salt, solvate, or prodrug thereof.

12. The compound of claim 11, wherein $R_1$ is H, substituted or unsubstituted $C_3$-$C_6$alkyl, or substituted or unsubstituted heteroalkyl.

13. The compound of claim 12, wherein $R_1$ is H.

14. The compound of claim 12, wherein $R_1$ is substituted or unsubstituted $C_3$-$C_6$alkyl.

15. A pharmaceutical composition comprising a pharmaceutically acceptable excipient and a compound of claim 7, or a pharmaceutically acceptable salt, a pharmaceutically acceptable solvate, or a pharmaceutically acceptable prodrug thereof.

16. A method for treating or reducing the incidence of a condition selected from acute kidney injury (AKI) secondary to a toxic agent, nociceptive pain, acute post-operative pain, neuropathic pain, trigeminal neuralgia, diabetic peripheral neuropathy, herpetic neuralgia, post-herpetic neuralgia, inflammatory pain, mixed neuropathic pain and inflammatory pain states, rheumatoid arthritis, inflammatory bowel disease, irritable bowel syndrome, osteoarthritis, acute pancreatitis, chronic pancreatitis, pain associated with acute pancreatitis, pain associated with chronic pancreatitis, migraine headache, gout, ankylosing spondylitis, systemic lupus erythematosus (SLE), system inflammatory response syndrome (SIRS), multi-organ dysfunction syndrome (MODS), asthma, chronic obstructive pulmonary disease (COPD), sensitive skin, acne, rosacea, contact dermatitis, and pain associated with cancer, comprising administering to an individual, having said condition, a therapeutically effective amount of a compound of claim 10 or a pharmaceutically acceptable salt, a pharmaceutically acceptable solvate, or a pharmaceutically acceptable prodrug thereof.

17. The method of claim 16 for treating or reducing the incidence of acute post-operative pain, neuropathic pain, trigeminal neuralgia, diabetic peripheral neuropathy, herpetic neuralgia, post-herpetic neuralgia, inflammatory pain, rheumatoid arthritis, osteoarthritis, or migraine headache, comprising administering, to an individual having said condition, a therapeutically effective amount of a compound of claim 7 or a pharmaceutically acceptable salt, a pharmaceutically acceptable solvate, or a pharmaceutically acceptable prodrug thereof.

18. The method of claim 16, further comprising administration of a second agent selected from carbonic anhydrase inhibitors, cholinesterase inhibitors, adenosine inhibitors, progestational agents, opioid antagonists, central nervous system stimulants, selective serotonin reuptake inhibitors (SSRIs), dual 5-HT-NE reuptake inhibitors (SNRI's), antidepressants, antihypertensives, calcium channel antagonists, ACE inhibitors, respiratory stimulants, alpha-2 adrenergic agonists, gamma aminobutyric acid agonists, antiepileptic drugs, NSAIDs, steroids, and glutamate antagonists.

19. The method of claim 16, further comprising administration of a second agent selected from acetazolamide, theophylline, progesterone, donepezil, naloxone, nicotine, paroxetine, protriptyline, metoprolol, cilazapril, propranolol, atenolol, hydrochlorothiazide, isradipine, spirapril, doxapram, clonidine, baclofen, sabeluzole, gabapentin, pregablin, and duloxetine.

* * * * *